United States Patent
Tran

(10) Patent No.: US 11,617,797 B2
(45) Date of Patent: Apr. 4, 2023

(54) MULTI-TARGETED MULTI-VALENT LIGAND DRUG PARTICLES FOR THE TREATMENT AND PREVENTION OF DISEASES AND CONDITIONS

(71) Applicant: David T. Tran, San Francisco, CA (US)

(72) Inventor: David T. Tran, San Francisco, CA (US)

( * ) Notice: Subject to any disclaimer, the term of this patent is extended or adjusted under 35 U.S.C. 154(b) by 376 days.

(21) Appl. No.: 16/607,711

(22) PCT Filed: Apr. 27, 2018

(86) PCT No.: PCT/US2018/029790
§ 371 (c)(1),
(2) Date: Oct. 23, 2019

(87) PCT Pub. No.: WO2018/200951
PCT Pub. Date: Nov. 1, 2018

(65) Prior Publication Data
US 2020/0306384 A1    Oct. 1, 2020

Related U.S. Application Data

(60) Provisional application No. 62/492,085, filed on Apr. 28, 2017.

(51) Int. Cl.
*A61K 47/68*    (2017.01)
*A61K 9/50*    (2006.01)
*A61K 31/704*    (2006.01)

(52) U.S. Cl.
CPC ........ *A61K 47/6803* (2017.08); *A61K 9/5031* (2013.01); *A61K 31/704* (2013.01)

(58) Field of Classification Search
CPC .................................................. A61K 47/6803
See application file for complete search history.

(56) References Cited

U.S. PATENT DOCUMENTS

| | | |
|---|---|---|
| 2002/0142289 A1 | 10/2002 | Siiman |
| 2003/0125262 A1 | 7/2003 | Kiessling et al. |
| 2004/0115192 A1 | 6/2004 | Lanza et al. |
| 2010/0055093 A1 | 3/2010 | Shepard et al. |
| 2014/0371255 A1 | 12/2014 | Zhang et al. |

OTHER PUBLICATIONS

Tran, D. T. (2013). Receptor-Mediated Uptake and Intracellular Sorting of Multivalent Lipid Nanoparticles against the Epidermal Growth Factor Receptor (EGFR) and the Human EGFR 2 (HER2). UCSF. ProQuest ID: Tran_ucsf_0034D_10722. https://escholarship.org/uc/item/29k490vp (Year: 2013).*
International Search Report and Written Opinion issued in PCT/US18/29790; dated Jul. 3, 2018, 15 pages.

* cited by examiner

*Primary Examiner* — Benjamin J Packard
(74) *Attorney, Agent, or Firm* — McNeill Baur PLLC

(57) ABSTRACT

This disclosure relates to novel ligand-drug particles comprising at least one ligand specific for one or more cell surface receptor molecules for targeting the ligand-drug particles to a target cell. This disclosure also relates to pharmaceutical compositions comprising the particles herein and systems and methods for determining the ligand valency of the particles.

16 Claims, 28 Drawing Sheets

<c> Cetuximab-Fab'-Liposome-F5 scFv

MULTI-TARGETED MULTI-VALENT LIGAND DRUG PARTICLES FOR THE TREATMENT AND PREVENTION OF DISEASES AND CONDITIONS

CROSS-REFERENCE TO RELATED APPLICATIONS

This application is a national phase entry pursuant to 35 U.S.C. § 371 of International Application No. PCT/US2018/029790, filed Apr. 27, 2018, which claims priority to U.S. Provisional Patent Application No. 62/492,085, filed Apr. 28, 2017, each of which is incorporated by reference herein in its entirety.

FIELD

This disclosure relates to novel ligand-drug particles comprising at least one ligand specific for one or more cell surface receptor molecules for targeting the particles to a target cell. This disclosure also relates to pharmaceutical compositions comprising the particles herein and systems and methods for determining the ligand valency of the particles.

BACKGROUND

In the field of targeted drug delivery systems such as liposome-based ligand-drug particles, efficiency has mainly focused on cell-specificity, internalization, and subsequent effects on bioactivity such as cell growth inhibition. To improve the delivery of drugs to targeted cells from these particles, functional groups such as ligands for receptors on the surface of target cells may be incorporated, for example, such as antibody binding fragments. The ideal valence (i.e., number of ligands per particle) of such ligands on the particles, however, has been difficult to determine. Increasing valence does not always improve cell association. In fact, an overly high ligand valency can actually decrease binding and uptake of drugs by target cells.

The cell association and trafficking of ligand-drug particles have been predominately optimized by trial and error experimentation. In designing a particle with an incorporated targeting ligand, for example, researchers may traditionally assess the impact of an array of variables on cellular uptake, such as ligand types, ligand surface valency, particle concentration, incubation time, and temperature. The present disclosure, in contrast, provides ligand-drug particles whose design is based on the use of particular crosslink multivalent binding model, which considers ligand valence, ligand-target equilibrium dissociation constant, and total receptor expression level on the target cell (i.e., average number of receptors per cell). This model has predicted the observed cellular uptake behavior of particular ligand-drugs that target cells expressing HER2, for example, and may be used to design ligand-drug particles with an optimized uptake efficiency of drugs and to reduce the experimentation necessary for determining optimal uptake efficiency for a novel ligand-drug particle.

SUMMARY

In some embodiments, the present disclosure contemplates ligand-drug particles comprising a lipid surface layer and an optional coating layer, at least one ligand molecule exposed on the particle surface or on the lipid surface layer, and at least one drug in the interior of the particle or embedded in the lipid surface layer. The ligand has a particular valency or range of valency (number of ligands per particle) depending on the affinity of the ligand for its receptor on the cell surface of the target cell and depending on the expression level of the receptor in the target cell (expressed herein as the average number of receptors per cell).

In some embodiments, the ligand-drug particle comprises a lipid surface layer, at least one drug in the interior of the particle or embedded in the lipid surface layer, and a ligand specific for a cell surface receptor on a target cell, wherein: (a) the ligand is exposed on the lipid surface layer; (b) the ligand binds to its receptor with an in vitro binding affinity of 0.001 to 1000 nM; (c) the target cell that the particle targets comprises an average on the order of $10^3$ to $10^7$ receptors; and (d) the particle has a ligand valency as described in Table 1 or 2, the ligand valency depending upon the ligand-receptor in vitro binding affinity and the average number of receptors per target cell. In some embodiments, the particle has a ligand valency as follows: (a) a valency of 6-12 where the target cell has an average on the order of $3\times10^6$ receptors per cell; (b) a valency of 10-19 where the target cell has an average on the order of $1\times10^6$ receptors per cell; (c) a valency of 10-20 where the target cell has an average on the order of $9\times10^5$ receptors per cell; (d) a valency of 11-21 where the target cell has an average on the order of $8\times10^5$ receptors per cell; (e) a valency of 12-23 where the target cell has an average on the order of $7\times10^5$ receptors per cell; (f) a valency of 13-25 where the target cell has an average on the order of $6\times10^5$ receptors per cell; (g) a valency of 15-29 where the target cell has an average on the order of $5\times10^5$ receptors per cell; or (h) a valency of 18-36 where the target cell has an average on the order of $4\times10^5$ receptors per cell. In some such embodiments, the ligand-receptor in vitro binding affinity is 0.1 to 10 nM and the particle has a ligand valency as follows: (a) a valency of 8-10 where the target cell has an average on the order of $3\times10^6$ receptors per cell; (b) a valency of 13-16 where the target cell has an average on the order of $9\times10^5$ to $1\times10^6$ receptors per cell; (c) a valency of 14-18 where the target cell has an average on the order of $8\times10^5$ receptors per cell; (d) a valency of 15-19 where the target cell has an average on the order of $7\times10^5$ receptors per cell; (e) a valency of 17-21 where the target cell has an average on the order of $6\times10^5$ receptors per cell; (f) a valency of 19-24 where the target cell has an average on the order of $5\times10^5$ receptors per cell; or (g) a valency of 24-30 where the target cell has an average on the order of $4\times10^5$ receptors per cell.

In further embodiments, the ligand-drug particle has a ligand-receptor in vitro binding affinity is 0.001 to 0.1 nM and the particle has a ligand valency as follows, depending on the number of receptors per cell: (a) a valency of 15-24 where the target cell has an average on the order of $4\times10^5$ to $5\times10^5$ receptors per cell; (b) a valency of 13-19 where the target cell has an average on the order of $5\times10^5$ to $6\times10^5$ receptors per cell; (c) a valency of 12-17 where the target cell has an average on the order of $6\times10^5$ to $7\times10^5$ receptors per cell; (d) a valency of 11-15 where the target cell has an average on the order of $7\times10^5$ to $8\times10^5$ receptors per cell; (e) a valency of 10-14 where the target cell has an average on the order of $8\times10^5$ to $9\times10^5$ receptors per cell; (f) a valency of 10-13 where the target cell has an average on the order of $9\times10^5$ to $1\times10^6$ receptors per cell; or (g) a valency of 6-13 where the target cell has an average on the order of $1\times10^6$ to $3\times10^6$ receptors per cell. In additional embodiments, the ligand-receptor in vitro binding affinity is 0.1 to 10 nM and the particle has a ligand valency as follows: (a) a valency of 19-30 where the target cell has an average on the order of $4\times10^5$ to $5\times10^5$ receptors per cell; (b) valency of 17-24 where the target cell has an average on the order of $5\times10^5$ to $6\times10^5$ receptors per cell; (c) a valency of 15-21 where the target cell has an average on the order of $6\times10^5$ to $7\times10^5$ receptors per cell; (d) a valency of 14-19 where the target cell has an average on the order of $7\times10^5$ to $8\times10^5$ receptors per cell; (d a valency of 13-18 where the target cell has an average on the order of $8\times10^5$ to $9\times10^5$ receptors per cell; (f) a valency of 13-16 where the target cell has an average on the order of $9\times10^5$ to $1\times10^6$ receptors per cell; or (g) a valency of 8-16 where the target cell has an average on the order of $1\times10^6$ to $3\times10^6$ receptors per cell. In yet other embodiments, the ligand-receptor in vitro binding affinity is 10 to 1000 nM and the particle has a ligand valency as follows: (a) valency of 24-36 where the target cell has an average on the order of $4\times10^5$ to $5\times10^5$ receptors per cell; (b) a valency of 21-29 where the target cell has an average on the order of $5\times10^5$ to $6\times10^5$ receptors per cell; (c) a valency of 19-25 where the target cell has an average on the order of $6\times10^5$ to $7\times10^5$ receptors per cell; (d) a valency of 18-23 where the target cell has an average on the order of $7\times10^5$ to $8\times10^5$ receptors per cell; (e) a valency of 16-21 where the target cell has an average on the order of $8\times10^5$ to $9\times10^5$ receptors per cell; (f) a valency of 16-20 where the target cell has an average on the order of $9\times10^5$ to $1\times10^6$ receptors per cell; or (g) a valency of 10-19 where the target cell has an average on the order of $1\times10^6$ to $3\times10^6$ receptors per cell.

In some of the above embodiments, the ligand is an antibody, such as an antigen binding fragment of an antibody, such as an Fv, scFv, Fab', or F(ab')$_2$ fragment. In some of the above embodiments, the lipid surface layer comprises one or more of: phosphatidylcholine, soybean phosphatidylcholine, hydrogenated soybean phosphatidylcholine, egg phosphatidylcholine, dimyristoyl phosphatidylcholine, dipalmitoyl phosphatidylcholine, dioleoyl phosphatidylcholine, distearoyl phosphatidylcholine, palmitoyl oleoyl phosphatidylcholine, phosphatidylethanolamine, distearoyl phosphoethanolamine, dimyristoyl phosphatidylethanolamine, dipalmitoyl phosphatidylethanolamine, dioleoyl phosphatidylethanolamine, phosphatidylserine, dimyristoyl phosphatidylserine, dipalmitoyl phosphatidylserine, dioleoyl phosphatidylserine, phosphatidic acid, phosphatidylinositol, phosphatidylglycerol, dimyristoyl phosphatidylglycerol, dipalmitoyl phosphatidylglycerol, dioleoyl phosphatidylglycerol, distearoyl phosphatidylglycerol, egg sphingomyelin, cholesterol, glycerophospholipids, sphingomyelins, and dioleoyl trimethylammonium propane. In some of the above embodiments, the lipid surface layer is a lipid bilayer, while in other embodiments, it is a lipid monolayer. In any of the above embodiments, the at least one drug may comprise a polar, small molecule compound located in an aqueous space at the interior of the particle. In some embodiments, the at least one drug comprises a hydrophobic, small molecule compound embedded in the lipid surface layer. And the particle may contain one drug compound, two drug compounds, or more depending on its utility. In some embodiments, the particle also contains further excipients for solubilizing or protecting the drug compound or for maintaining pH, for example.

In some embodiments, the ligand is an antibody and the antibody ligand is selected from: abciximab, adalimumab, adecatumumab, alacizumab, alemtuzumab, alirocumab, aprutumab, atezolizumab, avelumab, basiliximab, batuzumab, belimumab, bemarituzumab, benralizumab, bevacizumab, bezlotoxumab, blinatumomab, brentuximab, brodalumab, brolucizumab, canakinumab, capromab, catumaxomab, certolizumab, cetuximab, citatuzumab, cixutumumab, daclizumab, dalotuzumab, daratumumab, denosumab, depatuxizumab, dinutuximab, duligotuzumab, dupilumab, durvalumab, eculizumab, edrecolomab, elgemtumab, elotuzumab, emibetuzumab, emicizumab, ertumaxomab, evolocumab, faricimab, fibatuzumab, figitumumab, futuximab, ganitumab, gemtuzumab, golimumab, guselkumab, ibritumomab, icrucumab, idarucizumab, ifabotuzumab, imgatuzumab, infliximab, inotuzumab, ipilimumab, istiratumab, ixekizumab, lapritumab, losatuxizumab, lumretuzumab, margetuximab, mepolizumab, modotuximab, natalizumab, necitumumab, nimotuzumab, nivolumab, obiltoxaximab, obinutuzumab, ocrelizumab, ofatumumab, olaratumab, omalizumab, oportuzumab, palivizumab, panitumumab, patritumab, pembrolizumab, pertuzumab, ramucirumab, ranibizumab, raxibacumab, reslizumab, rinucumab, rituximab, robatumumab, sarilumab, secukinumab, seribantumab, siltuximab, solitomab, tanibirumab, telisotuzumab, teprotumumab, timiguanzumab, tocilizumab, tomuzotuximab, trastuzumab, tucotuzumab, ustekinumab, varisacumab, vedolizumab, xentuzumab, zalutumumab, zatuximab, and zenocutuzumab, and antigen binding fragments thereof, such as Fv, scFv, Fab', or F(ab')2 fragments of the above-listed antibodies.

In some embodiments, the target cell is a tumor cell, an infectious cell, or an immune cell. In some embodiments, the particle further comprises a coating comprising polyethylene glycol (PEG).

Also contemplated herein are ligand-drug particles that comprise two different ligands, specific for two different receptors on a target cell. Such ligand-drug particles may comprise a lipid surface layer, at least one drug in the interior of the particle or embedded in the lipid surface layer, and two ligands specific for two different cell surface receptors on a target cell, wherein the ligands are exposed on the lipid surface layer; the ligands bind to their receptors with in vitro binding affinity of 0.1 to 100 nM; the target cell that the particle targets comprises an average on the order of $10^3$ to $10^7$ of each receptor; and the particle has a ligand valency for each of the two ligands as described in Table 3, the ligand valency depending upon the ligand-receptor in vitro binding affinity or each receptor-ligand pair, the average number of each receptor per target cell, and whether ligand-receptor binding is additive or synergistic. In some embodiments, the particle has a ligand valency for each of the ligands as follows: (a) a valency of 13-17 where each receptor is highly expressed by the target cell and where binding of the two receptors by the two ligands is additive; (b) valency of 9-13 where each receptor is highly expressed by the target cell and where binding of the two receptors by the two ligands is synergistic; (c) a valency of 13-17 where one receptor is highly expressed by the target cell and the other receptor is moderately expressed, and where binding of the two receptors by the two ligands is additive; (d) a valency of 7-10 where one receptor is highly expressed by the target cell and the other receptor is moderately expressed, and where binding of the two receptors by the two ligands is synergistic; (e) a valency of 15-21 where each receptor is moderately expressed by the target cell and where binding of the two receptors by the two ligands is additive; or (f) a valency of 11-15 where each receptor is moderately expressed by the target cell and where binding of the two receptors by the two ligands is synergistic.

In some embodiments, the dual-ligand particle has a ligand valency for each ligand as follows: (a) a valency of 17-21 where the in vitro binding affinity for each ligand-receptor pair is on the order of 100 nM and binding is additive; (b) a valency of 16-20 where the in vitro binding affinity for one ligand-receptor pair is on the order of 100 nM for the second ligand-receptor pair is on the order of 10 nM and binding is additive; (c) a valency of 16-19 where the in vitro binding affinity for one ligand-receptor pair is on the order of 100 nM for the second ligand-receptor pair is on the order of 1 nM and binding is additive; (d) a valency of 15-19 where the in vitro binding affinity for one ligand-receptor pair is on the order of 100 nM for the second ligand-receptor pair is on the order of 0.1 nM and binding is additive; (e) a valency of 16-19 where the in vitro binding affinity for each ligand-receptor pair is on the order of 10 nM and binding is additive; (f) a valency of 15-18 where the in vitro binding affinity for one ligand-receptor pair is on the order of 10 nM for the second ligand-receptor pair is on the order of 1 nM and binding is additive; (g) a valency of 14-17 where the in vitro binding affinity for one ligand-receptor pair is on the order of 10 nM for the second ligand-receptor pair is on the order of 0.1 nM and binding is additive; (h) a valency of 14-17 where the in vitro binding affinity for each ligand-receptor pair is on the order of 1 nM and binding is additive; (i) a valency of 13-16 where the in vitro binding affinity for one ligand-receptor pair is on the order of 1 nM for the second ligand-receptor pair is on the order of 0.1 nM and binding is additive; (j) a valency of 13-15 where the in vitro binding affinity for each ligand-receptor pair is on the order of 0.1 nM and binding is additive; (k) a valency of 10-15 where the in vitro binding affinity for each ligand-receptor pair is on the order of 100 nM and binding is synergistic; (l) a valency of 10-15 where the in vitro binding affinity for one ligand-receptor pair is on the order of 100 nM for the second ligand-receptor pair is on the order of 10 nM and binding is synergistic; (m) a valency of 10-15 where the in vitro binding affinity for one ligand-receptor pair is on the order of 100 nM for the second ligand-receptor pair is on the order of 1 nM and binding is synergistic; (n) a valency of 10-15 where the in vitro binding affinity for one ligand-receptor pair is on the order of 100 nM for the second ligand-receptor pair is on the order of 0.1 nM and binding is synergistic; (o) a valency of 9-13 where the in vitro binding affinity for each ligand-receptor pair is on the order of 10 nM and binding is synergistic; (p) a valency of 9-13 where the in vitro binding affinity for one ligand-receptor pair is on the order of 10 nM for the second ligand-receptor pair is on the order of 1 nM and binding is synergistic; (q) a valency of 9-13 where the in vitro binding affinity for one ligand-receptor pair is on the order of 10 nM for the second ligand-receptor pair is on the order of 0.1 nM and binding is synergistic; (r) a valency of 8-12 where the in vitro binding affinity for each ligand-receptor pair is on the order of 1 nM and binding is synergistic; (s) a valency of 8-12 where the in vitro binding affinity for one ligand-receptor pair is on the order of 1 nM for the second ligand-receptor pair is on the order of 0.1 nM and binding is synergistic; or (t) a valency of 7-11 where the in vitro binding affinity for each ligand-receptor pair is on the order of 0.1 nM and binding is synergistic.

In some embodiments, in a dual-ligand particle, at least one ligand is an antibody, or both ligands are antibodies. In some embodiments, at least one ligand is an antigen binding fragment of an antibody, or both ligands are antigen binding fragments of antibodies, such as an Fv, scFv, Fab', or F(ab')$_2$ fragment.

In some of the above embodiments, the lipid surface layer comprises one or more of phosphatidylcholine, soybean phosphatidylcholine, hydrogenated soybean phosphatidylcholine, egg phosphatidylcholine, dimyristoyl phosphatidylcholine, dipalmitoyl phosphatidylcholine, dioleoyl phosphatidylcholine, distearoyl phosphatidylcholine, palmitoyl oleoyl phosphatidylcholine, phosphatidylethanolamine, distearoyl phosphoethanolamine, dimyristoyl phosphatidylethanolamine, dipalmitoyl phosphatidylethanolamine, dioleoyl phosphatidylethanolamine, phosphatidylserine, dimyristoyl phosphatidylserine, dipalmitoyl phosphatidylserine, dioleoyl phosphatidylserine, phosphatidic acid, phosphatidylinositol, phosphatidylglycerol, dimyristoyl phosphatidylglycerol, dipalmitoyl phosphatidylglycerol, dioleoyl phosphatidylglycerol, distearoyl phosphatidylglycerol, egg sphingomyelin, cholesterol, glycerophospholipids, sphingomyelins, and dioleoyl trimethylammonium propane. In some of the above embodiments, the lipid surface layer is a lipid bilayer; in others it is a lipid monolayer. In any of the above embodiments, the at least one drug may comprise a polar, small molecule compound located in an aqueous space at the interior of the particle. In some embodiments, the at least one drug comprises a hydrophobic, small molecule compound embedded in the lipid surface layer. And the particle may contain one drug compound, two drug compounds, or more depending on its utility. In some embodiments, the particle also contains further excipients for solubilizing or protecting the drug compound or for maintaining pH, for example.

In some embodiments, an antibody ligand is selected from: abciximab, adalimumab, adecatumumab, alacizumab, alemtuzumab, alirocumab, aprutumab, atezolizumab, avelumab, basiliximab, batuzumab, belimumab, bemarituzumab, benralizumab, bevacizumab, bezlotoxumab, blinatumomab, brentuximab, brodalumab, brolucizumab, canakinumab, capromab, catumaxomab, certolizumab, cetuximab, citatuzumab, cixutumumab, daclizumab, dalotuzumab, daratumumab, denosumab, depatuxizumab, dinutuximab, duligotuzumab, dupilumab, durvalumab, eculizumab, edrecolomab, elgemtumab, elotuzumab, emibetuzumab, emicizumab, ertumaxomab, evolocumab, faricimab, fibatuzumab, figitumumab, futuximab, ganitumab, gemtuzumab, golimumab, guselkumab, ibritumomab, icrucumab, idarucizumab, ifabotuzumab, imgatuzumab, infliximab, inotuzumab, ipilimumab, istiratumab, ixekizumab, lapritiximab, losatuxizumab, lumretuzumab, margetuximab, mepolizumab, modotuximab, natalizumab, necitumumab, nimotuzumab, nivolumab, obiltoxaximab, obinutuzumab, ocrelizumab, ofatumumab, olaratumab, omalizumab, oportuzumab, palivizumab, panitumumab, patritumab, pembrolizumab, pertuzumab, ramucirumab, ranibizumab, raxibacumab, reslizumab, rinucumab, rituximab, robatumumab, sarilumab, secukinumab, seribantumab, siltuximab, solitomab, tanibirumab, telisotuzumab, teprotumumab, timigutuzumab, tocilizumab, tomuzotuximab, trastuzumab, tucotuzumab, ustekinumab, varisacumab, vedolizumab, xentuzumab, zalutumumab, zatuximab, and zenocutuzumab, and binding fragments thereof, such as Fv, scFv, Fab', or F(ab')$_2$ fragments of the above-listed antibodies.

In some embodiments, the target cell is a tumor cell, an infectious cell, or an immune cell. In some embodiments, the particle further comprises a coating comprising PEG.

Any of the particles contemplated herein may be 10-500 nm, 50-150 nm, 70-120 nm, 80-110 nm, 90-110 nm, 70 nm, 75 nm, 80 nm, 85 nm, 90 nm, 95 nm, 100 nm, 105 nm, 110 nm, 115 nm, or 120 nm in diameter.

This disclosure also contemplates a system for determining ligand valency for a ligand-drug particle, wherein the particle comprises a lipid surface layer, at least one drug in the interior of the particle or embedded in the lipid surface layer, and a ligand specific for a receptor on a target cell, the ligand exposed on the lipid surface layer, the system comprising software capable of determining ligand valency from in vitro ligand-receptor dissociation constant and average number of receptors per target cell according to a crosslink multivalent binding model. The disclosure further contemplates a system for determining ligand valency for a ligand-drug particle, wherein the particle comprises a lipid surface layer, at least one drug in the interior of the particle or embedded in the lipid surface layer, and two ligands each specific for a receptor on a target cell, the ligands exposed on the lipid surface layer, the system comprising software capable of determining ligand valency from in vitro ligand-receptor dissociation constants for each ligand-receptor pair and average number of each receptor per target cell and either additive or synergistic binding according to a crosslink multivalent binding model.

BRIEF DESCRIPTION OF THE DRAWINGS

In FIG. 2A, a free nanoparticle binds to a single receptor on the cell surface. Subsequently, as shown in FIG. 2B at left, the nanoparticle binds to a second receptor, and then to a third, as shown in FIG. 2B at right. Simultaneous crosslink multivalent binding continues until the nanoparticle reaches f bounds. It is assumed that the nanoparticle can only form monovalent bounds with single receptors and receptor dimers. The crosslink association and dissociation constants are assumed to be constant for successive bindings.

FIGS. 5A and 5B provide different views of a surface plot of nanoparticle cell association ($C_{Beq}$, nanoparticles/cell) as a function of valence and effective valence (ligands/nanoparticle) in high receptor expressing cells ($R_T=10^6$ #/cell). Values were evaluated in Mathcad® with the additional parameters: $10^6$ nanoparticles per cell in solution ($L_o$), 100 nM equilibrium constant ($K_D$), $1/(70*10^3$ #/cells) crosslinking equilibrium constant ($K_x$). It is assumed that there are no nanoparticle and receptor depletion effects, and since f≤v, if v<f then v=f.

As shown in FIG. 12A, Liposome+Ligand-PEG-DSPE produce a Ligand-Liposome. In FIG. 12B, Liposome+Mal-PEG-DSPE first yield Mal-Liposome, which is then subject to a further reaction to yield Ligand-Liposome (where Mal stands for maleimide).

As shown in FIG. 13A, Liposome+Mal-PEG-DSPE first yields Mal-Liposome, and then Mal is replaced by a Fab' ligand (cetuximab Fab') to yield Fab'-Liposome. In FIG. 13B a second scFv ligand (F5 scFv) is added to the liposome.

FIG. 14A shows a High Receptor Expression Model ($K_D$=0.1 nM; $R_T$=4*10^5-3*10^6 receptors/cell). FIG. 14B shows a High Receptor Expression Model ($K_D$=1 nM; $R_T$=4*10^5-3*10^6 receptors/cell). FIG. 14C shows a High Receptor Expression Model ($K_D$=10 nM; $R_T$=4*10^5-3*10^6 receptors/cell). FIG. 14D shows a High Receptor Expression Model ($K_D$=100 nM; $R_T$=4*10^5-3*10^6 receptors/cell). FIG. 14E shows a High Receptor Expression Model ($K_D$=0.001-1000 nM; $R_T$=10^6 receptors/cell). FIG. 14F shows a High Receptor Expression Model ($K_D$=0.001-1000 nM; $R_T$=5*10^5 receptors/cell).

FIG. 15A shows a model where the $K_D$s of the receptor-ligand interactions are both 0.1 nM under additive binding. FIG. 15B shows a model where the $K_D$s of the receptor-ligand interactions are both 0.1 nM under synergistic binding. FIG. 15C shows a model where the $K_D$s of the receptor-ligand interactions are both 1 nM under additive binding. FIG. 15D shows a model where the $K_D$s of the receptor-ligand interactions are both 01 nM under synergistic binding. $C_{BeqHH}$ indicates that the cell highly expresses both receptors while $C_{BeqMM}$ indicates that the cell moderately expresses both receptors and $C_{BeqHM}$ indicates that the cell highly expresses one receptor and moderately expresses the other. The $C_{BeqH}$ and $C_{BeqM}$ curves show cell association for a corresponding highly expressed and moderately expressed single ligand.

DESCRIPTION OF THE EMBODIMENTS

Definitions

Figure 1:
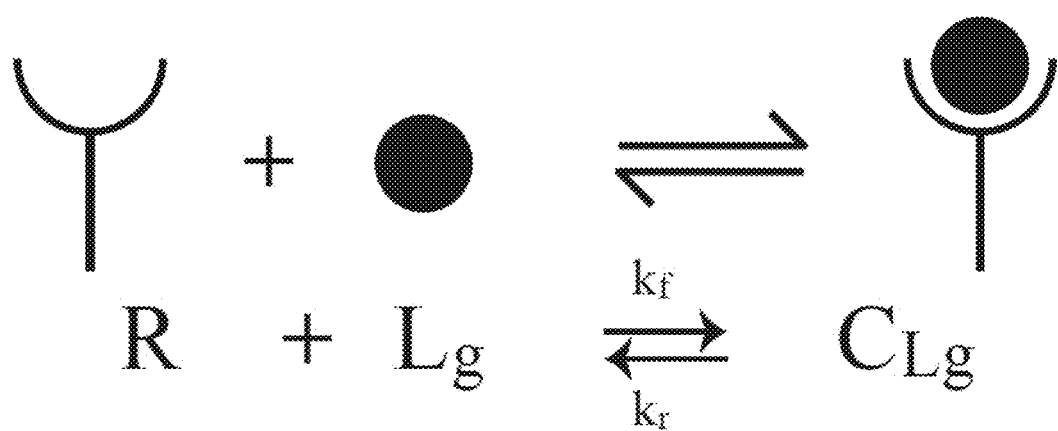
FIG. 1 provides a schematic of monovalent receptor-ligand binding. Ligand ($L_g$) binds to receptor (R) to form a ligand/receptor complex ($C_{Lg}$).

The section headings used herein are for organizational purposes only and are not to be construed as limiting the subject matter described. All references cited herein, including patent applications and publications, are incorporated herein by reference in their entireties for any purpose.

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

In this application, the use of "or" means "and/or" unless stated otherwise. In the context of a multiple dependent claim, the use of "or" refers back to more than one preceding independent or dependent claim in the alternative only. Also, terms such as "element" or "component" encompass both elements and components comprising one unit and elements and components that comprise more than one subunit unless specifically stated otherwise.

As described herein, any concentration range, percentage range, ratio range or integer range is to be understood to include the value of any integer within the recited range and, when appropriate, fractions thereof (such as one tenth and one hundredth of an integer), unless otherwise indicated.

Units, prefixes, and symbols are denoted in their Système International de Unites (SI) accepted form. Numeric ranges are inclusive of the numbers defining the range. Measured values are understood to be approximate, taking into account significant digits and the error associated with the measurement.

The headings provided herein are not limitations of the various aspects of the disclosure, which can be had by reference to the specification as a whole. Accordingly, the terms defined immediately below are more fully defined by reference to the specification in its entirety.

As utilized in accordance with the present disclosure, the following terms, unless otherwise indicated, shall be understood to have the following meanings:

The term "consisting essentially of" when referring to a mixture of ingredients or a ligand-drug particle herein indicates that, while ingredients other than those expressly listed may be present, such ingredients are found only in trace amounts or in amounts otherwise low enough that the fundamental characteristics of the particle including its cellular uptake properties.

A "conjugate particle" or "ligand-drug particle" or "particle" herein refers to a composition, generally in the form of an organized particle, comprising one or more lipids, at least one ligand, and at least one drug. In some embodiments, a "ligand drug particle" is a liposomal particle comprising at least one lipid surface layer into which at least one ligand may be incorporated or to which a ligand may be attached. The at least one drug may be incorporated in the interior of a particle, or embedded in a lipid surface layer, or otherwise coated with lipid particles, or may otherwise be attached to the surface of a particle. A ligand may be attached to the surface of a particle or interspersed between lipids of a lipid bilayer so that it is sufficiently exposed on the surface of the particle to interact with its intended receptor on a target cell. A "particle" may have any shape, but in the case of a lipid-coated particle, is often roughly spherical.

In some embodiments, a particle may be a "liposome" particle. A liposome comprises a particle with an aqueous interior that is surrounded by a lipid surface layer. The lipid surface layer may be a lipid bilayer or lipid monolayer depending upon which types of lipids are present.

A "ligand" herein refers to a molecule located in a ligand-drug particle that binds to a receptor molecule on the surface of a target cell. A ligand herein is generally a protein, such as an antibody. In some embodiments, a ligand is an antibody, such as an antigen binding fragment of an antibody. A "ligand" herein may merely function to target a ligand-drug particle to a target cell, but in some embodiments, may also itself have biological or therapeutic activity.

A "drug" as used in the context of a ligand drug particle herein, includes any chemical compound that has a therapeutic effect on a disease or condition or that can be used as a diagnostic compound, for example inside an animal cell. Drugs include small organic molecules as well as macromolecular therapeutics such as nucleic acid and protein therapeutics. Some drugs are hydrophilic, and thus may be located in an aqueous compartment in a particle such as in the interior, while some drugs are hydrophobic and may be found surrounded by lipids or other hydrophobic molecules, for example, in a lipid surface layer.

A "target cell" herein refers to a cell to which a ligand-drug particle is intended to bind, such as a tumor cell or an infectious cell or an inflammatory cell. In some embodiments, for example, a ligand on a ligand-drug particle may bind to a component of a target cell such as a receptor protein, allowing the contents of the particle to enter the cell through endocytosis.

In referring to ligand-drug particles herein, the term "valence" refers to the number of ligands per particle. The "effective valence" refers to the number of ligands per particle that are assumed to be able to bind to a target cell. An effective valence might differ from the valence, for instance, due to steric hindrance or other limitations of a particular ligand's ability to bind to its target.

When referring to a numerical quantity such as the number of receptors per cell or a dissociation constant, herein, the term "on the order of" followed by a number means that the actual reported or measured quantity rounds up or down to the numerical quantity provided. For example, $8 \times 10^5$ and $2 \times 10^6$ are each on the order of $10^6$ or $1 \times 10^6$, and 20 nM and 8 nM are each on the order of 10 nM.

As used herein to refer to the binding of two molecules, a "binding affinity" or "equilibrium dissociation constant" or "dissociation constant" or "$K_D$" are used interchangeably. The binding is generally measured in vitro such as in aqueous solution or in cell culture unless specified otherwise. The dissocation constant of a binding pair can be assessed using various scientific and surface-based methods including surface plasmon resonance (SPR), biolayer interferometry (BLI), enzyme linked immunosorbent assays (ELISA), affinity capillary electrophoresis (ACE), electrophoretic mobility shift assay (EMSA), and microarray-based platform.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

The term "antibody" as used herein refers to a molecule comprising at least complementarity-determining region (CDR) 1, CDR2, and CDR3 of a heavy chain and at least CDR1, CDR2, and CDR3 of a light chain, wherein the molecule is capable of binding to antigen. The term "antibody" includes, but is not limited to, fragments that are capable of binding antigen (i.e., "antigen binding fragments"), such as Fv, single-chain Fv (scFv), Fab, Fab', and (Fab')$_2$. In some embodiments, the antibody is an Fab' fragment. In some embodiments, an antibody comprises a heavy chain variable region and a light chain variable region. In some embodiments, an antibody comprises at least one heavy chain comprising a heavy chain variable region and at least a portion of a heavy chain constant region, and at least one light chain comprising a light chain variable region and at least a portion of a light chain constant region. In some embodiments, the antibody comprises a full length light chain (i.e. a complete variable region and a complete constant region). In some embodiments, the antibody comprises a full length heavy chain. In some embodiments, the antibody comprises both a full length light chain and a full length heavy chain. As used herein, a single-chain Fv (scFv), or any other antibody that comprises, for example, a single polypeptide chain comprising all six CDRs (three heavy chain CDRs and three light chain CDRs) is considered to have a heavy chain and a light chain. In some such single-chain embodiments, the heavy chain is the region of the antibody that comprises the three heavy chain CDRs and the light chain in the region of the antibody that comprises the three light chain CDRs.

Design of Ligand-drug Particles and Cellular Uptake of Particles

Ligand-drug particles herein may, for example, comprise liposomal particles. Liposomal particles are artificial particles that typically comprise an aqueous interior surrounded by a lipid surface layer such as a lipid bilayer or lipid monolayer. The aqueous interior is favorable to entrap water-soluble drug agents while lipid-soluble hydrophobic drug agents can be partitioned into the lipid bilayer. Liposomes may also comprise polyethylene glycol (PEG), for example, to provide a protective layer. Ligands may be incorporated into the lipid surface layer, for example, if they are hydrophobic. Excipients may also be included in the particles, for example, to help stabilize or solubilize a drug in the particle or to help maintain a particular pH.

Liposomes as a drug delivery system may alter the pharmacokinetic profile of the drug encapsulated to the profile of liposomal carrier. Some chemotherapeutic drugs that may be encapsulated in the aqueous core or incorporated in the lipid surface layer of a liposome, for instance, include daunomycin, doxorubicin (e.g., Doxil®), cisplatin, vinorelbine, topotecan, AraC, vinblastine, vincristine, PALA, methotrexate, paclitaxel, and irinotecan. Doxil® (Janssen Products, Johnson & Johnson) is a sterically stabilized liposome-encapsulated form of doxorubicin used for the treatment of ovarian cancer, multiple myeloma, and Kaposi's sarcoma, for example. The surface of the Doxil® particle, for example, is pegylated.

Ligand-drug particles herein, such as liposomes, may be taken up by target cells either passively or actively. For example, solid tumors are supported by a discontinuous microvasculature and may have pore sizes varying between 100-780 nm, which allows the passage of large molecules and nanoparticles such as liposomes. The accumulation of large molecules and liposomes in tumors, the result of a leaky microvasculature and impaired lymphatics supporting the tumor area, is a phenomenon known as the enhanced permeability and retention effect (EPR). EPR is limited to pathological sites with affected and leaky vasculature such as solid tumors, sites of inflammations, and infarcted areas. Large molecules or particles 10-500 nm like liposomes can extravasate through the endothelium and localize in the tumor interstitium. Because free cytotoxic agents are small, they are localized in the tumor rapidly, but may also be cleared rapidly, resulting in considerable lower tumor AUC for free drug than liposomal drugs. Despite the increased in tumor accumulation, distribution of liposomes within the tumor interstitium is still limited, resulting from high interstitial pressure and a large interstitial space. Liposomes in the interstitium space are not usually found within tumor cells but are found inside tumor macrophages. Ideally once in the interstitium space, drug leaks at sufficient rate to become bioavailable at the tumor. Drug may leak due to instabilities from conditions in the interstitium, plasma protein, enzymes, or liposomal degradation by macrophages. Released drug can act on neighboring cells via a bystander effect. Passive targeting is limited to pathological sites susceptible to the EPR. In addition, it relies on the diffusion of drugs from the liposomes into the cells of interest. As a result, the delivery of drugs that are prone to degradation from the plasma environment may not be ideal for delivery.

Ligands that induce receptor-mediated endocytosis upon binding can be engineered onto liposomes for the delivery of drugs intracellularly to tumors. Liposomes delivered for solid tumors, for example, may first benefit from passive targeting, accumulating in the tumor interstitium due to the EPR. But ligand targeting also allows for uptake via endocytosis into target cells. Ligand targeting also allows for delivery to other types of target cells such as endothelial cells, infectious cells, and the like.

All eukaryotic cells exhibit some form of endocytosis to maintain homeostasis, at the cellular level by recovering protein and lipid components and at the organismal level by controlling activities including transmission of neuronal, metabolic, and proliferative signals, nutrient uptake, and defense preparation. Multiple types of endocytosis exist including phagocytosis, clathrin-independent endocytosis, and clathrin-dependent endocytosis. The endocytosis of many signaling receptors is stimulated by ligand-induced activation, with virtually every signaling receptor family undergoing clathrin-dependent endocytosis. To ensure the internalization of lipid-containing particles into targeted cells, attached high affinity ligands may internalize to induce receptor-mediated clathrin-dependent endocytosis upon binding.

Endocytosis is typically initiated by the binding of transmembrane receptors and their extracellular ligands into cytoplasmic vesicles that are pinched off from the plasma membrane. Receptor-ligand complexes are recruited to clathrin-coated pits and invaginate inwards to form clathrin-coated vesicles. Endocytosed vesicles fuse with early endosomes, and subsequently receptor-ligand complexes can dissociate and traffic to the recycling compartment containing Rab 11 or to the late endosomal compartment containing Rab7. Many receptor-ligand complexes dissociate in the early endosomes due to the slightly acidic pH (pH ~6.0-6.8). While receptors and ligands in recycling endosomes are returned to the plasma membrane, fusion of late endosomes with lysosomes (pH ~4.0-5.5) carrying proteolytic enzymes results in cargo degradation.

Endosomal trafficking is controlled by several Rab proteins, small guanosine triphosphate-binding proteins. The Rab family is the largest branch of the Ras superfamily with more than 60 members found in mammalian cells. Rab proteins reside in particular types of endosomes and function by recruiting specific effector proteins. Rab proteins distinguish certain intracellular compartments and are involved in vesicle budding, vesicular movement, membrane tethering, membrane docking, and membrane fusion. Rab7 is primarily localized on the late endosomes and has been shown to be essential for lysosomes biogenesis. Rab11 is primarily localized on the recycling endosomes and has been extensively studied for its involvement in transferrin receptor recycling. Tagged Rab proteins as markers are useful for the isolation and localization of nanoparticles within the late endosomes and the recycling endosomes.

Exemplary Components of Liposomal Ligand-drug Particles

In some embodiments, herein, the ligand-drug particle is a liposome. In some embodiments, liposomes may be, for example, 10 nm to 500 nm in diameter, such as 50-150 nm in diameter, such as 70-120 nm, 80-110 nm, or 90-110 nm, or 70, 75, 80, 85, 90, 95, 100, 105, 110, 115, or 120 nm. In some embodiments, liposomes are charge-neutral. In some embodiments, liposomes comprise a lipid monolayer while in others they comprise a lipid bilayer as a lipid surface layer. In some embodiments, liposomes comprise a lipid surface layer comprising both one or more phospholipids as well as PEG and/or cholesterol. In some embodiments, the liposome comprises a PEG coating. In others, it does not. In some embodiments, phospholipids may be neutral or charged, and may be selected from phosphatidylcholine, soybean phosphatidylcholine, hydrogenated soybean phosphatidylcholine, egg phosphatidylcholine, dimyristoyl phosphatidylcholine, dipalmitoyl phosphatidylcholine, dioleoyl phosphatidylcholine, distearoyl phosphatidylcholine, palmitoyl oleoyl phosphatidylcholine, phosphatidylethanolamine, distearoyl phosphoethanolamine, dimyristoyl phosphatidylethanolamine, dipalmitoyl phosphatidylethanolamine, dioleoyl phosphatidylethanolamine, phosphatidylserine, dimyristoyl phosphatidylserine, dipalmitoyl phosphatidylserine, dioleoyl phosphatidylserine, phosphatidic acid, phosphatidylinositol, phosphatidylglycerol, dimyristoyl phosphatidylglycerol, dipalmitoyl phosphatidylglycerol, dioleoyl phosphatidylglycerol, distearoyl phosphatidylglycerol, egg sphingomyelin, cholesterol, glycerophospholipids, sphingomyelins, and dioleoyl trimethylammonium propane. In some embodiments, for example, they may be selected from phosphatidyl choline, phosphatidylserine, phosphatidylinositol, phosphatidylethanolamine, sphingomyelin, HSPC (hydrogenated soybean phosphatidylcholine), DSPC (1,2-distearoyl-sn-glycero-3-phosphocholine), DSPE (1,2-distearoyl-sn-glycero-3-phosphoethanolamine), DPPC (1,2-dipalmitoyl-sn-glycero-3-phosphocholine), and PLPC (1-palmitoyl-2-lauroyl-sn-glycero-3-phosphocholine). In some embodiments, the lipid surface layer may comprise one or more lipids or carriers such as phosphatidylcholine, soybean phosphatidylcholine, hydrogenated soybean phosphatidylcholine, egg phosphatidylcholine, dimyristoyl phosphatidylcholine, dipalmitoyl phosphatidylcholine, dioleoyl phosphatidylcholine, distearoyl phosphatidylcholine, palmitoyl oleoyl phosphatidylcholine, phosphatidylethanolamine, distearoyl phosphoethanolamine, dimyristoyl phosphatidylethanolamine, dipalmitoyl phosphatidylethanolamine, dioleoyl phosphatidylethanolamine, phosphatidylserine, dimyristoyl phosphatidylserine, dipalmitoyl phosphatidylserine, dioleoyl phosphatidylserine, phosphatidic acid, phosphatidylinositol, phosphatidylglycerol, dimyristoyl phosphatidylglycerol, dipalmitoyl phosphatidylglycerol, dioleoyl phosphatidylglycerol, distearoyl phosphatidylglycerol, egg sphingomyelin, cholesterol, glycerophospholipids, sphingomyelins, dioleoyl trimethylammonium propane, polyethylene glycol (PEG), and albumin, among others.

In embodiments herein, drugs that may be incorporated into the aqueous interior or lipid surface layer of a liposomal particle include, for example, small molecule chemotherapy agents, kinase inhibitors, nucleic acid-based therapeutics, peptide therapeutics and the like. Drugs may also include diagnostic agents, for example, fluorescent or radio-labeled molecules. In some embodiments, liposomal particles may encapsulate, for example $1-5 \times 10^4$ drug molecules per liposome, such as $1.5-4 \times 10^4$ drug molecules, or $2-3 \times 10^4$ drug molecules. In some embodiments, a drug is enclosed in the interior space or is embedded in the lipid surface layer of a ligand-drug particle comprising a ligand, and is not covalently attached to a ligand or otherwise covalently attached to the surface of the particle or exposed on the surface of the particle.

In embodiments herein, ligands exposed on the lipid surface layer of the particle may be covalently attached to another surface molecule or may be otherwise associated on the surface of the particle, for example, through attachment to a transmembrane peptide domain that spans a lipid bilayer. In some embodiments, the ligand is an antibody. In some embodiments, the ligand is an antigen binding fragment of an antibody. In some embodiments, the antigen binding fragment is an Fv, scFv, Fab, Fab', or (Fab')$_2$ fragment. In some embodiments, it is an scFv or Fab' fragment.

In some embodiments, the antibody may be selected from abciximab, adalimumab, adecatumumab, alacizumab, alemtuzumab, alirocumab, aprutumab, atezolizumab, avelumab, basiliximab, batuzumab, belimumab, bemarituzumab, benralizumab, bevacizumab, bezlotoxumab, blinatumomab, brentuximab, brodalumab, brolucizumab, canakinumab, capromab, catumaxomab, certolizumab, cetuximab, citatuzumab, cixutumumab, daclizumab, dalotuzumab, daratumumab, denosumab, depatuxizumab, dinutuximab, duligotuzumab, dupilumab, durvalumab, eculizumab, edrecolomab, elgemtumab, elotuzumab, emibetuzumab, emicizumab, ertumaxomab, evolocumab, faricimab, fibatuzumab, figitumumab, futuximab, ganitumab, gemtuzumab, golimumab, guselkumab, ibritumomab, icrucumab, idarucizumab, ifabotuzumab, imgatuzumab, infliximab, inotuzumab, ipilimumab, istiratumab, ixekizumab, laprituximab, losatuxizumab, lumretuzumab, margetuximab, mepolizumab, modotuximab, natalizumab, necitumumab, nimotuzumab, nivolumab, obiltoxaximab, obinutuzumab, ocrelizumab, ofatumumab, olaratumab, omalizumab, oportuzumab, palivizumab, panitumumab, patritumab, pembrolizumab, pertuzumab, ramucirumab, ranibizumab, raxibacumab, reslizumab, rinucumab, rituximab, robatumumab, sarilumab, secukinumab, seribantumab, siltuximab, solitomab, tanibirumab, telisotuzumab, teprotumumab, timigutuzumab, tocilizumab, tomuzotuximab, trastuzumab, tucotuzumab, ustekinumab, varisacumab, vedolizumab, xentuzumab, zalutumumab, zatuximab, and zenocutuzumab, and antigen binding fragments of the above-listed antibodies. In some embodiments, a ligand may be selected from: Orthoclone® OKT3 (muromonab-CD3), ReoPro® (abciximab), Zenapax® (daclizumab), Rituxan/Mabthera® (rituximab), Simulect® (basiliximab), Remicade® (infliximab), Synagis® (palivizumab), Herceptin® (trastuzumab), Campath® (alemtuzumab), Humira® (adalimumab), Raptiva® (efalizumab), Zevalin® (ibritumomab tiuxetan), Bexxar® (tositumomab), Avastin® (bevacizumab), Erbitux® (cetuximab), Xolair® (omalizumab), Tysabri® (natalizumab), Vectibix® (panitumumab), Lucentis® (ranibizumab), Soliris® (eculizumab), Cimzia® (certolizumab pegol), Ilaris® (canakinumab), Simponi® (golimumab), Arzerra® (ofatumumab), Prolia/Xgeva® (denosumab), Actemra/RoActemra® (tocilizumab/atlizumab), Benlysta® (belimumab), Yervoy® (ipilimumab), Stelara® (ustekinumab), Opdivo® (nivolumab), Keytruda® (Pembrolizumab), Entyvio® (vedolizumab), and Darzalex® (daratumumab). In some embodiments, the ligand may be derived from the antibody component of Mylotarg® (gemtuzumab ozogamicin), Adcetris® (brentuximab vedotin), or Kadcyla® (trastuzumab emtansine).

In some embodiments, the ligand may be selected from: 3f8, 8h9, abagovomab, abciximab, abituzumab, abrezekimab, abrilumab, actoxumab, adalimumab, adecatumumab, adrenomedullin, aducanumab, afasevikumab, afelimomab, afutuzumab, alacizumab, alemtuzumab, alirocumab, altumomab, amatuximab, amphiregulin, anatumomab, andecaliximab, anetumab, angiopoietin, anifrolumab, anrukinzumab, anti-apoptotic survival factor, apolizumab, aprutumab, arcitumomab, artemin, ascrinvacumab, aselizumab, atezolizumab, atidortoxumab, atinumab, atorolimumab, autocrine motility factor, avelumab, azintuxizumab, bapineuzumab, basiliximab, bavituximab, bcd-100, bectumomab, begelomab, belantamab, belimumab, bemarituzumab, benralizumab, berlimatoxumab, bersanlimab, bertilimumab, besilesomab, betacellulin, bevacizumab, bezlotoxumab, biciromab, bimagrumab, bimekizumab, birtamimab, bivatuzumab, bivv009, bleselumab, blinatumomab, blontuvetmab, blosozumab, bococizumab, bone morphogenetic proteins, brazikumab, brentuximab, briakinumab, brodalumab, brolucizumab, brontictuzumab, burosumab, cabiralizumab, camidanlumab, camrelizumab, canakinumab, cantuzumab, caplacizumab, capromab, carlumab, carotuximab, catumaxomab, cbr96, cedelizumab, cemiplimab, cergutuzumab, certolizumab, cetrelimab, cetuximab, cibisatamab, ciliary neurotrophic factor family, citatuzumab, cixutumumab, clazakizumab, clenoliximab, clivatuzumab, codrituzumab, cofetuzumab, colony-stimulating factors, coltuximab, conatumumab, concizumab, cosfroviximab, cr6261, crenezumab, crizanlizumab, crotedumab, cusatuzumab, cytokine, dacetuzumab, daclizumab, dalotuzumab, dapirolizumab, daratumumab, dectrekumab, demcizumab, denintuzumab, denosumab, depatuxizumab, derlotuximab, detumomab, dezamizumab, dinutuximab, diridavumab, domagrozumab, dorlimomab, drozitumab, ds-8201, duligotuzumab, dupilumab, durvalumab, dusigitumab, duvortuxizumab, ecromeximab, eculizumab, edobacomab, edrecolomab, efalizumab, efungumab, eldelumab, elezanumab, elgemtumab, elotuzumab, elsilimomab, emactuzumab, emapalumab, emibetuzumab, emicizumab, enapotamab, enavatuzumab, enfortumab, enlimomab, enoblituzumab, enokizumab, enoticumab, ensituximab, ephrin a2, ephrin a3, ephrin a4, ephrin a5, ephrin b1, ephrin b2, ephrin b3, ephrins, epidermal growth factor, epigen, epiregulin, epitumomab, epratuzumab, eptinezumab, erenumab, erlizumab, ertumaxomab, erythropoietin, etaracizumab, etigilimab, etrolizumab, evinacumab, evolocumab, exbivirumab, fanolesomab, faralimomab, faricimab, farletuzumab, fasinumab, fbta05, felvizumab, fezakinumab, fibatuzumab, fibroblast growth factor 1-23, fibroblast growth factors, ficlatuzumab, figitumumab, firivumab, flanvotumab, fletikumab, flotetuzumab, foetal bovine somatotrophin, fontolizumab, foralumab, foravirumab, fremanezumab, fresolimumab, frunevetmab, fulranumab, futuximab, galcanezumab, galiximab, gancotamab, ganitumab, gantenerumab, gatipotuzumab, gavilimomab, gdnf family of ligands glial cell line-derived neurotrophic factor, gedivumab, gemtuzumab, gevokizumab, gilvetmab, gimsilumab, girentuximab, glembatumumab, golimumab, gomiliximab, gosuranemab, granulocyte colony-stimulating factor, granulocyte macrophage colony-stimulating factor, growth differentiation factor-9, growth factors, growth factor receptors, guselkumab, heparin-binding epidermal growth factor, heparin-binding growth factor, hepatocyte growth factor, hepatocyte growth factor-like protein, hepatoma-derived growth factor, heregulin, hormones, ianalumab, ibalizumab, ibi308, ibritumomab, icrucumab, idarucizumab, ifabotuzumab, igovomab, iladatuzumab, imab362, imalumab, imaprelimab, imciromab, imgatuzumab, inclacumab, indatuximab, indusatumab, inebilizumab, infliximab, inolimomab, inotuzumab, insulin, insulin-like growth factor-2, insulin-like growth factors, interleukin-6, interleukins, intetumumab, iomab-b, ipilimumab, iratumumab, isatuximab, iscalimab, istiratumab, itolizumab, ixekizumab, keliximab, keratinocyte growth factor, labetuzumab, lacnotuzumab, ladiratuzumab, lampalizumab, lanadelumab, landogrozumab, laprituximab, larcaviximab, lebrikizumab, lemalesomab, lendalizumab, lenvervimab, lenzilumab, lerdelimumab, leronlimab, lesofavumab, letolizumab, leukemia inhibitory factor, lexatumumab, libivirumab, lifastuzumab, ligelizumab, lilotomab, lintuzumab, lirilumab, lodelcizumab, lokivetmab, loncastuximab, lorvotuzumab, losatuximab, lucatumumab, lulizumab, lumiliximab, lumretuzumab, lupartumab, lutikizumab, mabp1, macrophage colony-stimulating factor, macrophage-stimulating protein, mapatumumab, margetuximab, marstacimab, maslimomab, matuzumab, mavrilimumab, mepolizumab, metelimumab, migration-stimulating factor, milatuzumab, minretumomab, mirikizumab, mitumomab, modotuximab, mogamulizumab, monalizumab, morolimumab, mosunetuzumab, motavizumab, moxetumomab, muromonab, myostatin, nacolomab, namilumab, naptumomab, naratuximab, narnatumab, natalizumab, navicixizumab, navivumab, naxitamab, nebacumab, necitumumab, nemolizumab, neod001, nerelimomab, nerve growth factors, nesvacumab, netakimab, neuregulin 1-4, neuregulins, neuropilin-1, neurotrophin-3, neurotrophin-4, neurotrophins, neurotrophins brain-derived neurotrophic factor, neurturin, nimotuzumab, nirsevimab, nivolumab, nofetumomab, obiltoxaximab, obinutuzumab, ocaratuzumab, ocrelizumab, odulimomab, ofatumumab, olaratumab, oleclumab, olendalizumab, olokizumab, omalizumab, oms721, onartuzumab, ontuxizumab, onvatilimab, opicinumab, oportuzumab, oregovomab, orf viral vascular endothelial growth factor homologs, orticumab, otelixizumab, otilimab, otlertuzumab, oxelumab, ozanezumab, ozoralizumab, pagibaximab, palivizumab, pamrevlumab, panitumumab, pankomab, panobacumab, parsatuzumab, pascolizumab, pasotuxizumab, pateclizumab, patritumab, pdr001, pembrolizumab, pemtumomab, peptides, perakizumab, persephin, pertuzumab, pexelizumab, pidilizumab, pinatuzumab, pintumomab, placenta growth factor, placental growth factor, placulumab, platelet-derived growth factor, platelet-derived growth factor-alpha polypeptide, plozalizumab, pogalizumab, polatuzumab, ponezumab, porgaviximab, prasinezumab, prezalizumab, priliximab, pritoxaximab, pritumumab, pro 140, proteins, quilizumab, racotumomab, radretumab, rafivirumab, ralpancizumab, ramucirumab, ranevetmab, ranibizumab, ravagalimab, ravulizumab, raxibacumab, refanezumab, regavirumab, remtolumab, reslizumab, rilotumumab, rinucumab, risankizumab, rituximab, rivabazumab, rmab, robatumumab, roledumab, romilkimab, romosozumab, rontalizumab, rosmantuzumab, rovalpituzumab, rovelizumab, rozanolixizumab, ruplizumab, sa237, samalizumab, samrotamab, sapelizumab, sarilumab, satralizumab, secukinumab, selicrelumab, seribantumab, setoxaximab, setrusumab, sevirumab, sgn-cd19a, shp647, sibrotuzumab, sifalimumab, siltuximab, simtuzumab, sipilizumab, sirtratumab, sirukumab, sofituzumab, solanezumab, solitomab, sonepcizumab, sontuzumab, spartalizumab, stamulumab, sulesomab, suptavumab, sutimlimab, suvizumab, suvratoxumab, tabalumab, tacatuzumab, tadocizumab, talacotuzumab, talizumab, tamtuvetmab, tanezumab, tanibirumab, taplitumomab, tarextumab, tavolimab, t-cell growth factor, tefibazumab, telimomab, telisotuzumab, tenatumomab, teneliximab, teplizumab, tepoditamab, teprotumumab, tesidolumab, tetulomab, tezepelumab, tgn1412, thrombopoietin, tibulizumab, tigatuzumab, tildrakizumab, timigutuzumab, timolumab, tiragotumab, tislelizumab, tisotumab, tnx-650, tocilizumab, tomuzotuximab, toralizumab, tosatoxumab, tositumomab, tovetumab, tralokinumab, transforming growth factor alpha, transforming growth factor beta, transforming growth factors, trastuzumab, trbs07, tregalizumab, tremelimumab, trevogrumab, tucotuzumab, tumor necrosis factor-alpha, tuvirumab, ublituximab, ulocuplumab, urelumab, urtoxazumab, ustekinumab, utomilumab, vadastuximab, vanalimab, vandortuzumab, vantictumab, vanucizumab, vapaliximab, varisacumab, varlilumab, vascular endothelial growth factor a-f, vascular endothelial growth factors, vascular permeability factor, vatelizumab, vedolizumab, veltuzumab, vepalimomab, vesencumab, visilizumab, vobarilizumab, volociximab, vonlerolizumab, vopratelimab, vorsetuzumab, votumumab, vunakizumab, xentuzumab, xmab-5574, zalutumumab, zanolimumab, zatuximab, zenocutuzumab, ziralimumab, zolbetuximab, and zolimomab. In some embodiments, the ligand comprises an RNA aptamer, peptide aptamer, polypeptide, such as a cell surface receptor, or a sugar, folic acid, or folate.

In some embodiments, a ligand may be attached to a lipid molecule in a particle through a polymer linkage. For example, amphiphilic particles of targeting ligands comprising a hydrophilic polymer spacer between a lipid anchor and a ligand group can be attached to the surface of liposomes to offer receptor-specific targeting. The particle can be synthesized with three main conjugation methods: reaction between activated carboxyl groups and amino groups yielding an amide bond, reaction between pyridyldithiols and thiols yielding disulfide bonds, and reaction between maleimide derivatives and thiols yielding thioether bonds. With the later, conjugation of ligands such as antibody fragments with maleimide chemistry using naturally occurring cysteine residue, engineered C-terminal cysteine, or thiolated with Traut's reagent may provide strong stable bonds. Reactions with the cysteine on antibody fragments can offer ideal orientation, distant from antibody binding site, minimizing interference with binding. A polymer linker like PEG also helps with the orientation, extending the ligand far enough from the PEG shielding so the ligand is accessible to receptors on cells.

In some embodiments, a micelle transfer method may be used to construct particles herein. In the micelle transfer method, micellar conjugates of the ligand and an amphiphilic lipid co-incubated with preformed liposomes spontaneously insert themselves into liposome bilayers without the loss of the liposome integrity, providing a rapid and simple method for transforming non-targeted liposomes into antibody-targeted liposomes. Insertion is performed at 55-60° C., so the denaturation of protein ligands is a concern, but longer overnight incubation at 37° C. is also possible. Liposomes may remain mostly unaltered through conjugations.

In some embodiments, the ligand targets a specific cell surface receptor on a target cell, for example, a receptor that is overexpressed on a particular target cell such as a tumor cell. In some embodiments, the receptor may comprise one or more of: CD44, GD2, folate receptor, transferrin receptor, CD3, glycoprotein IIb/IIIa, IL-2Rα receptor (CD25), CD20, IL-2Rα receptor (CD25), TNFα, RSV F protein, ErbB2/HER2, CD52, CD11a, VEGF, VEGFR, EGFR, immunoglobulin E (IgE), alpha-4 (α4) integrin, complement system protein C5, IL-1β, IL-6R, BAFF, CD30, CTLA-4, IL-12, IL-23, PD-1, α4β7, CD38, or a receptor tyrosine kinase. In some embodiments, the ligand targets one or more members of the ErbB family of receptor tyrosine kinases. The ErbB family consists of four structurally related transmembrane receptor tyrosine kinases EGFR/HER1 (epidermal growth factor receptor/human EGFR 1), HER2 (human EGFR 2), HER3 (human EGFR 3), and HER4 (human EGFR 4). For example, HER2 overexpression is also known to occur in ovarian, stomach, prostrate, lung, uterine, pancreas, and thyroid carcinomas. For example, EGFR overexpression occurs in many human cancers including breast, lung, colorectal and brain cancers and can result in poor prognosis. In such embodiments, the ligand may be derived from one or more of cetuximab, panitumumab, zalutumumab, nimotuzumab, and matuzumab. In some embodiments, the ligand does not target HER2 or EGFR, but may target one of the other above receptor proteins.

In some embodiments, the ligand targets a molecule such as one or more of the following: 1-40-β-amyloid, 4-1BB, SAC, 5'-nucleotidase, 5T4, activated F9, F10, activin receptor-like kinase 1, ACVR2B, adenocarcinoma antigen, adrenomedullin, alpha-4 integrin, alpha-fetoprotein, amphiregulin, amyloid, angiopoietin, angiopoietin 2, angiopoietin 3, anthrax toxin, anti-apoptotic survival factor, AOC3, artemin, autocrine motility factor, AXL, B7-H3, Bacillus anthracis anthrax, BAFF, BAFF-R, BCMA, beta amyloid, betacellulin, B-lymphoma cell, BLyS, bone morphogenetic proteins, C1s, C242 antigen, C5, CA-125, calcitonin, calcitonin gene-related peptide, calcitonin related polypeptide alpha, Canis lupus familiaris IL31, carbonic anhydrase 9, cardiac myosin, CCL11, CCR2, CCR4, CCR5, CD11, CD11a, CD123, CD125, CD134, CD137, CD140a, CD147, CD15, CD152, CD154, CD18, CD184, CD19, CD2, CD20, CD200, CD22, CD221, CD23, CD25, CD27, CD276, CD279, CD28, CD3, CD3 epsilon, CD30, CD319, CD33, CD37, CD38, CD3E, CD4, CD40, CD40L, CD41, CD44 v6, CD45, CD49b, CD5, CD51, CD52, CD54, CD56, CD6, Cd62L, CD70, CD74, CD79B, CD80, CD97B, CEA, CEACAM5, CEA-related antigen, CFD, CGRP, ciliary neurotrophic factor family, CLDN18, CLDN18.2, *Clostridium difficile, Clostridium difficile* toxin B, clumping factor A, c-Met, coagulation factor III, colony-stimulating factors, complement C5a, Complement component 5, CSF1, CSF1R, CSF2, CTGF, CTLA-4, CXCR4, cytokine, cytomegalovirus, cytomegalovirus glycoprotein B, dabigatran, dendritic cell-associated lectin 2, DLL3, DLL4, DPP4, DR5, *E. coli* shiga toxin type-1, *E. coli* shiga toxin type-2, ebolavirus glycoprotein, EGFL7, EGFR, EGFR 1-4, EGFR extracellular domain III, endoglin, endotoxin, eotaxin-1, EpCAM, EPHA3, ephrin a2, ephrin a3, ephrin a4, ephrin a5, ephrin b1, ephrin b2, ephrin b3, ephrin receptor A3, ephrins, epidermal growth factor, epigen, epiregulin, episialin, erythropoietin, *Escherichia coli*, F protein of respiratory syncytial virus, F protein of RSV, Factor Ixa, Factor X, FAP, FCGRT, FGF 23, FGFR2, fibrin II beta chain, fibroblast growth factor 1-23, fibroblast growth factors, fibronectin extra domain-B, foetal bovine somatotrophin, folate hydrolase, folate receptor, folate receptor 1, folate receptor alpha, Frizzled receptor, GCGR, GD2, GD2 ganglioside, GD3 ganglioside, GDF-8, gdnf family of ligands glial cell line-derived neurotrophic factor, gelatinase B, glycoprotein 75, glypican 3, GMCSF, GMCSF receptor α-chain, GPIIb/IIIa, GPNMB, granulocyte colony-stimulating factor, granulocyte macrophage colony-stimulating factor, growth differentiation factor 8, growth differentiation factor-9, growth factors, growth factor receptors, GUCY2C, hemagglutinin, hemagglutinin HA, heparin-binding epidermal growth factor, heparin-binding growth factor, hepatitis B surface antigen, hepatitis B surface antigen, hepatitis B virus, hepatocyte growth factor, hepatocyte growth factor-like protein, hepatoma-derived growth factor, HER, HER 1-4, HER2, HER3, HER4, heregulin, HGF, HGFR, HHGFR, histone complex, HIV-1, HLA-DR, HNGF, hormones, Hsp90, human beta-amyloid, human scatter factor receptor kinase, human TNF, ICAM-1, ICOS, ICOSL, IFN-α, IFN-γ, IgE, IgE Fc region, IGF1, IGF-1 receptor, IGF2, IGHE, IL-1, IL-12, IL-12R, IL-13, IL-13R, IL-17, IL-17A, IL-17F, IL-17R, IL-17RA, IL-1A, IL-1B, IL-1R, IL-1β, IL-2, IL-20, IL-20R, IL-22, IL-22R, IL-23, IL-23A, IL-23R, IL-2R, IL-2RA, IL-31, IL-31RA, IL-4, IL-4RA, IL-5, IL-5RA, IL-6, IL-6R, IL-9, IL-9R, IL-GF2, Influenza A hemagglutinin, influenza A virus hemagglutinin, influenza A virus hemagglutinin HA, insulin, insulin-like growth factor-2, insulin-like growth factors, integrin receptor, integrin α4, integrin α4β7, integrin α5β1, integrin αIIbβ3, integrin αvβ3, integrin β7, interferon gamma, interferon gamma-induced protein, interferon receptor, interferon α/β receptor, interleukin receptors, interleukins, ITGA2, ITGB2, kallikrein, keratinocyte growth factor, KIR2D, leukemia inhibitory factor, Lewis-Y antigen, LFA-1, LINGO-1, lipoteichoic acid, LIV-1, LOXL2, LRRC15, L-selectin, LTA, LYPD3, macrophage colony-stimulating factor, macrophage-stimulating protein, MASP-2, MCAM, MCP-1, MCSF, mesothelin, MIF, migration-stimulating factor, MS4A1, MSLN, MUC1, mucin CanAg, mucosal addressin cell adhesion molecule, myelin-associated glycoprotein, myostatin, NACP, NCA-90, nectin-4, nerve growth factors, neural apoptosis-regulated proteinase 1, neuregulin 1-4, neuregulins, neuropilin-1, neurotrophin-3, neurotrophin-4, neurotrophins, neurotrophins brain-derived neurotrophic factor, neurturin, NGF, NGNA ganglioside, NKG2A, NOGO-A, Notch 1, Notch receptor, NRP1, orf viral vascular endothelial growth factor homologs, OX-40, oxLDL, PCDC1, PCSK9, PD-1, PDCD1, PDGF-R α, PDGFRA, PD-L1, peptides, persephin, phosphate-sodium co-transporter, phosphatidylserine, placenta growth factor, placental growth factor, platelet-derived growth factor, platelet-derived growth factor receptor beta, platelet-derived growth factor-alpha polypeptide, programmed cell death 1, prostatic carcinoma cells, Protective antigen of *Bacillus anthracis*, Protective antigen of the Anthrax toxin, proteins, *Pseudomonas aeruginosa, Pseudomonas aeruginosa* type III secretion system, PSMA, PTK7, rabies virus G glycoprotein, rabies virus glycoprotein, RANKL, respiratory syncytial virus, RGMA, RHD, Rhesus factor, RON, root plate-specific spondin 3, RSVFR, RTN4, sclerostin, SDC1, selectin P, serum amyloid A protein, serum amyloid P component, SLAMF7, SLITRK6, SOST, sphingosine-1-phosphate, *Staphylococcus aureus, Staphylococcus aureus* alpha toxin, *Staphylococcus aureus* bi-component leukocidin, STEAP1, TAG-72, tau protein, t-cell growth factor, T-cell receptor, TEM1, tenascin C, TFPI, TGF beta 1, TGF beta 2, TGF-β, thrombopoietin, TIGIT, TNF, TNF alpha, TNFR superfamily member 4, TNFRSF8, TRAIL-R1, TRAIL-R2, transforming growth factor alpha, transforming growth factor beta, transforming growth factors, TRAP, TROP-2, TSLP, tumor antigen CTAA16.88, tumor necrosis factor-alpha, tumor specific glycosylation of MUC1, TWEAK receptor, TYRP1, VAP-1, vascular endothelial growth factor a-f, vascular endothelial growth factors, vascular permeability factor, VEGF, VEGF A-F, VEGFR, VEGFR1, VEGFR2, VEGFR3, vimentin, VSIR, VWF, Zaire ebolavirus glycoprotein, among others.

In some embodiments, the target cell is a tumor cell, such as a solid tumor cell or a lymphoma or leukemia cell. In some embodiments, the target tumor or tumor-associated cell is selected from a solid tumor cell, a tumor stem cell, or a tumor-associated macrophage. In other embodiments, the target cell is an infectious cell, such as a bacterial cell, fungal cell such as a yeast cell, or a eukaryotic infectious cell. In some embodiments, the target cell is an epithelial cell. In some embodiments, the target cell is an inflammatory cell such as a monocyte or macrophage cell.

Drugs that can be incorporated into particles herein may comprise any drug molecule capable of inhabiting the interior of a liposome particle or associating with the lipid surface layer of a particle. Drugs may include small molecule chemicals as well as peptide or protein drugs and nucleic acid drugs, for example. In some embodiments, the drug or drugs included in a particle may be anti-cancer drugs, anti-inflammatory agents, chemotherapy drugs, or kinase inhibitors. In some embodiments, drugs may comprise compounds intended for diagnostic purposes, including dyes or fluorescent or radio-labeled molecules.

Therapeutic agents compatible with embodiments of ligand-drug particles herein (for example, as incorporated drugs or ligands or in the case of liposomal drugs or other types of particle drugs, that may be modified into a ligand-drug particle, such as by adding a ligand as described herein) may include agents such as 5-FU (Fluorouracil), Abemaciclib, Abiraterone Acetate, Abitrexate® (Methotrexate), Abraxane® (Paclitaxel Albumin-stabilized Nanoparticle Formulation), ABVD, ABVE, ABVE-PC, AC, Acalabrutinib, AC-T, Actigall®, Actos®, Adcetris® (Brentuximab Vedotin), ADE, Ado-Trastuzumab Emtansine, Adriamycin (Doxorubicin Hydrochloride), Afatinib Dimaleate, Afinitor® (Everolimus), Akynzeo® (Netupitant and Palonosetron Hydrochloride), Aldara® (Imiquimod), Aldesleukin, Alecensa® (Alectinib), Alectinib, Alemtuzumab, Alimta® (Pemetrexed Disodium), Aliqopa® (Copanlisib Hydrochloride), Alkeran® for Injection (Melphalan Hydrochloride), Alkeran® Tablets (Melphalan), Aloxi® (Palonosetron Hydrochloride), Alunbrig® (Brigatinib), amadotin, Ambochlorin® (Chlorambucil), Amboclorin® (Chlorambucil), Amifostine, Aminolevulinic Acid, Anastrozole, Apalutamide, Aprepitant, Aredia® (Pamidronate Disodium), Arimidex® (Anastrozole), aritox, Aromasin® (Exemestane), Arranon® (Nelarabine), Arsenic Trioxide, Arzerra® (Ofatumumab), Asparaginase Erwinia chrysanthemi, Atezolizumab, Avandia, Avastin® (Bevacizumab), Avelumab, Axicabtagene Ciloleucel, Axitinib, Azacitidine, azathioprine, Bavencio® (Avelumab), BEACOPP, Becenum® (Carmustine), Beleodaq® (Belinostat), Belinostat®, Bendamustine Hydrochloride, BEP, Besponsa® (Inotuzumab Ozogamicin), betaine, Bevacizumab, Bexarotene, Bicalutamide, BiCNU® (Carmustine), Bleomycin, Blinatumomab, Blincyto® (Blinatumomab), bogatox, Bortezomib, Bosulif® (Bosutinib), Bosutinib, Brentuximab Vedotin, Brigatinib, BuMel, Busulfan, Busulfex® (Busulfan), Cabazitaxel, Cabometyx® (Cabozantinib-S-Malate), Cabozantinib-S-Malate, CAF, Calquence® (Acalabrutinib), Campath® (Alemtuzumab), Camptosar® (Irinotecan Hydrochloride), Capecitabine, CAPDX, Carac® (Fluorouracil—Topical), Carboplatin, CARBOPLATIN-TAXOL, Carfilzomib,® (Carmustine), Carmustine, Carmustine Implant, Casodex® (Bicalutamide), CEM, Ceritinib, Cerubidine (Daunorubicin Hydrochloride), Cervarix® (Recombinant HPV Bivalent Vaccine), Cetuximab, CEV, Chlorambucil, CHLORAMBUCIL-PREDNISONE, Cholbam, cholic acid, CHOP, Cisplatin, cituxetan, Cladribine, Clafen® (Cyclophosphamide), Clofarabine, Clofarex® (Clofarabine), Clolar® (Clofarabine), CMF, Cobimetinib, colchicine, Cometriq® (Cabozantinib-S-Malate), Copanlisib Hydrochloride, COPDAC, COPP, COPP-ABV, Cosmegen® (Dactinomycin), Cotellic® (Cobimetinib), Creon, Crizotinib, CVP, Cyclophosphamide, Cyfos® (Ifosfamide), Cyramza® (Ramucirumab), Cystadane, Cytarabine, Cytarabine Liposome, Cytosar-U® (Cytarabine), Cytoxan® (Cyclophosphamide), Dabrafenib, Dacarbazine, Dacogen® (Decitabine), Dactinomycin, Daratumumab, Darzalex® (Daratumumab), Dasatinib, Daunorubicin Hydrochloride, Daunorubicin Hydrochloride and Cytarabine Liposome, Decitabine, Defibrotide Sodium, Defitelio® (Defibrotide Sodium), Degarelix, Denileukin Diftitox, Denosumab, DepoCyt® (Cytarabine Liposome), Dexamethasone, Dexrazoxane Hydrochloride, Dinutuximab, Docetaxel, Doxil® (Doxorubicin Hydrochloride Liposome), doxorubicin, Doxorubicin Hydrochloride, Doxorubicin Hydrochloride Liposome, Dox-SL (Doxorubicin Hydrochloride Liposome), DTIC-Dome® (Dacarbazine), Durvalumab, Efudex® (Fluorouracil—Topical), Elitek® (Rasburicase), Ellence® (Epirubicin Hydrochloride), Elotuzumab, Eloxatin® (Oxaliplatin), Eltrombopag Olamine, Emend® (Aprepitant), Empliciti® (Elotuzumab), emtansine, Enasidenib Mesylate, Enzalutamide, Epirubicin Hydrochloride, EPOCH, Erbitux® (Cetuximab), Eribulin Mesylate, Erivedge® (Vismodegib), Erleada® (Apalutamide), Erlotinib Hydrochloride, Erwinaze® (Asparaginase Erwinia chrysanthemi), Ethyol® (Amifostine), Etopophos® (Etoposide Phosphate), Etoposide, Etoposide Phosphate, Evacet® (Doxorubicin Hydrochloride Liposome), Everolimus, Evista® (Raloxifene Hydrochloride), Evomela® (Melphalan Hydrochloride), Exemestane, Fareston® (Toremifene), Farydak® (Panobinostat), Faslodex® (Fulvestrant), FEC, Femara® (Letrozole), Filgrastim, floxuridine, Fludara® (Fludarabine Phosphate), Fludarabine Phosphate, Fluoroplex® (Fluorouracil—Topical), Fluorouracil Injection, Fluorouracil—Topical, Flutamide, Folex® (Methotrexate), Folex® PFS (Methotrexate), one or more components of FOLFIRI, FOLFIRI-BEVACIZUMAB, FOLFIRI-CETUXIMAB, FOLFIRINOX, FOLFOX, Folotyn® (Pralatrexate), FUDR, FU-LV, Fulvestrant, Gardasil® (Recombinant HPV Quadrivalent Vaccine), Gardasil 9® (Recombinant HPV Nonavalent Vaccine), Gazyva® (Obinutuzumab), Gefitinib, Gemcitabine Hydrochloride, GEMCITABINE-CISPLATIN, GEMCITABINE-OXALIPLATIN, Gemtuzumab Ozogamicin, Gemzar® (Gemcitabine Hydrochloride), Gilotrif® (Afatinib Dimaleate), Gleevec (Imatinib Mesylate), Gliadel® (Carmustine Implant), Gliadel wafer (Carmustine Implant), Glucarpidase, Goserelin Acetate, govitecan, Halaven® (Eribulin Mesylate), Hemangeol® (Propranolol Hydrochloride), Herceptin® (Trastuzumab), HPV Bivalent Vaccine, Recombinant, HPV Nonavalent Vaccine, Recombinant, HPV Quadrivalent Vaccine, Recombinant, Humatin, Hycamtin® (Topotecan Hydrochloride), Hydrea® (Hydroxyurea), Hydroxyurea, Hyper-CVAD, Ibrance® (Palbociclib), Ibritumomab Tiuxetan, Ibrutinib, ICE, Iclusig® (Ponatinib Hydrochloride), Idamycin® (Idarubicin Hydrochloride), Idarubicin Hydrochloride, Idelalisib, Idhifa® (Enasidenib Mesylate), Ifex® (Ifosfamide), Ifosfamide, Ifosfamidum® (Ifosfamide), IL-2 (Aldesleukin), Imatinib Mesylate, Imbruvica® (Ibrutinib), Imfinzi® (Durvalumab), Imiquimod, Imlygic® (Talimogene Laherparepvec), Inlyta® (Axitinib), Inotuzumab Ozogamicin, Interferon Alfa-2b, Recombinant, Interleukin-2 (Aldesleukin), Intron A (Recombinant Interferon Alfa-2b), Ipilimumab, Iressa® (Gefitinib), Irinotecan Hydrochloride, Irinotecan Hydrochloride Liposome, Istodax® (Romidepsin), Ixabepilone, ixadotin, Ixazomib Citrate, Ixempra® (Ixabepilone), Jakafi® (Ruxolitinib Phosphate), JEB, Jevtana® (Cabazitaxel), Kadcyla® (Ado-Trastuzumab Emtansine), Keoxifene® (Raloxifene Hydrochloride), Kepivance® (Palifermin), Keytruda® (Pembrolizumab), Kisqali® (Ribociclib), Kymriah® (Tisagenlecleucel), Kyprolis® (Carfilzomib), Lanreotide Acetate, Lapatinib Ditosylate, Lartruvo® (Olaratumab), Lenalidomide, Lenvatinib Mesylate, Lenvima (Lenvatinib Mesylate), Letrozole, Leucovorin Calcium, Leukeran® (Chlorambucil), Leuprolide Acetate, Leustatin® (Cladribine), Levulan® (Aminolevulinic Acid), Linfolizin® (Chlorambucil), LipoDox® (Doxorubicin Hydrochloride Liposome), Lomustine, Lonsurf® (Trifluridine and Tipiracil Hydrochloride), Luminal, Lupron® (Leuprolide Acetate), Lupron® Depot (Leuprolide Acetate), Lupron® Depot-Ped (Leuprolide Acetate), Lutathera® (Lutetium Lu 177-Dotatate), Lutetium® (Lu 177-Dotatate), Lynparza® (Olaparib), mafenatox, mafodotin, Marqibo® (Vincristine Sulfate Liposome), Matulane® (Procarbazine Hydrochloride), Mechlorethamine Hydrochloride, Megestrol Acetate, Mekinist (Trametinib), Melphalan, Melphalan Hydrochloride, Mercaptopurine, merpentan, mertansine, Mesna, Mesnex® (Mesna), Methazolastone® (Temozolomide), Methotrexate, Methotrexate LPF (Methotrexate), Methylnaltrexone Bromide, Mexate® (Methotrexate), Mexate®-AQ (Methotrexate), Midostaurin, Mitomycin C, Mitoxantrone Hydrochloride, Mitozytrex® (Mitomycin C), monatox, MOPP, Mozobil® (Plerixafor), Mustargen (Mechlorethamine Hydrochloride), Mutamycin® (Mitomycin C), Myleran® (Busulfan), Mylosar® (Azacitidine), Mylotarg® (Gemtuzumab Ozogamicin), nadolol, Nanoparticle Paclitaxel (Paclitaxel Albumin-stabilized Nanoparticle Formulation), Navelbine® (Vinorelbine Tartrate), Necitumumab, Nelarabine, Neo-Fradin, neomycin, Neosar® (Cyclophosphamide), Neo-Tab, Neratinib Maleate, Nerlynx® (Neratinib Maleate), Netupitant and Palonosetron Hydrochloride, Neulasta® (Pegfilgrastim), Neupogen® (Filgrastim), Nexavar® (Sorafenib Tosylate), Nilandron® (Nilutamide), Nilotinib, Nilutamide, Ninlaro® (Ixazomib Citrate), Niraparib Tosylate Monohydrate, Nivolumab, Nolvadex® (Tamoxifen Citrate), Nplate® (Romiplostim), obeticholic acid, Obinutuzumab, Ocaliva, Odomzo® (Sonidegib), OEPA, Ofatumumab, OFF, Olaparib, Olaratumab, Omacetaxine Mepesuccinate, Oncaspar® (Pegaspargase), Ondansetron Hydrochloride, Onivyde® (Irinotecan Hydrochloride Liposome), Ontak® (Denileukin Diftitox), Opdivo, Opdivo® (Nivolumab), OPPA, orlistat, Osimertinib, Oxaliplatin, ozogamicin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Pancreaze, pancrelipase, Pangestyme EC, Panitumumab, Panobinostat, Panocaps, paptox, Paraplat® (Carboplatin), Paraplatin® (Carboplatin), paromomycin, pasudotox, Pazopanib Hydrochloride, PCV, PEB, Pegaspargase, Pegfilgrastim, Peginterferon Alfa-2b, PEG-Intron® (Peginterferon Alfa-2b), pelidotin, Pembrolizumab, Pemetrexed Disodium, pendetide, pentetate, Perjeta® (Pertuzumab), Pertuzumab, Pertzye, phenobarbital, pioglitazone, Platinol® (Cisplatin), Platinol-®AQ (Cisplatin), Plerixafor, Pomalidomide, Pomalyst® (Pomalidomide), Ponatinib Hydrochloride, Portrazza® (Necitumumab), Pralatrexate, Prednisone, Procarbazine Hydrochloride, Proleukin® (Aldesleukin), Prolia (Denosumab), Promacta® (Eltrombopag Olamine), propranolol, Propranolol Hydrochloride, Provenge® (Sipuleucel-T), Purinethol® (Mercaptopurine), Purixan® (Mercaptopurine), Radium 223 Dichloride, Raloxifene Hydrochloride, Ramucirumab, Rasburicase, ravtansine, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor® (Methylnaltrexone Bromide), R-EPOCH, Revlimid® (Lenalidomide), Rheumatrex® (Methotrexate), Ribociclib, R-ICE, Rituxan (Rituximab), Rituxan Hycela (Rituximab and Hyaluronidase Human), Rituximab, Rituximab and Hyaluronidase Human, Rolapitant Hydrochloride, Romidepsin, Romiplostim, rosiglitazone, Rubidomycin (Daunorubicin Hydrochloride), Rubraca® (Rucaparib Camsylate), Rucaparib Camsylate, Ruxolitinib Phosphate, Rydapt® (Midostaurin), satetraxetan, Sclerosol Intrapleural Aerosol (Talc), Siltuximab, Sipuleucel-T, Somatuline® Depot (Lanreotide Acetate), Sonidegib, Sorafenib Tosylate, soravtansine, Sprycel® (Dasatinib), STANFORD V, Sterile Talc Powder (Talc), Steritalc® (Talc), Stivarga® (Regorafenib), Sunitinib Malate, Sutent® (Sunitinib Malate), Sylatron® (Peginterferon Alfa-2b), Sylvant® (Siltuximab), Synribo® (Omacetaxine Mepesuccinate), Tabloid® (Thioguanine), TAC, tafenatox, Tafinlar® (Dabrafenib), Tagrisso® (Osimertinib), Talc, Talimogene Laherparepvec, talirine, Tamoxifen Citrate, Tarabine® PFS (Cytarabine), Tarceva® (Erlotinib Hydrochloride), Targretin® (Bexarotene), Tasigna® (Nilotinib), Taxol (Paclitaxel), Taxotere® (Docetaxel), Tecentriq® (Atezolizumab), Temodar® (Temozolomide), Temozolomide, Temsirolimus, tesirine, tetraxetan, Thalidomide, Thalomid® (Thalidomide), Thioguanine, Thiotepa, Ti sagenlecleucel, tiuxetan, Tolak® (Fluorouracil—Topical), Topotecan Hydrochloride, Toremifene, Torisel® (Temsirolimus), Totect® (Dexrazoxane Hydrochloride), TPF, Trabectedin, Trametinib, Trastuzumab, Treanda® (Bendamustine Hydrochloride), Trifluridine and Tipiracil Hydrochloride, Trisenox® (Arsenic Trioxide), Tykerb® (Lapatinib Ditosylate), Ultresa, Unituxin® (Dinutuximab), Uridine Triacetate, Urso, Urso Forte, ursodiol, VAC, Valrubicin, Valstar® (Valrubicin), VAMP, Vandetanib, Varubi® (Rolapitant Hydrochloride), Vectibix® (Panitumumab), vedotin, VeIP, Velban® (Vinblastine Sulfate), Velcade® (Bortezomib), Velsar® (Vinblastine Sulfate), Vemurafenib, Venclexta® (Venetoclax), Venetoclax, Verzenio® (Abemaciclib), Viadur (Leuprolide Acetate), Vidaza® (Azacitidine), Vinblastine Sulfate, Vincasar® PFS (Vincristine Sulfate), Vincristine Sulfate, Vincristine Sulfate Liposome, Vinorelbine Tartrate, Viokace, Viokase, VIP, Vismodegib, Vistogard® (Uridine Triacetate), Voraxaze® (Glucarpidase), Vorinostat, Votrient® (Pazopanib Hydrochloride), Vyxeos® (Daunorubicin Hydrochloride and Cytarabine Liposome), Wellcovorin (Leucovorin Calcium), Xalkori® (Crizotinib), XELIRI, Xeloda® (Capecitabine), XELOX, Xgeva® (Denosumab), Xofigo® (Radium 223 Dichloride), Xtandi® (Enzalutamide), Yervoy® (Ipilimumab), Yescarta® (Axicabtagene Ciloleucel), Yondelis® (Trabectedin), Zaltrap® (Ziv-Aflibercept), Zarxio® (Filgrastim), Zejula® (Niraparib Tosylate Monohydrate), Zelboraf® (Vemurafenib), Zenpep, Zevalin® (Ibritumomab Tiuxetan), Zinecard® (Dexrazoxane Hydrochloride), Ziv-Aflibercept, Zofran® (Ondansetron Hydrochloride), Zoladex® (Goserelin Acetate), Zoledronic Acid, Zolinza® (Vorinostat), Zometa® (Zoledronic Acid), Zydelig® (Idelalisib), Zykadia® (Ceritinib), and Zytiga® (Abiraterone Acetate), among others.

Uptake of Particles

To optimize the uptake of ligand-conjugated liposomes to cells, ligands should have high affinity binding to the targeted receptors. The rapid screening and identifying of tumor-specific high affinity internalizing human antibodies and antibody fragments from phage and yeast display of non-immune phage antibody libraries may be used for ligand selection. Access of the ligand to the receptor may also be important. A polymer linker such as PEG, for example, may be helpful to distance low molecular weight ligands such as folate from the liposomal surface and to allow receptor binding. Coupling of ligands to polymer linkers of various lengths to the distal terminals of antibody fragments and other ligands may improve binding, internalizing, and overall bioactivity in the delivery of drugs.

The affinity of soluble ligands for their receptors in vitro may not differ drastically from the affinity of ligands conjugated to liposomes for their receptors. The conjugation of anti-HER2 F5 scFv to liposomes has been shown to not significantly affect the ligand interaction with HER2 in HER2-overexpressing cell lines since the $K_D$ for the binding of monovalent F5 scFv conjugated liposomes ($K_D$=111 nM) and of soluble F5 scFv ($K_D$=160 nM) are comparable, for example. In addition, it has been shown that the high affinity binding of Fab'-conjugated immunoliposomes derived from antibody fragments of trastuzumab is comparable to that of free Fab' and intact antibody. Increasing the surface valency of ligands per liposomes correlates to increased targeted uptake in cells until a plateau, however, after which additional ligands may decrease binding and internalization. In HER2-overexpressing human breast cancer cells, it has been documented that the cell binding and internalization of anti-HER2 immunoliposomes increased at higher surface valency of conjugated ligands, reaching a plateau, depending on ligand, at ~40 trastuzumab-Fab'/liposome and a plateau at ~30 F5 scFv/liposome. Similarly, in EGFR-overexpressing human breast cancer cells, a plateau was reached, depending on ligand, at ~30-40 cetuximab-Fab'/liposome. Apparently, the limit on the binding and uptake of ligand-conjugated liposomes may be dependent on ligand valency per liposome and receptor expression level rather than on the cells than to ligand affinity.

In some embodiments herein, a particle comprises more than one targeting ligand. For example, a particle may comprise anti-HER2 and anti-EGFR dual-targeted ligands. Dual-targeted particles may allow for the examination of the antagonistic effects of a non-specific ligand possibly from steric hindrance on cells expressing only one of the receptors. Dual-targeting liposomes against HER2 and EGFR may improve the delivery of immunoliposomes to cell lines expressing both receptors by increasing the receptor density, but can also serve to simplify the formulation of ligand-targeted lipid particles that can target a larger array of cells, similar to a cocktail-targeting approach.

Determining Ligand Valency of a Ligand-Drug Particle

In some embodiments, the efficiency of uptake of a ligand-drug particle into a cell increases with the number of ligands found on the particle up to an optimum valency, and then plateaus or decreases as more ligands are added to the particle. The present disclosure provides results of mathematical modeling experiments conducted to predict the optimal valency for ligand-drug particles based on the dissociation constant for the ligand and its receptor on the target cell and on the expression level of the receptor by the target cell. For example, as described in the Examples below, an optimal valency for a ligand-drug particle may be determined where the target cell expresses on the order of from $10^3$ to $10^7$ receptors per cell. When a value is provided for the number of receptors expressed in a target cell, it is understood that the value is an average number for cells of that type as determined experimentally. Generally such values are rounded to one significant figure. A value that is "on the order of," for instance, $10^5$ or $10^6$ means a value that would round closest to $1\times10^5$ or $1\times10^6$ (for example $9\times10^5$ would round closest to $1\times10^6$ while $3\times10^5$ would round closest to $1\times10^5$).

When referring to valency determination herein, a cell providing "high expression" or cell "highly expressing" a particular receptor means a cell that expresses on the order of $10^6$ receptor molecules per cell. A "moderate expression" cell expresses on the order of $10^5$ receptor molecules per cell, while a "low expression" cell expresses on the order of $10^4$ receptor molecules per cell.

Particles with One Ligand Species

Table 1 below (also in the Examples below) provides calculated optimal valence for particles with a single ligand species specific for a receptor with high expression or moderate expression in the target cell, the valence also depending on the in vitro equilibrium dissociation constant of the ligand and receptor.

TABLE 1

Optimal valency for single ligand, single receptor under high and moderate average receptor expression levels
Optimal Multi-Valent Binding: Mono-Targeted

| | Valence (Ligands/Particle) | |
|---|---|---|
| $K_D$ (nM) | High | Moderate |
| 1000 | 19 | 23 |
| 100 | 17 | 21 |
| 10 | 16 | 19 |
| 1 | 14 | 17 |
| 0.1 | 13 | 15 |
| 0.01 | 11 | 13 |
| 0.001 | 10 | 12 |

Optimal valence for a more specific range of receptor expression levels are provided in Table 2.

TABLE 2

Optimal valency for single ligand, single receptor under specific average receptor expression levels ($R_T$) and receptor-ligand $K_D$
Optimal Multi-Valent Binding: Mono-Targeted/High Expression

| | | Valence (Ligands/Particle) | | | | | | |
|---|---|---|---|---|---|---|---|---|
| | $K_D$ (nM) | 4*10^5 | 5*10^5 | 6*10^5 | 7*10^5 | 8*10^5 | 9*10^5 | 10^6 | 3*10^6 |
| $R_T$ (#/cell) | 1000 | 36 | 29 | 25 | 23 | 21 | 20 | 19 | 12 |
| | 100 | 33 | 27 | 23 | 21 | 19 | 18 | 17 | 11 |
| | 10 | 30 | 24 | 21 | 19 | 18 | 16 | 16 | 10 |
| | 1 | 27 | 22 | 19 | 17 | 16 | 15 | 14 | 9 |
| | 0.1 | 24 | 19 | 17 | 15 | 14 | 13 | 13 | 8 |
| | 0.01 | 21 | 17 | 15 | 13 | 12 | 12 | 11 | 7 |
| | 0.001 | 18 | 15 | 13 | 12 | 11 | 10 | 10 | 6 |

As can be seen from Tables 1 and 2, ligand-drug particles comprising one ligand may have specific ligand valencies or ranges of ligand valencies depending upon the $K_D$ of the ligand-receptor interaction measured in vitro and on the average receptor expression level for the target cells, for example, measured in tissue culture. Actual chosen valencies where the $R_T$ and $K_D$ are on the order of the numbers shown in the two above tables may vary by plus or minus one. For example, for a $K_D$ on the order of 10 nM and an $R_T$ on the order of $5 \times 10^5$, the valency may be 24+/−1 or 23-25.

For example, in some embodiments, if the target cell highly expresses the receptor according to high expression as defined above, then the ligand-drug particle may have a valency of 10-19 ligands per particle, based on Table 1 above. If the target cell moderately expresses the receptor, then the ligand-drug particle may have a valency of 12-23 ligands per particle, based on Table 1 above. The specific valency or valency range may depend further on the $K_D$ of the ligand for its receptor. For example, from Table 1, if the ligand-receptor $K_D$ is on the order of 10 nM (i.e., a value rounding closest to 10 nM), and the receptor is highly expressed as defined above, then the particle may have a valency of 15-17, or may have a valency of 15, 16, or 17, or of 16. From Table 1, if the ligand-receptor $K_D$ is on the order of 1 nM (i.e., a value rounding closest to 1 nM), and the receptor is moderately expressed as defined above, then the particle may have a valency of 16-18, or may have a valency of 16, 17 or 18, or of 17. From Table 2, if the ligand-receptor $K_D$ is on the order of 0.1 nM (i.e., a value rounding closest to 0.1 nM), and the receptor is expressed at an average on the order of $7 \times 10^5$, then the particle may have a valency of 14-16, or may have a valency of 14, 15, or 16, or of 15. Similar valencies may be determined for a ligand-drug particle embodiment herein for all of the other combinations of $R_T$ and $K_D$ shown in Tables 1 and 2.

Thus, in some embodiments, where the receptor-ligand equilibrium dissociation constant, measured in vitro, is 0.001 to 1000 nM, the particle has a ligand valency as follows: (a) a valency of 6-12 where the target cell has an average on the order of $3 \times 10^6$ receptors per cell; (b) a valency of 10-19 where the target cell has an average on the order of $1 \times 10^6$ receptors per cell; (c) a valency of 10-20 where the target cell has an average on the order of $9 \times 10^5$ receptors per cell; (d) a valency of 11-21 where the target cell has an average on the order of $8 \times 10^5$ receptors per cell; (e) a valency of 12-23 where the target cell has an average on the order of $7 \times 10^5$ receptors per cell; (f) a valency of 13-25 where the target cell has an average on the order of $6 \times 10^5$ receptors per cell; (g) a valency of 15-29 where the target cell has an average on the order of $5 \times 10^5$ receptors per cell; or (h) a valency of 18-36 where the target cell has an average on the order of $4 \times 10^5$ receptors per cell. In some such embodiments, the ligand-receptor equilibrium dissociation constant, measured in vitro, is 0.1 to 10 nM and the particle has a ligand valency as follows: (a) a valency of 8-10 where the target cell has an on the order of $3 \times 10^6$ receptors per cell; (b) a valency of 13-16 where the target cell has an average on the order of $9 \times 10^5$ to $1 \times 10^6$ receptors per cell; (c) a valency of 14-18 where the target cell has an average on the order of $8 \times 10^5$ receptors per cell; (d) a valency of 15-19 where the target cell has an average on the order of $7 \times 10^5$ receptors per cell; (e) a valency of 17-21 where the target cell has an average on the order of $6 \times 10^5$ receptors per cell; (f) a valency of 19-24 where the target cell has an average on the order of $5 \times 10^5$ receptors per cell; or (g) a valency of 24-30 where the target cell has an average on the order of $4 \times 10^5$ receptors per cell.

In some such embodiments, the ligand-receptor equilibrium dissociation constant, measured in vitro, is 0.01 to 0.1 nM and the particle has a ligand valency as follows: (a) a valency of 7-8 where the target cell has an on the order of $3 \times 10^6$ receptors per cell; (b) a valency of 11-13 where the target cell has an average on the order of $9 \times 10^5$ receptors per cell; (c) a valency of 12-13 where the target cell has an average on the order of $1 \times 10^6$ receptors per cell; (d) a valency of 12-14 where the target cell has an average on the order of $8 \times 10^5$ receptors per cell; (e) a valency of 13-15 where the target cell has an average on the order of $7 \times 10^5$ receptors per cell; (f) a valency of 15-17 where the target cell has an average on the order of $6 \times 10^5$ receptors per cell; (g) a valency of 17-19 where the target cell has an average on the order of $5 \times 10^5$ receptors per cell; or (h) a valency of 21-24 where the target cell has an average on the order of $4 \times 10^5$ receptors per cell. In some embodiments, the ligand-receptor equilibrium dissociation constant, measured in vitro, is 0.1 to 1 nM and the particle has a ligand valency as follows: (a) a valency of 8-9 where the target cell has an on the order of $3 \times 10^6$ receptors per cell; (b) a valency of 13-14 where the target cell has an average on the order of $9 \times 10^5$ receptors per cell; (c) a valency of 13-15 where the target cell has an average on the order of $1 \times 10^6$ receptors per cell; (d) a valency of 14-16 where the target cell has an average on the order of $8 \times 10^5$ receptors per cell; (e) a valency of 15-17 where the target cell has an average on the order of $7 \times 10^5$ receptors per cell; (f) a valency of 17-19 where the target cell has an average on the order of $6 \times 10^5$ receptors per cell; (g) a valency of 19-22 where the target cell has an average on the order of $5 \times 10^5$ receptors per cell; or (h) a valency of 24-27 where the target cell has an average on the order of $4 \times 10^5$ receptors per cell. In some embodiments, the ligand-receptor equilibrium dissociation constant, measured in vitro, is 1 to 10 nM and the particle has a ligand valency as follows: (a) a valency of 9-10 where the target cell has an on the order of $3 \times 10^6$ receptors per cell; (b) a valency of 14-16 where the target cell has an average on the order of $9 \times 10^5$ receptors per cell; (c) a valency of 15-16 where the target cell has an average on the order of $1 \times 10^6$ receptors per cell; (d) a valency of 16-18 where the target cell has an average on the order of $8 \times 10^5$ receptors per cell; (e) a valency of 17-19 where the target cell has an average on the order of $7 \times 10^5$ receptors per cell; (f) a valency of 19-21 where the target cell has an average on the order of $6 \times 10^5$ receptors per cell; (g) a valency of 22-24 where the target cell has an average on the order of $5 \times 10^5$ receptors per cell; or (h) a valency of 27-30 where the target cell has an average on the order of $4 \times 10^5$ receptors per cell. In some embodiments, the ligand-receptor equilibrium dissociation constant, measured in vitro, is 10 to 100 nM and the particle has a ligand valency as follows: (a) a valency of 10-11 where the target cell has an on the order of $3 \times 10^6$ receptors per cell; (b) a valency of 16-17 where the target cell has an average on the order of $9 \times 10^5$ receptors per cell; (c) a valency of 16-18 where the target cell has an average on the order of $1 \times 10^6$ receptors per cell; (d) a valency of 18-19 where the target cell has an average on the order of $8 \times 10^5$ receptors per cell; (e) a valency of 19-21 where the target cell has an average on the order of $7 \times 10^5$ receptors per cell; (f) a valency of 21-23 where the target cell has an average on the order of $6 \times 10^5$ receptors per cell; (g) a valency of 24-27 where the target cell has an average on the order of $5 \times 10^5$ receptors per cell; or (h) a valency of 30-33 where the target cell has an average on the order of $4 \times 10^5$ receptors per cell.

In further embodiments, the ligand-drug particle has a ligand-receptor in vitro binding affinity is 0.001 to 0.1 nM and the particle has a ligand valency as follows, depending on the number of receptors per cell: (a) a valency of 15-24 where the target cell has an average on the order of $4 \times 10^5$ to $5 \times 10^5$ receptors per cell; (b) a valency of 13-19 where the target cell has an average on the order of $5 \times 10^5$ to $6 \times 10^5$ receptors per cell; (c) a valency of 12-17 where the target cell has an average on the order of $6 \times 10^5$ to $7 \times 10^5$ receptors per cell; (d) a valency of 11-15 where the target cell has an average on the order of $7 \times 10^5$ to $8 \times 10^5$ receptors per cell; (e) a valency of 10-14 where the target cell has an average on the order of $8 \times 10^5$ to $9 \times 10^5$ receptors per cell; (f) a valency of 10-13 where the target cell has an average on the order of $9 \times 10^5$ to $1 \times 10^6$ receptors per cell; or (g) a valency of 6-13 where the target cell has an average on the order of $1 \times 10^6$ to $3 \times 10^6$ receptors per cell. In additional embodiments, the ligand-receptor in vitro binding affinity is 0.1 to 10 nM and the particle has a ligand valency as follows: (a) a valency of 19-30 where the target cell has an average on the order of $4 \times 10^5$ to $5 \times 10^5$ receptors per cell; (b) valency of 17-24 where the target cell has an average on the order of $5 \times 10^5$ to $6 \times 10^5$ receptors per cell; (c) a valency of 15-21 where the target cell has an average on the order of $6 \times 10^5$ to $7 \times 10^5$ receptors per cell; (d) a valency of 14-19 where the target cell has an average on the order of $7 \times 10^5$ to $8 \times 10^5$ receptors per cell; (d a valency of 13-18 where the target cell has an average on the order of $8 \times 10^5$ to $9 \times 10^5$ receptors per cell; (f) a valency of 13-16 where the target cell has an average on the order of $9 \times 10^5$ to $1 \times 10^6$ receptors per cell; or (g) a valency of 8-16 where the target cell has an average on the order of $1 \times 10^6$ to $3 \times 10^6$ receptors per cell. In yet other embodiments, the ligand-receptor in vitro binding affinity is 10 to 1000 nM and the particle has a ligand valency as follows: (a) valency of 24-36 where the target cell has an average on the order of $4 \times 10^5$ to $5 \times 10^5$ receptors per cell; (b) a valency of 21-29 where the target cell has an average on the order of $5 \times 10^5$ to $6 \times 10^5$ receptors per cell; (c) a valency of 19-25 where the target cell has an average on the order of $6 \times 10^5$ to $7 \times 10^5$ receptors per cell; (d) a valency of 18-23 where the target cell has an average on the order of $7 \times 10^5$ to $8 \times 10^5$ receptors per cell; (e) a valency of 16-21 where the target cell has an average on the order of $8 \times 10^5$ to $9 \times 10^5$ receptors per cell; (f) a valency of 16-20 where the target cell has an average on the order of $9 \times 10^5$ to $1 \times 10^6$ receptors per cell; or (g) a valency of 10-19 where the target cell has an average on the order of $1 \times 10^6$ to $3 \times 10^6$ receptors per cell.

In embodiments where the expression level of the receptor is such that there is an average of on the order of $4 \times 10^5$ receptors per cell, then, based on Table 2, the ligand valency may be (a) 35-37; or 35, 36, or 37; or 36 if the ligand-receptor $K_D$ is on the order of 1000 nM; (b) 32-34; or 32, 33, or 34; or 33 if the ligand-receptor $K_D$ is on the order of 100 nM; (c) 29-31; or 29, 30, or 31; or 30 if the ligand-receptor $K_D$ is on the order of 10 nM; (d) 26-28; or 26, 27, 28; or 27 if the ligand-receptor $K_D$ is on the order of 1 nM; (e) 23-25; or 23, 24, or 25; or 24 if the ligand-receptor $K_D$ is on the order of 0.1 nM; (f) 20-22; or 20, 21, or 22; or 21 if the ligand-receptor $K_D$ is on the order of 0.01 nM; or (g) 17-19; or 17, 18, or 19; or 18 if the ligand-receptor $K_D$ is on the order of 0.001 nM.

In embodiments where the expression level of the receptor is such that there is an average of on the order of $5 \times 10^5$ receptors per cell, then, based on Table 2, the ligand valency may be (a) 28-30; or 28, 29, or 30; or 29 if the ligand-receptor $K_D$ is on the order of 1000 nM; (b) 26-28; or 26, 27, or 28; or 27 if the ligand-receptor $K_D$ is on the order of 100 nM; (c) 23-25; or 23, 24, or 25; or 24 if the ligand-receptor $K_D$ is on the order of 10 nM; (d) 21-23; or 21, 22, or 23; or 22 if the ligand-receptor $K_D$ is on the order of 1 nM; (e) 18-20; or 18, 19, or 20; or 19 if the ligand-receptor $K_D$ is on the order of 0.1 nM; (f) 16-18; or 16, 17, or 18; or 17 if the ligand-receptor $K_D$ is on the order of 0.01 nM; or (g) 14-16; or 14, 15, or 16; or 15 if the ligand-receptor $K_D$ is on the order of 0.001 nM.

In embodiments where the expression level of the receptor is such that there is an average of on the order of $6 \times 10^5$ receptors per cell, then, based on Table 2, the ligand valency may be (a) 24-26; or 24, 25, or 26; or 25 if the ligand-receptor $K_D$ is on the order of 1000 nM; (b) 22-24; or 22, 23, or 24; or 23 if the ligand-receptor $K_D$ is on the order of 100 nM; (c) 20-22; or 20, 21, or 22; or 21 if the ligand-receptor $K_D$ is on the order of 10 nM; (d) 18-20; or 18, 19, or 20; or 19 if the ligand-receptor $K_D$ is on the order of 1 nM; (e) 16-18; or 16, 17, or 18; or 17 if the ligand-receptor $K_D$ is on the order of 0.1 nM; (f) 14-16; or 14, 15, or 16; or 15 if the ligand-receptor $K_D$ is on the order of 0.01 nM; or (g) 12-14; or 12, 13, or 14; or 13 if the ligand-receptor $K_D$ is on the order of 0.001 nM.

In embodiments where the expression level of the receptor is such that there is an average of on the order of $7 \times 10^5$ receptors per cell, then, based on Table 2, the ligand valency may be (a) 22-24; or 22, 23, or 24; or 23 if the ligand-receptor $K_D$ is on the order of 1000 nM; (b) 20-22; or 20, 21, or 22; or 21 if the ligand-receptor $K_D$ is on the order of 100 nM; (c) 18-20; or 18, 19, or 20; or 19 if the ligand-receptor $K_D$ is on the order of 10 nM; (d) 16-18; or 16, 17, or 18; or 17 if the ligand-receptor $K_D$ is on the order of 1 nM; (e) 14-16; or 14, 15, or 16; or 15 if the ligand-receptor $K_D$ is on the order of 0.1 nM; (f) 12-14; or 12, 13, or 14; or 13 if the ligand-receptor $K_D$ is on the order of 0.01 nM; or (g) 11-13; or 11, 12, or 13; or 12 if the ligand-receptor $K_D$ is on the order of 0.001 nM.

In embodiments where the expression level of the receptor is such that there is an average of on the order of $8 \times 10^5$ receptors per cell, then, based on Table 2, the ligand valency may be (a) 20-22; or 20, 21, or 22; or 21 if the ligand-receptor $K_D$ is on the order of 1000 nM; (b) 18-20; or 18, 19, or 20; or 19 if the ligand-receptor $K_D$ is on the order of 100 nM; (c) 17-19; or 17, 18, or 19; or 18 if the ligand-receptor $K_D$ is on the order of 10 nM; (d) 15-17; or 15, 16, or 17; or 16 if the ligand-receptor $K_D$ is on the order of 1 nM; (e) 13-15; or 13, 14, or 15; or 14 if the ligand-receptor $K_D$ is on the order of 0.1 nM; (f) 11-13; or 11, 12, or 13; or 12 if the ligand-receptor $K_D$ is on the order of 0.01 nM; or (g) 10-12; or 10, 11, or 12; or 11 if the ligand-receptor $K_D$ is on the order of 0.001 nM.

In embodiments where the expression level of the receptor is such that there is an average of on the order of $9 \times 10^5$ receptors per cell, then, based on Table 2, the ligand valency may be (a) 19-21; or 19, 20, or 21; or 20 if the ligand-receptor $K_D$ is on the order of 1000 nM; (b) 17-19; or 17, 18, or 19; or 18 if the ligand-receptor $K_D$ is on the order of 100 nM; (c) 15-17; or 15, 16, or 17; or 16 if the ligand-receptor $K_D$ is on the order of 10 nM; (d) 14-16; or 14, 15, or 16; or 15 if the ligand-receptor $K_D$ is on the order of 1 nM; (e) 12-14; or 12, 13, or 14; or 13 if the ligand-receptor $K_D$ is on the order of 0.1 nM; (f) 11-13; or 11, 12, or 13; or 12 if the ligand-receptor $K_D$ is on the order of 0.01 nM; or (g) 9-11; or 9, 10, or 11; or 10 if the ligand-receptor $K_D$ is on the order of 0.001 nM.

In embodiments where the expression level of the receptor is such that there is an average of on the order of $1 \times 10^6$ receptors per cell, then, based on Table 2, the ligand valency may be (a) 18-20; or 18, 19, or 20; or 19 if the ligand-receptor $K_D$ is on the order of 1000 nM; (b) 16-18; or 16, 17, or 18; or 17 if the ligand-receptor $K_D$ is on the order of 100 nM; (c) 15-17; or 15, 16, or 17; or 16 if the ligand-receptor $K_D$ is on the order of 10 nM; (d) 13-15; or 13, 14, or 15; or 14 if the ligand-receptor $K_D$ is on the order of 1 nM; (e) 12-14; or 12, 13, or 14; or 13 if the ligand-receptor $K_D$ is on the order of 0.1 nM; (f) 10-12; or 10, 11, or 12; or 11 if the ligand-receptor $K_D$ is on the order of 0.01 nM; or (g) 9-11; or 9, 10, or 11; or 10 if the ligand-receptor $K_D$ is on the order of 0.001 nM.

In embodiments where the expression level of the receptor is such that there is an average of on the order of $3 \times 10^6$ receptors per cell, then, based on Table 2, the ligand valency may be (a) 11-13; or 11, 12, or 13; or 12 if the ligand-receptor $K_D$ is on the order of 1000 nM; (b) 10-12; or 10, 11, or 12; or 11 if the ligand-receptor $K_D$ is on the order of 100 nM; (c) 9-11; or 9, 10, or 11; or 10 if the ligand-receptor $K_D$ is on the order of 10 nM; (d) 8-10; or 8, 9, or 10; or 9 if the ligand-receptor $K_D$ is on the order of 1 nM; (e) 7-9; or 7, 8, or 9; or 8 if the ligand-receptor $K_D$ is on the order of 0.1 nM; (f) 6-8; or 6, 7, or 8; or 7 if the ligand-receptor $K_D$ is on the order of 0.01 nM; or (g) 5-7; or 5, 6, or 7; or 6 if the ligand-receptor $K_D$ is on the order of 0.001 nM.

Particles with Two Ligands, Each Recognizing a Different Receptor

Also contemplated herein are ligand-drug particles that comprise two different ligands, specific for two different receptors on a target cell. Such ligand-drug particles may comprise a lipid surface layer, at least one drug in the interior of the particle or embedded in the lipid surface layer, and two ligands specific for two different cell surface receptors on a target cell, wherein the ligands are exposed on the lipid surface layer; the ligands bind to their receptors with in vitro binding affinity of 0.1 to 100 nM; the target cell that the particle targets comprises an average on the order of $10^3$ to $10^7$ of each receptor; and the particle has a ligand valency that depends upon the ligand-receptor in vitro binding affinity or each receptor-ligand pair, the average number of each receptor per target cell, and whether ligand-receptor binding is additive or synergistic.

In some embodiments, in a dual-ligand particle, at least one ligand is an antibody, or both ligands are antibodies. In some embodiments, at least one ligand is an antigen binding fragment of an antibody, or both ligands are antigen binding fragments of antibodies, such as an Fv, scFv, Fab', or F(ab')$_2$ fragment.

Table 3 below (also in the Examples below) provides calculated optimal valence of each ligand for particles with two different ligand species specific for two different receptors with high expression or moderate expression in the target cell, the valence also depending on the in vitro equilibrium dissociation constant of the ligand and receptor, and on whether the interaction between the ligands and receptors on the target cell is observed to be additive or synergistic. The valence, in Table 3 below refers to the valence of each ligand per particle. Thus, for example, if the table indicates an optimal valency of, say, 16, the valency would be 16 for each of the two ligands for a total ligand valency of 32.

TABLE 3

Optimal Valance for Each Ligand on Particles with Two Ligands under Different Receptor Expression and Ligand-Receptor Affinity Conditions Optimal Multi-Valent Binding: Dual-Targeted

| $K_D$ (nM) | | Valence (Ligands/Particle) | | | | | |
|---|---|---|---|---|---|---|---|
| Ligand 1 | Ligand 2 | HHa | HMa | MMa | HHs | HMs | MMs |
| 100 | 100 | 17 | 17 | 21 | 13 | 10 | 15 |
| 100 | 10 | 16 | 17 | 20 | 13 | 10 | 15 |
| 100 | 1 | 16 | 17 | 19 | 13 | 10 | 15 |
| 100 | 0.1 | 15 | 17 | 19 | 13 | 10 | 15 |
| 10 | 10 | 16 | 16 | 19 | 12 | 9 | 13 |
| 10 | 1 | 15 | 16 | 18 | 12 | 9 | 13 |
| 10 | 0.1 | 14 | 16 | 17 | 12 | 9 | 13 |
| 1 | 1 | 14 | 14 | 17 | 10 | 8 | 12 |
| 1 | 0.1 | 13 | 14 | 16 | 10 | 8 | 12 |
| 0.1 | 0.1 | 13 | 13 | 15 | 9 | 7 | 11 |

Table 3, which is also provided in the Examples below, provides optimal valence for each ligand calculated based on particular sets of ligand equilibrium dissociation constants and the expression levels of each receptor (high (H) on the order of $1 \times 10^6$ or moderate (M) on the order of $1 \times 10^5$) and whether the binding is additive (a) or synergistic (s).

In some embodiments where a particle has two ligands, the particle has a ligand valency as follows: (a) a valency of 13-17 where each receptor is highly expressed by the target cell and where binding of the two receptors by the two ligands is additive (HHa in Table 3); (b) valency of 9-13 where each receptor is highly expressed by the target cell and where binding of the two receptors by the two ligands is synergistic (HHs); (c) a valency of 13-17 where one receptor is highly expressed by the target cell and the other receptor is moderately expressed, and where binding of the two receptors by the two ligands is additive (HMa); (d) a valency of 7-10 where one receptor is highly expressed by the target cell and the other receptor is moderately expressed, and where binding of the two receptors by the two ligands is synergistic (HMs); (e) a valency of 15-21 where each receptor is moderately expressed by the target cell and where binding of the two receptors by the two ligands is additive (MMa); or (f) a valency of 11-15 where each receptor is moderately expressed by the target cell and where binding of the two receptors by the two ligands is synergistic (MMs).

In some embodiments, the dual-ligand particle has a ligand valency as follows: (a) a valency of 17-21 where the in vitro binding affinity for each ligand-receptor pair is on the order of 100 nM and binding is additive; (b) a valency of 16-20 where the in vitro binding affinity for one ligand-receptor pair is on the order of 100 nM for the second ligand-receptor pair is on the order of 10 nM and binding is additive; (c) a valency of 16-19 where the in vitro binding affinity for one ligand-receptor pair is on the order of 100 nM for the second ligand-receptor pair is on the order of 1 nM and binding is additive; (d) a valency of 15-19 where the in vitro binding affinity for one ligand-receptor pair is on the order of 100 nM for the second ligand-receptor pair is on the order of 0.1 nM and binding is additive; (e) a valency of 16-19 where the in vitro binding affinity for each ligand-receptor pair is on the order of 10 nM and binding is additive; (f) a valency of 15-18 where the in vitro binding affinity for one ligand-receptor pair is on the order of 10 nM for the second ligand-receptor pair is on the order of 1 nM and binding is additive; (g) a valency of 14-17 where the in vitro binding affinity for one ligand-receptor pair is on the order of 10 nM for the second ligand-receptor pair is on the order of 0.1 nM and binding is additive; (h) a valency of 14-17 where the in vitro binding affinity for each ligand-receptor pair is on the order of 1 nM and binding is additive; (i) a valency of 13-16 where the in vitro binding affinity for one ligand-receptor pair is on the order of 1 nM for the second ligand-receptor pair is on the order of 0.1 nM and binding is additive; (j) a valency of 13-15 where the in vitro binding affinity for each ligand-receptor pair is on the order of 0.1 nM and binding is additive; (k) a valency of 10-15 where the in vitro binding affinity for each ligand-receptor pair is on the order of 100 nM and binding is synergistic; (l) a valency of 10-15 where the in vitro binding affinity for one ligand-receptor pair is on the order of 100 nM for the second ligand-receptor pair is on the order of 10 nM and binding is synergistic; (m) a valency of 10-15 where the in vitro binding affinity for one ligand-receptor pair is on the order of 100 nM for the second ligand-receptor pair is on the order of 1 nM and binding is synergistic; (n) a valency of 10-15 where the in vitro binding affinity for one ligand-receptor pair is on the order of 100 nM for the second ligand-receptor pair is on the order of 0.1 nM and binding is synergistic; (o) a valency of 9-13 where the in vitro binding affinity for each ligand-receptor pair is on the order of 10 nM and binding is synergistic; (p) a valency of 9-13 where the in vitro binding affinity for one ligand-receptor pair is on the order of 10 nM for the second ligand-receptor pair is on the order of 1 nM and binding is synergistic; (q) a valency of 9-13 where the in vitro binding affinity for one ligand-receptor pair is on the order of 10 nM for the second ligand-receptor pair is on the order of 0.1 nM and binding is synergistic; (r) a valency of 8-12 where the in vitro binding affinity for each ligand-receptor pair is on the order of 1 nM and binding is synergistic; (s) a valency of 8-12 where the in vitro binding affinity for one ligand-receptor pair is on the order of 1 nM for the second ligand-receptor pair is on the order of 0.1 nM and binding is synergistic; or (t) a valency of 7-11 where the in vitro binding affinity for each ligand-receptor pair is on the order of 0.1 nM and binding is synergistic.

In some embodiments, the dual-ligand particle has a ligand valency as follows, where the target cell highly expresses both receptors: (a) a valency of 16-18; or 16, 17, or 18; or 17, where the in vitro binding affinity for each ligand-receptor pair is on the order of 100 nM and binding is additive; (b) a valency of 15-17; or 15, 16, or 17; or 16, where the in vitro binding affinity for one ligand-receptor pair is on the order of 100 nM for the second ligand-receptor pair is on the order of 10 nM and binding is additive; (c) a valency of 15-17; or 15, 16, or 17; or 16, where the in vitro binding affinity for one ligand-receptor pair is on the order of 100 nM for the second ligand-receptor pair is on the order of 1 nM and binding is additive; (d) a valency of 14-16; or 14, 15, or 16; or 15, where the in vitro binding affinity for one ligand-receptor pair is on the order of 100 nM for the second ligand-receptor pair is on the order of 0.1 nM and binding is additive; (e) a valency of 15-17; or 15, 16, or 17; or 16, where the in vitro binding affinity for each ligand-receptor pair is on the order of 10 nM and binding is additive; (f) a valency of 14-16; or 14, 15, or 16; or 15, where the in vitro binding affinity for one ligand-receptor pair is on the order of 10 nM for the second ligand-receptor pair is on the order of 1 nM and binding is additive; (g) a valency of 13-15; or 13, 14, or 15; or 14, where the in vitro binding affinity for one ligand-receptor pair is on the order of 10 nM for the second ligand-receptor pair is on the order of 0.1 nM and binding is additive; (h) a valency of 13-15; or 13, 14, or 15; or 14, where the in vitro binding affinity for each ligand-receptor pair is on the order of 1 nM and binding is additive; (i) a valency of 12-14; 12, 13, or 14; or 13, where the in vitro binding affinity for one ligand-receptor pair is on the order of 1 nM for the second ligand-receptor pair is on the order of 0.1 nM and binding is additive; (j) a valency of 12-14; 12, 13, or 14; or 13, where the in vitro binding affinity for each ligand-receptor pair is on the order of 0.1 nM and binding is additive; (k) a valency of 12-14; 12, 13, or 14; or 13, where the in vitro binding affinity for each ligand-receptor pair is on the order of 100 nM and binding is synergistic; (l) a valency of 12-14; 12, 13, or 14; or 13, where the in vitro binding affinity for one ligand-receptor pair is on the order of 100 nM for the second ligand-receptor pair is on the order of 10 nM and binding is synergistic; (m) a valency of 12-14; 12, 13, or 14; or 13, where the in vitro binding affinity for one ligand-receptor pair is on the order of 100 nM for the second ligand-receptor pair is on the order of 1 nM and binding is synergistic; (n) a valency of 12-14; 12, 13, or 14; or 13, where the in vitro binding affinity for one ligand-receptor pair is on the order of 100 nM for the second ligand-receptor pair is on the order of 0.1 nM and binding is synergistic; (o) a valency of 11-13; 11, 12, or 13; or 12, where the in vitro binding affinity for each ligand-receptor pair is on the order of 10 nM and binding is synergistic; (p) a valency of 11-13; 11, 12, or 13; or 12, where the in vitro binding affinity for one ligand-receptor pair is on the order of 10 nM for the second ligand-receptor pair is on the order of 1 nM and binding is synergistic; (q) a valency of 11-13; 11, 12, or 13; or 12, where the in vitro binding affinity for one ligand-receptor pair is on the order of 10 nM for the second ligand-receptor pair is on the order of 0.1 nM and binding is synergistic; (r) a valency of 9-11; 9, 10, or 11; or 10, where the in vitro binding affinity for each ligand-receptor pair is on the order of 1 nM and binding is synergistic; (s) a valency of 9-11; 9, 10, or 11; or 10, where the in vitro binding affinity for one ligand-receptor pair is on the order of 1 nM for the second ligand-receptor pair is on the order of 0.1 nM and binding is synergistic; or (t) a valency of 8-10; 8, 9, or 10; or 9, where the in vitro binding affinity for each ligand-receptor pair is on the order of 0.1 nM and binding is synergistic.

In some embodiments, the dual-ligand particle has a ligand valency as follows, where the target cell moderately expresses both receptors: (a) a valency of 20-22; or 20, 21, or 22; or 21, where the in vitro binding affinity for each ligand-receptor pair is on the order of 100 nM and binding is additive; (b) a valency of 19-21; or 19, 20, or 21; or 20, where the in vitro binding affinity for one ligand-receptor pair is on the order of 100 nM for the second ligand-receptor pair is on the order of 10 nM and binding is additive; (c) a valency of 18-20; or 18, 19, or 20; or 19, where the in vitro binding affinity for one ligand-receptor pair is on the order of 100 nM for the second ligand-receptor pair is on the order of 1 nM and binding is additive; (d) a valency of 18-20; or 18, 19, or 20; or 19, where the in vitro binding affinity for one ligand-receptor pair is on the order of 100 nM for the second ligand-receptor pair is on the order of 0.1 nM and binding is additive; (e) a valency of 18-20; or 18, 19, or 20; or 19, where the in vitro binding affinity for each ligand-receptor pair is on the order of 10 nM and binding is additive; (f) a valency of 17-19; or 17, 18, or 19; or 18, where the in vitro binding affinity for one ligand-receptor pair is on the order of 10 nM for the second ligand-receptor pair is on the order of 1 nM and binding is additive; (g) a valency of 16-18; or 16, 17, 18; or 17, where the in vitro binding affinity for one ligand-receptor pair is on the order of 10 nM for the second ligand-receptor pair is on the order of 0.1 nM and binding is additive; (h) a valency of 16-18; or 16, 17, 18; or 17, where the in vitro binding affinity for each ligand-receptor pair is on the order of 1 nM and binding is additive; (i) a valency of 15-17; or 15, 16, or 17; or 16, where the in vitro binding affinity for one ligand-receptor pair is on the order of 1 nM for the second ligand-receptor pair is on the order of 0.1 nM and binding is additive; (j) a valency of 14-16; or 14, 15, or 16; or 15; where the in vitro binding affinity for each ligand-receptor pair is on the order of 0.1 nM and binding is additive; (k) a valency of 14-16; or 14, 15, or 16; or 15; where the in vitro binding affinity for each ligand-receptor pair is on the order of 100 nM and binding is synergistic; (l) a valency of 14-16; or 14, 15, or 16; or 15; where the in vitro binding affinity for one ligand-receptor pair is on the order of 100 nM for the second ligand-receptor pair is on the order of 10 nM and binding is synergistic; (m) a valency of 14-16; or 14, 15, or 16; or 15; where the in vitro binding affinity for one ligand-receptor pair is on the order of 100 nM for the second ligand-receptor pair is on the order of 1 nM and binding is synergistic; (n) a valency of 14-16; or 14, 15, or 16; or 15; where the in vitro binding affinity for one ligand-receptor pair is on the order of 100 nM for the second ligand-receptor pair is on the order of 0.1 nM and binding is synergistic; (o) a valency of 12-14; or 12, 13, or 14; or 13, where the in vitro binding affinity for each ligand-receptor pair is on the order of 10 nM and binding is synergistic; (p) a valency of 12-14; or 12, 13, or 14; or 13, where the in vitro binding affinity for one ligand-receptor pair is on the order of 10 nM for the second ligand-receptor pair is on the order of 1 nM and binding is synergistic; (q) a valency of 12-14; or 12, 13, or 14; or 13, where the in vitro binding affinity for one ligand-receptor pair is on the order of 10 nM for the second ligand-receptor pair is on the order of 0.1 nM and binding is synergistic; (r) a valency of 11-13; or 11, 12, or 13; or 12, where the in vitro binding affinity for each ligand-receptor pair is on the order of 1 nM and binding is synergistic; (s) a valency of 11-13; or 11, 12, or 13; or 12, where the in vitro binding affinity for one ligand-receptor pair is on the order of 1 nM for the second ligand-receptor pair is on the order of 0.1 nM and binding is synergistic; or (t) a valency of 10-12; or 10, 11, or 12; or 11, where the in vitro binding affinity for each ligand-receptor pair is on the order of 0.1 nM and binding is synergistic.

In some embodiments, the dual-ligand particle has a ligand valency as follows, where the target cell highly expresses one receptor and moderately expresses the other: (a) a valency of 16-18; or 16, 17, or 18; or 17, where the in vitro binding affinity for each ligand-receptor pair is on the order of 100 nM and binding is additive; (b) a valency of 16-18; or 16, 17, or 18; or 17, where the in vitro binding affinity for one ligand-receptor pair is on the order of 100 nM for the second ligand-receptor pair is on the order of 10 nM and binding is additive; (c) a valency of 16-18; or 16, 17, or 18; or 17, where the in vitro binding affinity for one ligand-receptor pair is on the order of 100 nM for the second ligand-receptor pair is on the order of 1 nM and binding is additive; (d) a valency of 16-18; or 16, 17, or 18; or 17, where the in vitro binding affinity for one ligand-receptor pair is on the order of 100 nM for the second ligand-receptor pair is on the order of 0.1 nM and binding is additive; (e) a valency of 15-17; or 15, 16, or 17; or 16, where the in vitro binding affinity for each ligand-receptor pair is on the order of 10 nM and binding is additive; (f) a valency of 15-17; or 15, 16, or 17; or 16, where the in vitro binding affinity for one ligand-receptor pair is on the order of 10 nM for the second ligand-receptor pair is on the order of 1 nM and binding is additive; (g) a valency of 15-17; or 15, 16, or 17; or 16, the in vitro binding affinity for one ligand-receptor pair is on the order of 10 nM for the second ligand-receptor pair is on the order of 0.1 nM and binding is additive; (h) a valency of 13-15; or 13, 14, or 15; or 14, where the in vitro binding affinity for each ligand-receptor pair is on the order of 1 nM and binding is additive; (i) a valency of 13-15; or 13, 14, or 15; or 14, where the in vitro binding affinity for one ligand-receptor pair is on the order of 1 nM for the second ligand-receptor pair is on the order of 0.1 nM and binding is additive; (j) a valency of 12-14; 12, 13, or 14; or 13, where the in vitro binding affinity for each ligand-receptor pair is on the order of 0.1 nM and binding is additive; (k) a valency of 9-11; or 9, 10, or 11; or 10, where the in vitro binding affinity for each ligand-receptor pair is on the order of 100 nM and binding is synergistic; (l) a valency of 9-11; or 9, 10, or 11; or 10, where the in vitro binding affinity for one ligand-receptor pair is on the order of 100 nM for the second ligand-receptor pair is on the order of 10 nM and binding is synergistic; (m) a valency of 9-11; or 9, 10, or 11; or 10, where the in vitro binding affinity for one ligand-receptor pair is on the order of 100 nM for the second ligand-receptor pair is on the order of 1 nM and binding is synergistic; (n) a valency of 9-11; or 9, 10, or 11; or 10, the in vitro binding affinity for one ligand-receptor pair is on the order of 100 nM for the second ligand-receptor pair is on the order of 0.1 nM and binding is synergistic; (o) a valency of 8-10; or 8, 9, or 10; or 9, where the in vitro binding affinity for each ligand-receptor pair is on the order of 10 nM and binding is synergistic; (p) a valency of 8-10; or 8, 9, or 10; or 9, where the in vitro binding affinity for one ligand-receptor pair is on the order of 10 nM for the second ligand-receptor pair is on the order of 1 nM and binding is synergistic; (q) a valency of 8-10; or 8, 9, or 10; or 9, where the in vitro binding affinity for one ligand-receptor pair is on the order of 10 nM for the second ligand-receptor pair is on the order of 0.1 nM and binding is synergistic; (r) a valency of 7-9; or 7, 8, or 9; or 8, where the in vitro binding affinity for each ligand-receptor pair is on the order of 1 nM and binding is synergistic; (s) a valency of 7-9; or 7, 8, or 9; or 8, where the in vitro binding affinity for one ligand-receptor pair is on the order of 1 nM for the second ligand-receptor pair is on the order of 0.1 nM and binding is synergistic; or (t) a valency of 6-8; or 6, 7, or 8; or 7, where the in vitro binding affinity for each ligand-receptor pair is on the order of 0.1 nM and binding is synergistic.

In some embodiments, the equilibrium dissociation constant for a particular ligand will have been previously measured in vitro, and this information may be used to obtain an optimal ligand valence for a particle comprising that ligand. For instance, some reported equilibrium dissociation constants for potential ligand molecules include: abciximab 5 nM, adalimumab 0.05-0.1 nM, alemtuzumab 3-10 nM, atezolizumab 0.4 nM, avelumab 0.7 nM, basiliximab 0.1 nM, belimumab 0.1-0.3 nM, benralizumab 0.016 nM, bevacizumab 0.5-20 nM, bezlotoxumab 0.02-0.04 nM, blinatumomab 1.5 nM, brentuximab 0.2 nM, brodalumab 0.24 nM, canakinumab 0.02-1.3 nM, certolizumab 0.09 nM, cetuximab 0.1-0.4 nM, daclizumab 0.3-0.5 nM, daratumumab 4.4 nM, denosumab 0.003 nM, dinutuximab 11-12 nM, dupilumab 0.01-0.03 nM, durvalumab 0.022 nM, eculizumab 0.12 nM, elotuzumab 30-45 nM, emicizumab 900-1800 nM, evolocumab 0.016 nM, golimumab 0.018 nM, ibritumomab 17 nM, idarucizumab 0.0021 nM, infliximab 0.1-0.45 nM, inotuzumab 0.12-0.15 nM, ipilimumab 1-10 nM, ixekizumab 0.0018 nM, mepolizumab 0.0042 nM, natalizumab 0.3 nM, necitumumab 0.32 nM, nivolumab 2-3 nM, obiltoxaximab 0.33 nM, obinutuzumab 4 nM, ocrelizumab 0.47-1.2 nM, ofatumumab 3-6 nM, olaratumab 0.33 nM, omalizumab 2-8 nM, palivizumab 1 nM, panitumumab 0.05 nM, pembrolizumab 0.029 nM, pertuzumab 9-15 nM, ramucirumab 0.05 nM, ranibizumab 0.19 nM, raxibacumab 1-4 nM, reslizumab 0.081 nM, rituximab 5-11 nM, sarilumab 0.054 nM, secukinumab 0.06-0.37 nM, siltuximab 0.034 nM, tocilizumab 1-3 nM, trastuzumab 1-14 nM, and EGF & TGFα 2-3 nM.

In addition, cell lines from disease models may be used to estimate the expression level of target cells in a human patient, for example. For example, for ligand-drug particles with one or more ligands specific for the epidermal growth factor receptor (EGFR), one can obtain cancer cell lines such as MDA-MB-468, MB-MB-231, and MCF-7 with published $1\text{-}1.3*10^6$ EGFR/cell, $1\text{-}1.3*10^5$ EGFR/cell, and $1\text{-}1.5*10^4$ EGFR/cell respectively. For ligand-drug particles specific for human epidermal growth factor receptor (HER2), for example, one can obtain HER2-overexpressing cancer cell lines such as BT474 ($10^6$ HER2/cell), SK-BR-3 ($3*10^6$ HER2/cell), etc. Similarly, one can obtain well characterized cell lines that overexpress other potential receptor proteins. Alternatively, one can transfect cell lines to express those antigen/receptors if necessary such as HER2-overexpressing MCF-7/HER2 and VEGFR2-overexpressing PAE/KDR ($2.5*10^5$ VEGFR2/cell) and 293/KDR ($2.5*10^6$ VEGFR2/cell).

It is understood that the valencies given herein are average valencies for the particle and that due to manufacturing methods, actual individual particle valencies may vary somewhat from one particle to the next. Valency (number of ligands per particle) may be measured experimentally, for example, from the ratio of protein to phospholipid (see references 35, 36, 38, 42, 44 below). For example, phospholipid concentration of a ligand-drug particle can be measured by a phosphate assay (ref. 118) or high performance liquid chromatography (HPLC). Ligand concentration of a ligand-drug particle can be determined by ImageJ® (National Institutes of Health) from SDS-PAGE stained with SYPRO® Ruby. Other protein quantification methods are possible such as BCA Protein Assay Kit (Thermo Scientific), Quant-iT® Protein Assay Kit (Life Technologies), SDS-PAGE (Bio-Rad), UV spectormerty, and HPLC. All measurments are against a phosphate or protein standard. For example, for a liposome size of 100 nm in diameter and an average area per phospholipid molecule of 75 Å$^2$, this gives an average of 80,000 phospholipid molecules per liposome. Antibodies have an average molecular weight of 150-160 kDa, Fab' of ~50 kDa, and scFv of ~25 kDa. Protein concentration to phospholipid concentration provides the protein to phospholipid ratio, which with the phospholipid per particle and protein per ligand correction factors, determine the valency. Other techniques are also possible such as dual measurements of protein and lipid through HPLC, labeling the ligands and/or lipids with a fluorescent marker for quantification, or secondary component measurements such as quantification of encapsulated drug or embedded cholesterol or PEG.

Systems and Methods for Optimizing Ligand Valence

This disclosure also contemplates systems for determining ligand valency for a ligand-drug particle, wherein the particle comprises a lipid surface layer, at least one drug in the interior of the particle or embedded in the lipid surface layer, and a ligand specific for a receptor on a target cell, the ligand exposed on the lipid surface layer, the system comprising software capable of determining ligand valency from in vitro ligand-receptor dissociation constant and average number of receptors per target cell according to a crosslink multivalent binding model. The disclosure also contemplates systems for determining ligand valency for a ligand-drug particle, wherein the particle comprises a lipid surface layer, at least one drug in the interior of the particle or embedded in the lipid surface layer, and two ligands each specific for a receptor on a target cell, the ligands exposed on the lipid surface layer, the system comprising software capable of determining ligand valency from in vitro ligand-receptor dissociation constants for each ligand-receptor pair and average number of each receptor per target cell and either additive or synergistic binding according to a cross-link multivalent binding model. In such systems, software may be used, for example, to determine an optimal valency based on methods described in Example 1 below.

For example, in some embodiments, one may determine ligand valence by obtaining or determining a ligand-receptor $K_D$ and a receptor expression level (e.g., number of receptors per target cell; $R_T$) and then determining a plot or relationship of the number of cell-associated particles per cell at equilibrium ($C_{Beq}$) to valence, where the peak of the plot curve comprises the maximum cellular uptake and an optimal valence. (See for example FIGS. 14-15.) Briefly, with known or determined $K_D$, $R_T$, and assumed equilibrium and steady-state constants, one would apply the crosslink binding model (equations 5-3b and 5-3d) to solve simultaneously for a function of $C_{Beq}$ to valence. The examples below were conducted in Mathcad®, solving a system of differential equations for a plot of $C_{Beq}$ to valence. The maximum calculated cell association ($C_{Beq}$) and its respective valence (rounded to an integer) provide an optimum valence for ligand-drug particle uptake. A working range of $K_D$ and $R_T$ were examined and disclosed as examples. For dual-targeted ligand-drug particles, additive binding can be calculated based upon the sum of the $C_{Beq}$ of each individual particle cell association calculated separately. For dual-targeted ligand-drug particles, synergetic binding can be calculated based upon a singular dissociation constant and crosslinking equilibrium constant for the ligand-receptor binding combination with higher affinity. As examples, valences ratios of 1:1 for each ligand duals were accessed; other combinations can also be examined. A working range of $K_D$ and $R_T$ were examined and disclosed as examples. Through the cell association plots, these calculations also display the cellular uptake levels of ligand-drug particles. Other mathematical software are possible to assist in the calculations such as Mathcad®, Matlab®, Maple®, Mathematica®, Python®, R, etc.

In the equations 5-3b and 5-3d, $R_{eq}$ is the number of free receptors per cell at equilibrium, $C_{Beq}$ is the number of cell-associated particles per cell at equilibrium, $R_T$ is the total number of receptors per cell, Lo, which is the free particle concentration in solution, $K_D$ is the equilibrium dissociation constant of the ligand for its receptor on the cell, v=valence, f is the effective valence, which is essentially the effective number of ligands per particle that can bind to a cell out of the total valence (v), and $K_X = k_x/k_{-x}$ is the crosslinking equilibrium constant. $C_i$ is the concentration of a particle bound to the cell surface via i of its v available surface-attached ligands (i=0, 1, 2, . . . , f).

EXAMPLES

Example 1. Mathematical Insights on the Binding and Trafficking of Ligand-Drug Particles To better capture the dynamics between ligands and receptors on cells, many models for the cell surface receptor binding and trafficking of both ligands and receptors have been proposed (133-140). Translating the kinetic models of ligands with receptors to multivalent nanoparticles with receptors may provide insight to the experimental data and as well as observations in the literature. To begin, one may start with a base case of the monovalent binding of ligand ($L_g$) to receptor (R) to form a ligand/receptor complex ($C_{Lg}$) (FIG. 1). Through mass action kinetics, the kinetics of ligand, receptor, and complex with time can be described as equation 5-1 with association and dissociation rate constants $k_f$ and $k_r$, respectively. Unlike many ligands, nanoparticles such as ligand-drug particles are multivalent. Nanoparticles are nanometers in size, for example 10-500 nm in length or diameter. The first bond of a single ligand on a nanoparticle to a single receptor on the cell surface can still be applied with the base model, but subsequent interactions should be considered and adjusted to more accurately model the avidity.

$$\frac{dC_{Lg}}{dt} = k_f \cdot L_g \cdot R - k_r \cdot C_{Lg} \tag{5-1}$$

In regards to the receptor, the receptor can interact with other receptors and proteins, forming ternary complexes. The ErbB family of receptor tyrosine kinases such as EGFR and HER2 are known to form dimers, for example. The affinity of ligands to single receptors compared to dimers, whether with one or more binding sites occupied, can greatly change the binding and internalizing kinetics, with the later, dimerization with higher binding site occupancy usually associated with higher affinity(133, 138, 141). For immunoglobulin receptors, the separation distance between the sites of a bivalent antibody is between 9 and 20 nm(135, 142, 143). For a liposome particle with 20 surface ligands and an average diameter of 100 nm, the separation between ligands is approximately 40 nm assuming equal distribution. This distance can be slightly greater through a polymer linker attached to the ligand. Due to the spacing of the targeting groups on a nanoparticle such as a ligand-drug liposome particle, it is unlikely for a single nanoparticle to occupy both sites of a bivalent receptor or even occupy both dimerized receptors. Hence, it is assumed that nanoparticles with functional monovalent ligands can only occupy one site per single receptor or set of dimerized receptors. This simplifies the model, treating the receptors as monovalent. Keep in mind that higher valence nanoparticles, smaller multivalent nanoparticles, and ligand-drugs are in the realms of possibility of bivalent receptor binding. Other ternary complex possibilities that receptors can interact with are G-proteins, coated-pit binding proteins, and cytoskeletal elements(133). It is assumed that none of these are rate-limiting or saturated in the model.

Relative to a ligand, nanoparticles are large, increasing interaction with multiple components on a cell such as additional receptors, proteins, lipids, and macromolecules that may induce binding. Non-specific binding can skew a binding model. Immunoliposomes are coated with a layer of polyethylene glycol, providing sterical stabilization that limits the non-specific binding and interaction with cells. Therefore, it is assumed that non-specific binding is minimal, as also evident by low cell association for non-targeted liposomes. The experimental studies mainly focused on targeting cancer cells that overexpressed receptors, specifically EGFR and HER2, and likewise, these may be used as targets of the model. Assuming an average cell diameter of 10 μm with $10^6$ receptors and an average liposome particle diameter of 100 nm with 20 ligands, the receptor to ligand per surface area ratio is 5, meaning that for every ligand there are 5 receptors available to bind. Crosslink multivalent binding of liposomes to multiple receptors is a possible and plausible outcome.

Figure 2A:
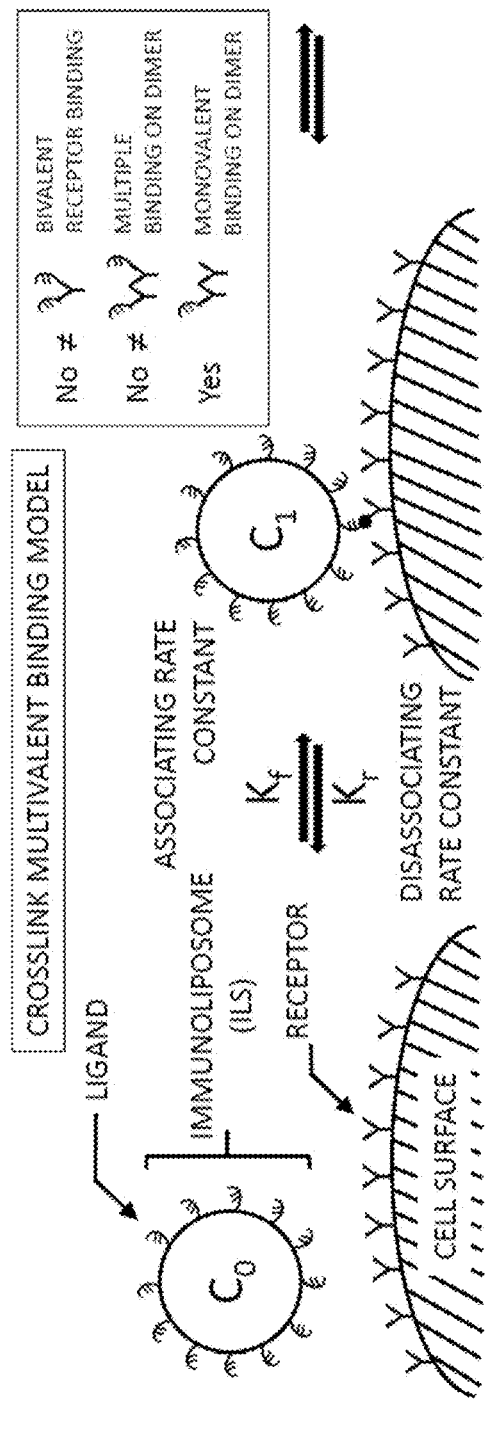
FIGS. 2A and 2B show a schematic of the crosslink multivalent binding model of multivalent nanoparticles to monovalent receptors. Let $C_i$ be the concentration of a nanoparticle bound to the cell surface via i of its v (valence) available surface-attached ligands (i=0, 1, 2, . . . , f) where f is the effective valence.
Figure 2B:
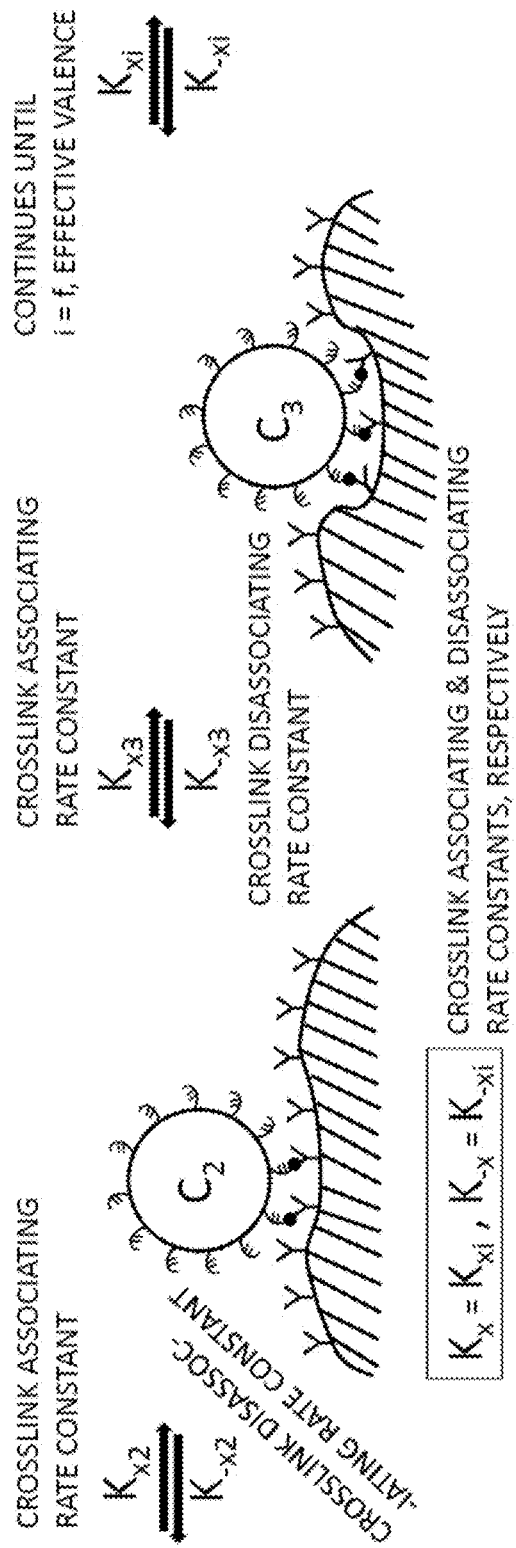

The crosslink multivalent binding model for multivalent ligands to monovalent receptors, developed and reviewed by a number of investigators(134-136, 139, 140), was applied to model the cell association of nanoparticles (FIG. 2A-2B). The general idea is that a free nanoparticle ($L=C_0$) first binds to a single receptor (R) as described by the base monovalent binding model. Subsequently, a second ligand on the nanoparticle binds to a second receptor with forward and reverse crosslinking constants ($k_x$ and $k_{-x}$), resulting in a complex consisting of a nanoparticle bound to the surface by 2 ligands. Additional ligands simultaneously bind to the cell surface until the number of ligand-receptor bounds reach the effective valence (f), essentially the effective number of ligands per nanoparticle that can bind to a cell out of the total valence (v). Consequently, the multivalent nanoparticle with f crosslinked receptors is internalized into the cell by receptor-mediated endocytosis. It is assumed that f≤v due to sterical hindrance with the bound receptor and suboptimal positioning and spacing of the ligands(135). Let $C_i$ be the concentration of a nanoparticle bound to the cell surface via i of its v available surface-attached ligands (i=0, 1, 2, . . . , f), equations by mass action kinetics to describe the crosslink multivalent binding model building upon the monovalent binding model are as follows:

$$L + R \rightleftarrows C_1 + R \rightleftarrows C_2 + R \ldots \rightleftarrows C_i + R \rightleftarrows \ldots C_f \tag{5-2a}$$

$$\frac{dL}{dt} = -v \cdot k_f \cdot L \cdot R + k_r \cdot C_1 \tag{5-2b}$$

$$\frac{dC_1}{dt} = v \cdot k_f \cdot L \cdot R - k_r \cdot C_1 - (f-1) \cdot k_x \cdot C_1 \cdot R + 2 \cdot k_{-x} \cdot C_2 \tag{5-2c}$$

$$\frac{dC_i}{dt} = (f-i+1) \cdot k_x \cdot C_{i-1} \cdot R - \\ i \cdot k_{-x} \cdot C_i - (f-i) \cdot k_x \cdot C_i \cdot R + (i+1) \cdot k_{-x} \cdot C_{i-1} \\ i = 2, 3, \ldots, f-1 \tag{5-2d}$$

$$\frac{dC_f}{dt} = k_x \cdot C_{f-1} \cdot R - f \cdot k_{-x} \cdot C_f \tag{5-2e}$$

At steady-state, solutions for the number of free receptors per cell at equilibrium ($R_{eq}$) and the number of cell associated nanoparticles per cell at equilibrium ($C_{Beq}$) can be symbolic solved with the additional parameters (total receptors per cell ($R_T$), free nanoparticle concentration in solution ($L=L_o$), equilibrium dissociation constant ($K_D=k_r/k_f$), and the crosslinking equilibrium constant ($K_X=k_x/k_{-x}$)):

$$R_T = R + \sum_{i=1}^{f} i \cdot C_j \tag{5-3a}$$

$$R_T = R_{eq} \cdot \left[1 + v \cdot \left(\frac{L_O}{K_D}\right) \cdot (1 + K_X \cdot R_{eq})^{f-1}\right] \tag{5-3b}$$

$$C_{ieq} = \left[\frac{f!}{i! \cdot (f-i)!}\right] \cdot K_X^{i-1} \cdot \frac{v}{f} \cdot \left(\frac{L_O}{K_D}\right) \cdot R_{eq}^i \tag{5-3c}$$

$$C_{Beq} = \sum_{i=1}^{f} C_{ieq} = \frac{v}{K_X \cdot f} \cdot \left(\frac{L_O}{K_D}\right) \cdot [(1 + K_X \cdot R_{eq})^f - 1] \tag{5-3d}$$

High Receptor Expression Model

All parameters in the model are based on experimental data and from the literature, particularly for studies pertaining to anti-HER2 F5 scFv-conjugated immunoliposomes and BT-474 cells in the high receptor expression model. For analysis at equilibrium (time<4 hr), assume a constant free nanoparticle concentration in solution ($L=L_o$), no nanoparticle and receptor depletion effects, and constant forward and reverse crosslinking constants ($k_x$ and $k_{-x}$) for additional receptor binding. The total receptors per cell ($R_T$) is $10^6$ for high receptor expressing cells (ie, BT-474 cells; adjusted to $10^5$ and $10^4$ for the moderate and low receptor expression models, respectively). The free nanoparticle concentration in solution ($L_o$) is $10^6$ nanoparticles per cell (~70-100 µM PL), which is approximately the saturating concentration observed at the optimal cell association. The equilibrium dissociation constant ($K_D=k_r/k_f$) is 100 nM (111 nM for monovalent F5 scFv-ILS, 160 nM for F5 scFv)(34). The crosslinking equilibrium constant ($K_X=k_x/k_{-x}$) is 1/(70K #/cell) for high receptor expressing cells, estimated from the maximum uptake of nanoparticles in dose-uptake studies assuming high crosslinking. For the moderate and low receptor expression models, $K_X$ of 1/(10K #/cell) and 1/(3K #/cell) were estimated, respectively. Valence and effective valence in the range of 1-200 ligands per nanoparticle were evaluated since that is the maximum Fab' valence per nanoparticle stably construct in experiments. Since $f \le v$, assume that if $v<f$, then $f=v$ (equation 5-4). The number of free receptors per cell at equilibrium ($R_{eq}$) and the number of cell associated nanoparticles per cell at equilibrium ($C_{Beq}$) as a function of v and f were evaluated and plotted using Mathcad®.

$$f = \begin{vmatrix} v & \text{if } v < f \\ f & \text{otherwise} \end{vmatrix} \quad (5\text{-}4)$$

Figure 3:
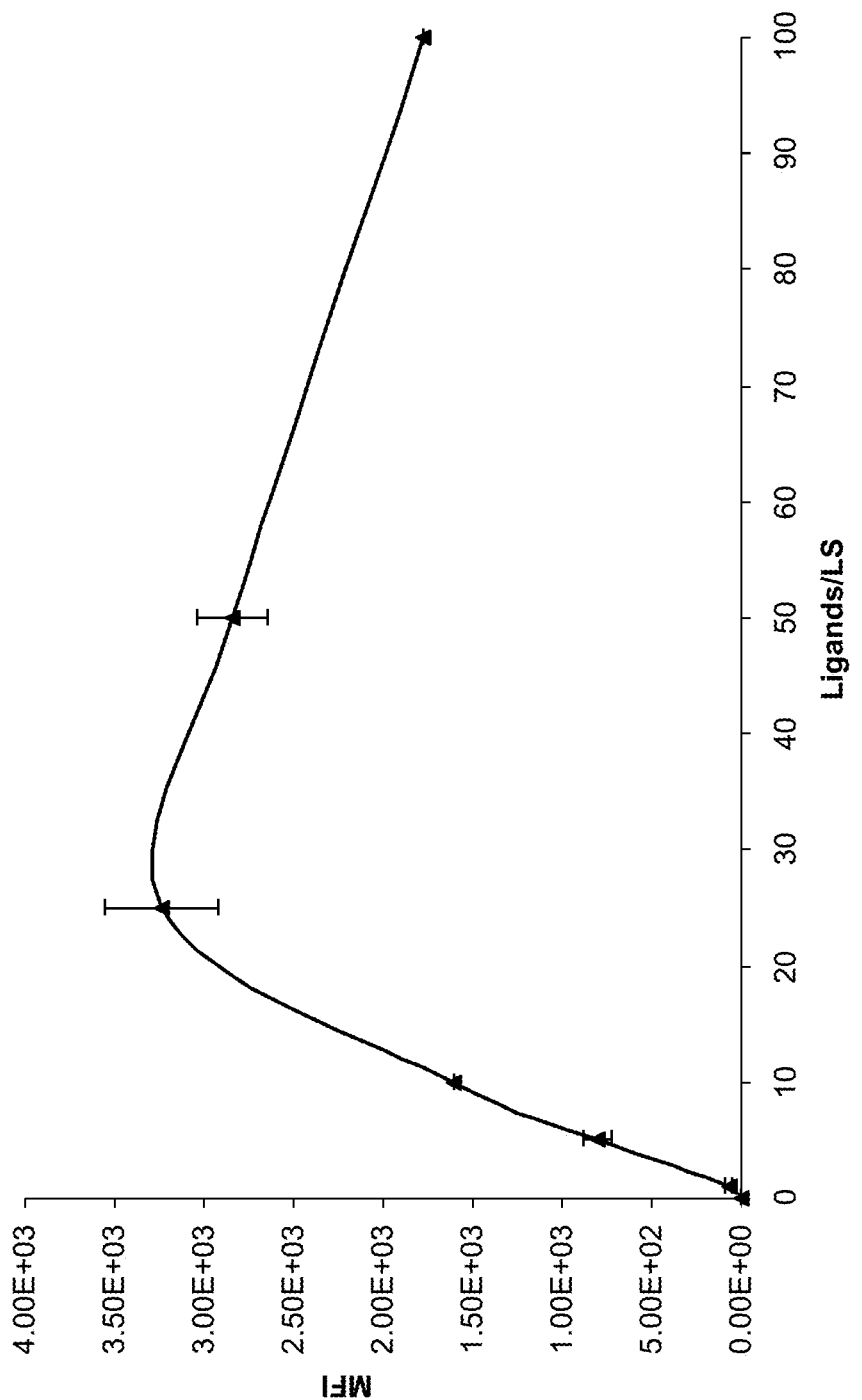
FIG. 3 provides a cell association of F5 scFv-conjugated immunoliposomes (ILS) with increasing valence in MCF-7/HER2 cells. Cells were incubated with liposomes (LS) labeled with DiD (75 uM PL) at 37° C. for 1 hr and analyzed by flow cytometry (mean fluorescence intensity [MFI] with a tight spread of $5*10^3$ cells).
Figure 4A:
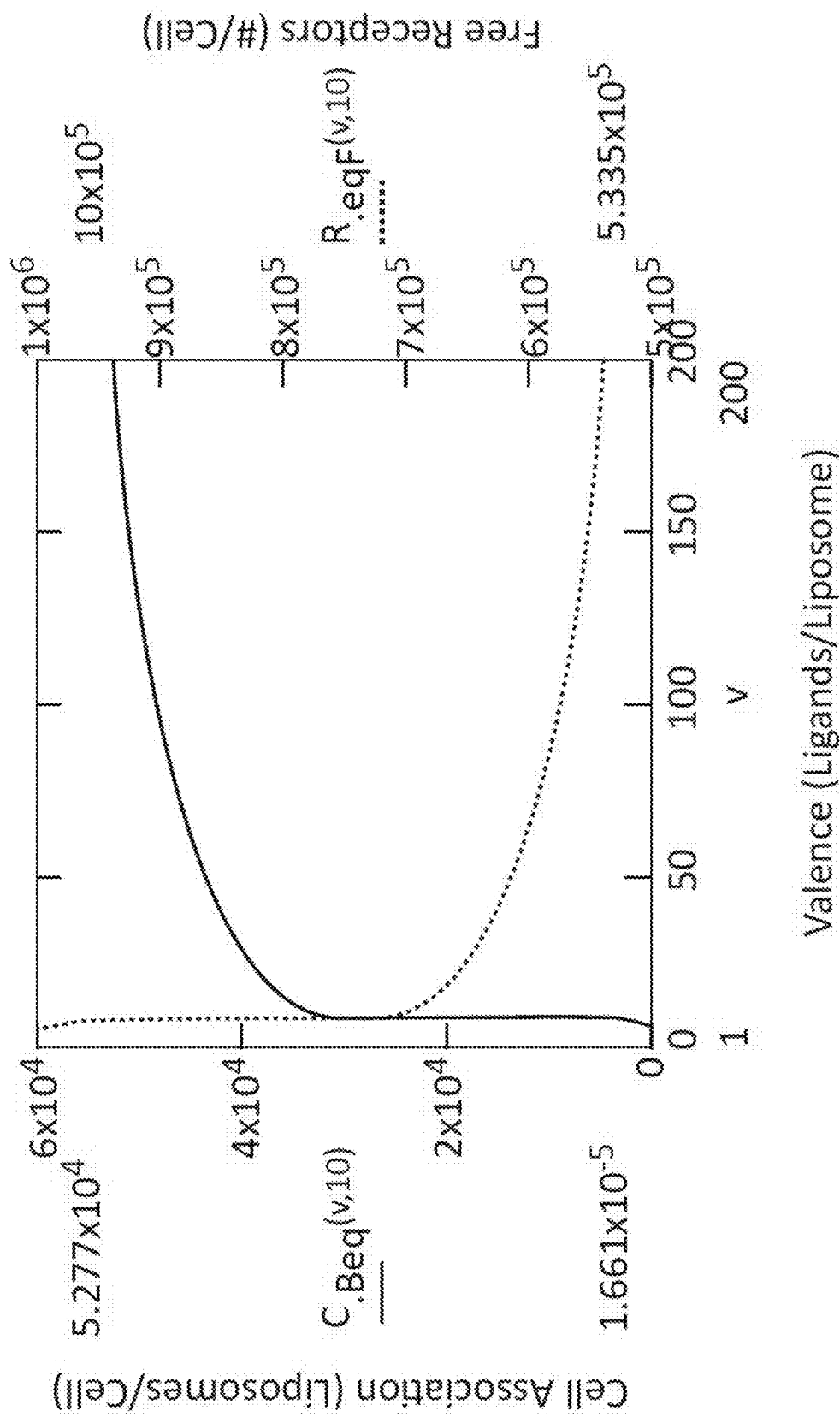
FIGS. 4A, 4B and 4C provide crosslink multivalent binding model predictions in high receptor expressing cells. Plots of nanoparticle cell association ($C_{Beq}$) and/or free receptors ($R_{eq}$) as a function of valence (v) in high receptor expressing cells ($R_T=10^6$ #/cell) with an effective valence (f) of FIG. 4A. f=10 ligands per nanoparticle, FIG. 4B. f=7, 10, 17, 50, & 100, and FIG. 4C. f=v. Values were evaluated in Mathcad® with the additional parameters: $10^6$ nanoparticles per cell in solution ($L_o$), 100 nM equilibrium constant ($K_D$), $1/(70*10^3$ #/cells) crosslinking equilibrium constant (Kx). It is assumed that there are no nanoparticle and receptor depletion effects, and since f≤v, if v<f then v=f.
Figure 4B:
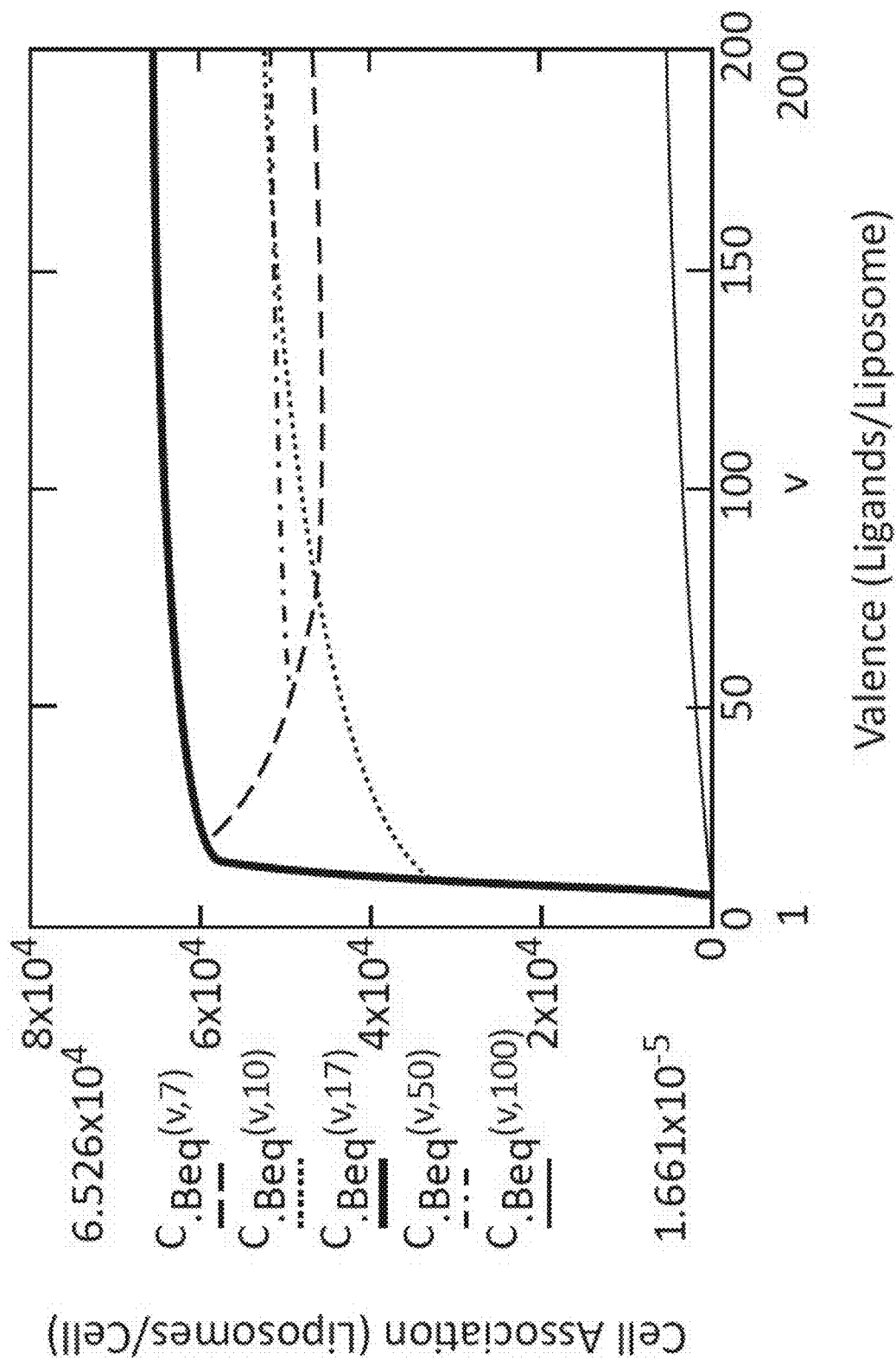
Figure 4C:
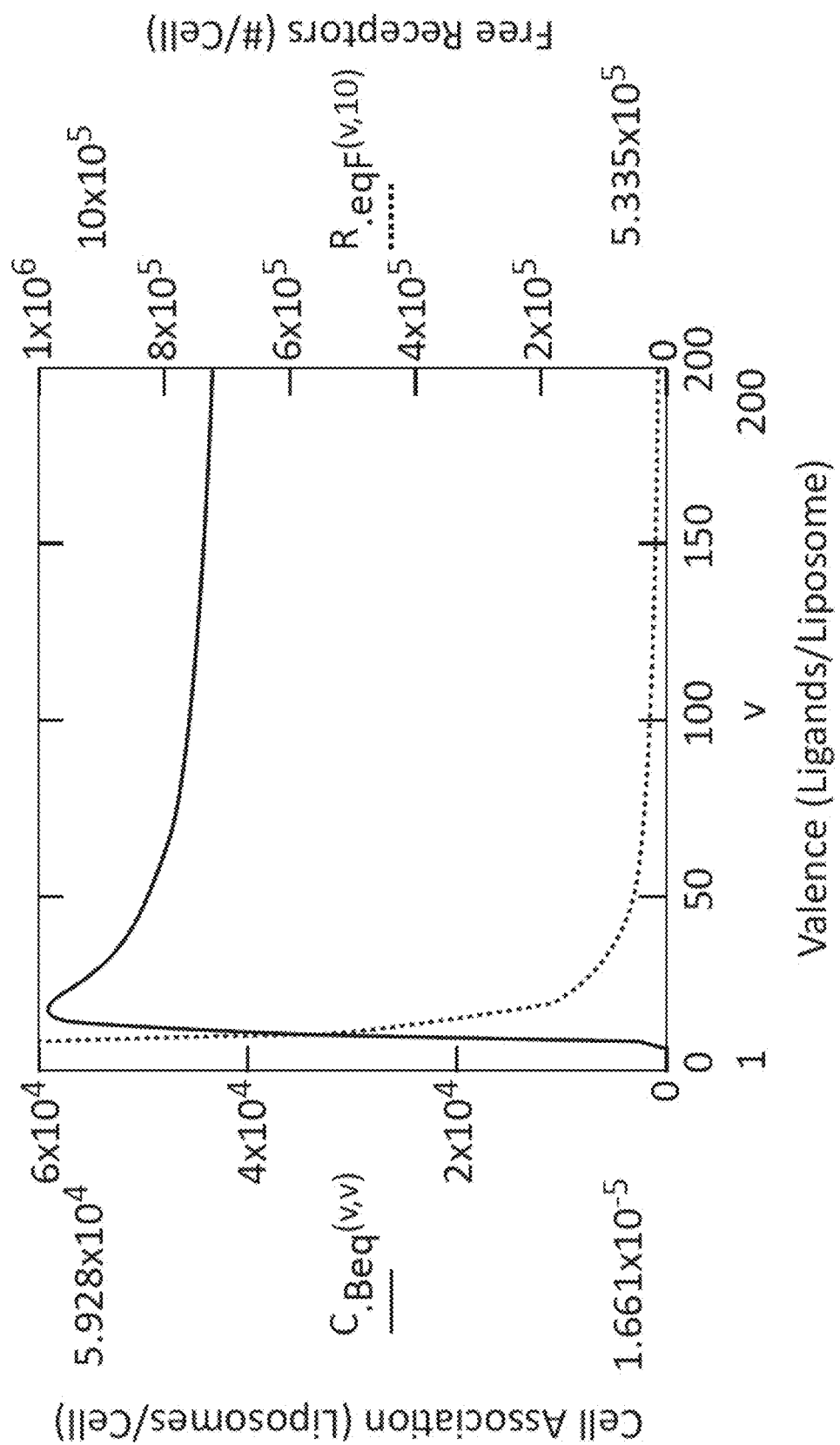

Predictions calculated from the crosslink multivalent binding model on the cell association of multivalent nanoparticles to cells overall quite accurately describe experimental data. For example, optimal cell association of liposome particles to cells, depending on ligand, has been observed at v=15-40 antibody fragments per liposome(4, 33-37), as demonstrated with EGF-LS and TGFα-LS and F5 scFv-ILS in FIG. 3. Since binding and uptake saturate in that range, an effective valence of $f=10<v$ was initially predicted (FIGS. 4A-C). Increasing the surface valency of ligands per nanoparticle with $f=10$ correlated to increased targeted association in the high receptor expression model until a plateau. Complementarily, the concentration of free receptors decreased as the concentration of nanoparticles was receptor-associated. These results fit quite in line with the observations.

Figure 6A:
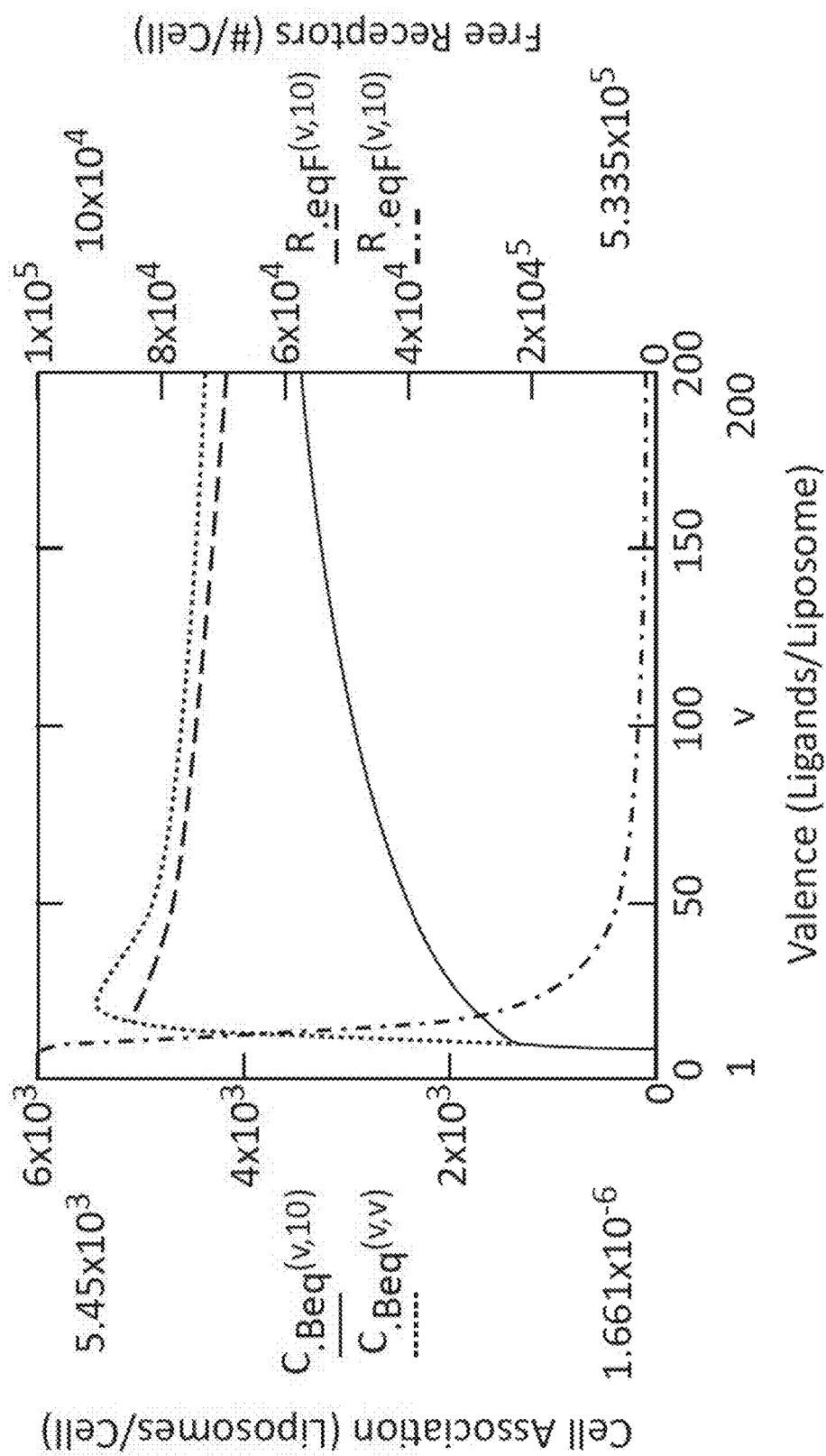
FIGS. 6A and 6B provide crosslink multivalent binding model predictions in moderate (FIG. 6A) and low (FIG. 6B) receptor expressing cells. Plots of nanoparticle cell association ($C_{Beq}$) and free receptors ($R_{eq}$) as a function of valence (v) in moderate receptor expressing cells ($10^5$ #/cell) (FIG. 6A) and low receptor expressing cells ($10^4$ #/cell) (FIG. 6B) with an effective valence (f) of 10 or v ligands per nanoparticle. Values were evaluated in Mathcad® with the additional parameters: $10^6$ nanoparticles per cell in solution ($L_o$), 100 nM equilibrium constant ($K_D$), $1/(10*10^3$ #/cells) and $1/(3*10^3$ #/cells) crosslinking equilibrium constant ($K_X$) for moderate and low receptors model, respectively. It is assumed that there are no nanoparticle and receptor depletion effects, and since f≤v, if v<f then v=f.
Figure 6B:
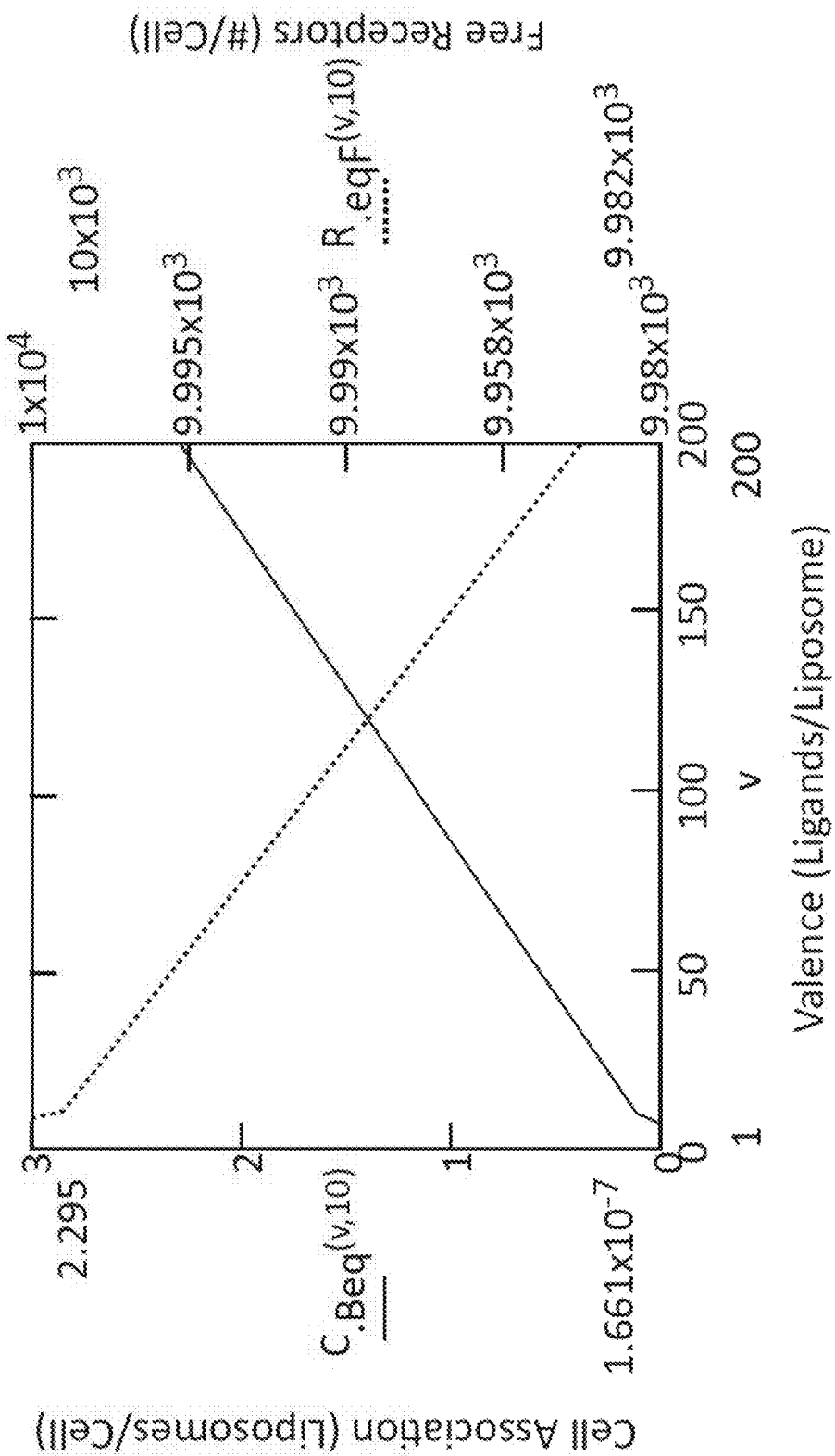

Various effective valences were also analyzed (FIGS. 4A-4C). At $f \le 7$ (ie, $f=7$), the binding is reasonably linear, increasing, and negligible in comparison to higher effective valences. This is similar to monovalent ligand binding and low receptor expressing models discussed later (FIG. 6A-6B). At $f=8-17$ (ie, $f=10$), the overall bound concentration increases significantly, curves to saturation, and then maxes at $f=17$. For f higher than 17 (ie, $f=50$ or 100), cell association subsequently decreases. A peak at $f=17$ supports that v=15-40 observed. When $v>f=17$, the overall binding starts to decrease.

Figure 5A:
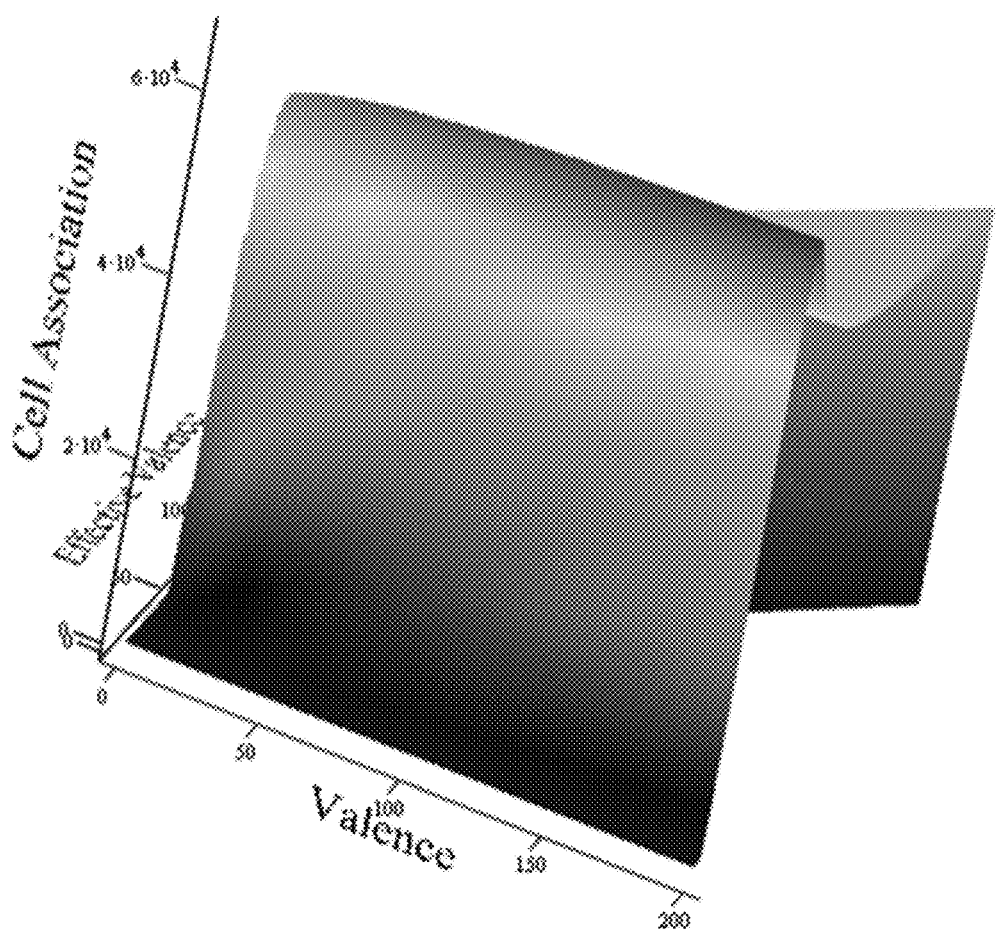
FIGS. 5A and 5B provide crosslink multivalent binding model predictions for all plausible valence and effective valence (f≤v) in high receptor expressing cells.
Figure 5B:
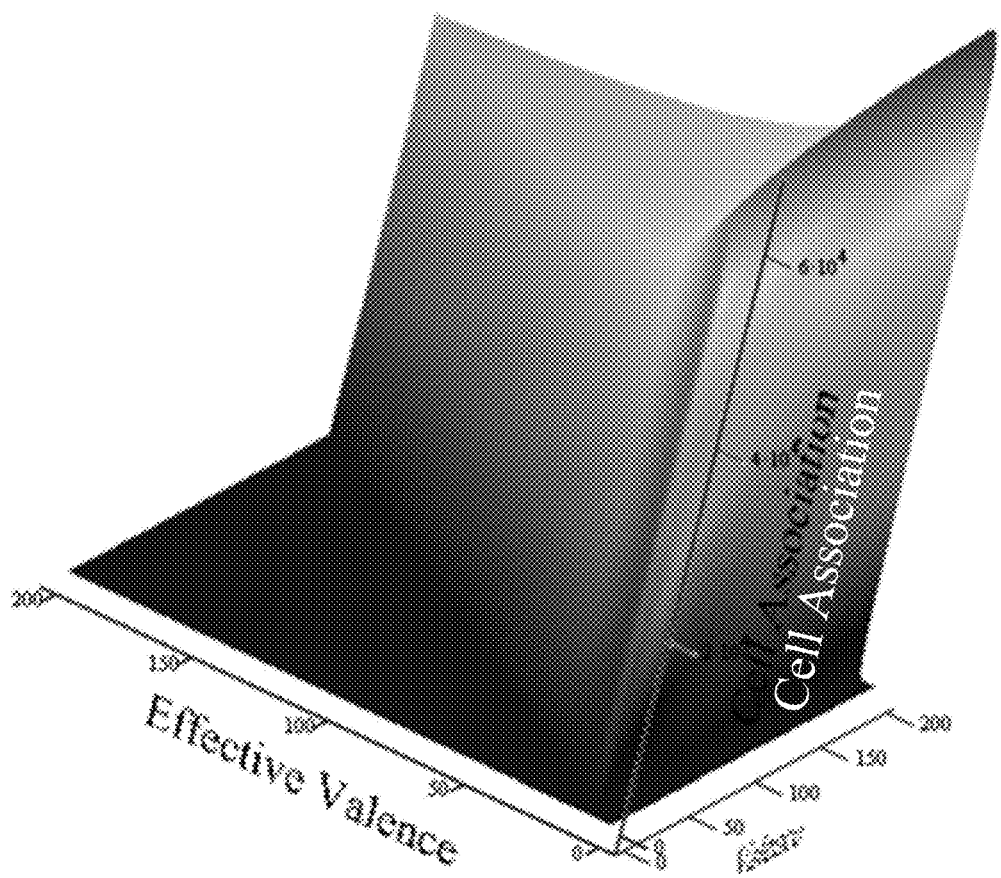

The effective valence was initially assumed to be constant and much lower than v as observed for models of multivalent ligands. What if f is not constant, but increases as v increases? As previously mentioned, at v=20, there are 5 receptors available in a given surface area per ligand, reducing to a reasonable 1:1 at v=100. Hence, it is plausible that nanoparticles can have a high f/v ratio. A scenario where $f=v$ and that assumes that every ligand on the nanoparticle efficiently binds to a receptor is plotted in FIGS. 4A-4C. The graph displays a familiar observation seen with experimental data, where increasing the valence beyond the optimal valence can decrease cell association (FIG. 5A-5B). This will hold true not only for a model where $f=v$, but when $v>f=17$ (ie, $f=50$ & 100, FIG. 4A-4C) or when f increases with v. In addition, at a high effective valence like when $f \approx v$, it supports the data where roughly a 1:1 ratio of ligands to expressed receptors was observed internalized at optimal valence. Plots of the cell association as a function of the full f and v range ($f \le v$) were also analyzed in the model (FIG. 5A-5B), indicating that the optimal cell association can be no further optimized based purely on ligand surface valency.

Moderate and Low Receptor Expression Models

Moderate and low receptor expression models were also considered (FIG. 6A-6B). The total receptors per cell availability was reduced, and likewise $K_X$ lowered and adjusted to match the empirical data. It is expected that f will be much lower than cases for the high expression model and hence mainly examined $f=10$. For the moderate receptor expression model, when $f=10$, binding was observed to increase with v reaching a steady plateau as free receptors concentration decreased. These results support the cell association of a HER2/EGFR moderately expressing cell line MKN-7. The scenario where $f=v$ was also considered, but may not be realistic due to the lower receptor availability. In reality, f will most likely have a lower limit than for cases of the high receptor expression model. In the case of the low receptor expression model, the cell association behavior appropriately resembles monovalent ligand binding, showing a linear non-crosslinking, non-cooperative binding with very low binding, similar to $f=1$ for the high receptor expression model.

Data Fitting, Limitations, and Optimization

Concentrations of the calculated cell association closely approximate the dose-uptake experimental data at comparable liposomal incubation concentrations (L at 89 µM). For HER2 high-expressing BT-474 cells ($RT=10^6$ receptors per cell), the model calculated the bound liposomes per cell concentration of $5.9*10^4$ for v=15, where in the dose-uptake studies I observed cellular uptake at $6.8*10^4 \pm 7*10^3$ for v=15. The estimated uptake is within 85% accuracy of empirical data. When the high receptor expression model was adjusted for SK-BR-3 cells (increasing to $3*10^6$ receptors per cell), the calculated concentration again appropriately increased. For SK-BR-3 cells, the model calculated bound liposomes per cell concentrations of $2.3*10^5$ for v=10 and $2.2*10^5$ for v=15, where in the dose-uptake studies I observed cellular uptakes at $2.3*10^5 \pm 4*10^3$ for v=10 and $2.3*10^5 \pm 9*10^3$ for v=15. The estimated values are within 95% accuracy of empirical data. Since v for optimum binding was calculated to be v=11 for SK-BR-3 cells, it is appropriate that the observed uptake in the dose-uptake studies was slightly higher for v=10 than for v=15, as predicted from the model. Suitably, it also suggests that the optimum v decreases as the number of available receptor increases as expected. When $R_T$ was lowered to $5*10^5$ receptors per cell, the optimum ligand valence was observed at ~30 ligands per liposome, which would account for the full 15-40 ligands per liposome range observed for optimal uptake.

Assuming the equilibrium dissociation constants for monovalent nanoparticles and their respective attached ligand are comparable as in the real example of F5 scFv, the crosslink multivalent binding model allows researchers to estimate the optimum valence and cell association by knowing the dissociation constants of the ligand and the receptor expression level of a cell. However, based on the crosslink multivalent binding model for the cell association of multivalent nanoparticles to high receptor expressing cells, the current systems may have already been optimized purely from experimental data. Varying monovalent ligand valency beyond the 10+v range will not significantly alter the binding and uptake of nanoparticles.

Figure 7:
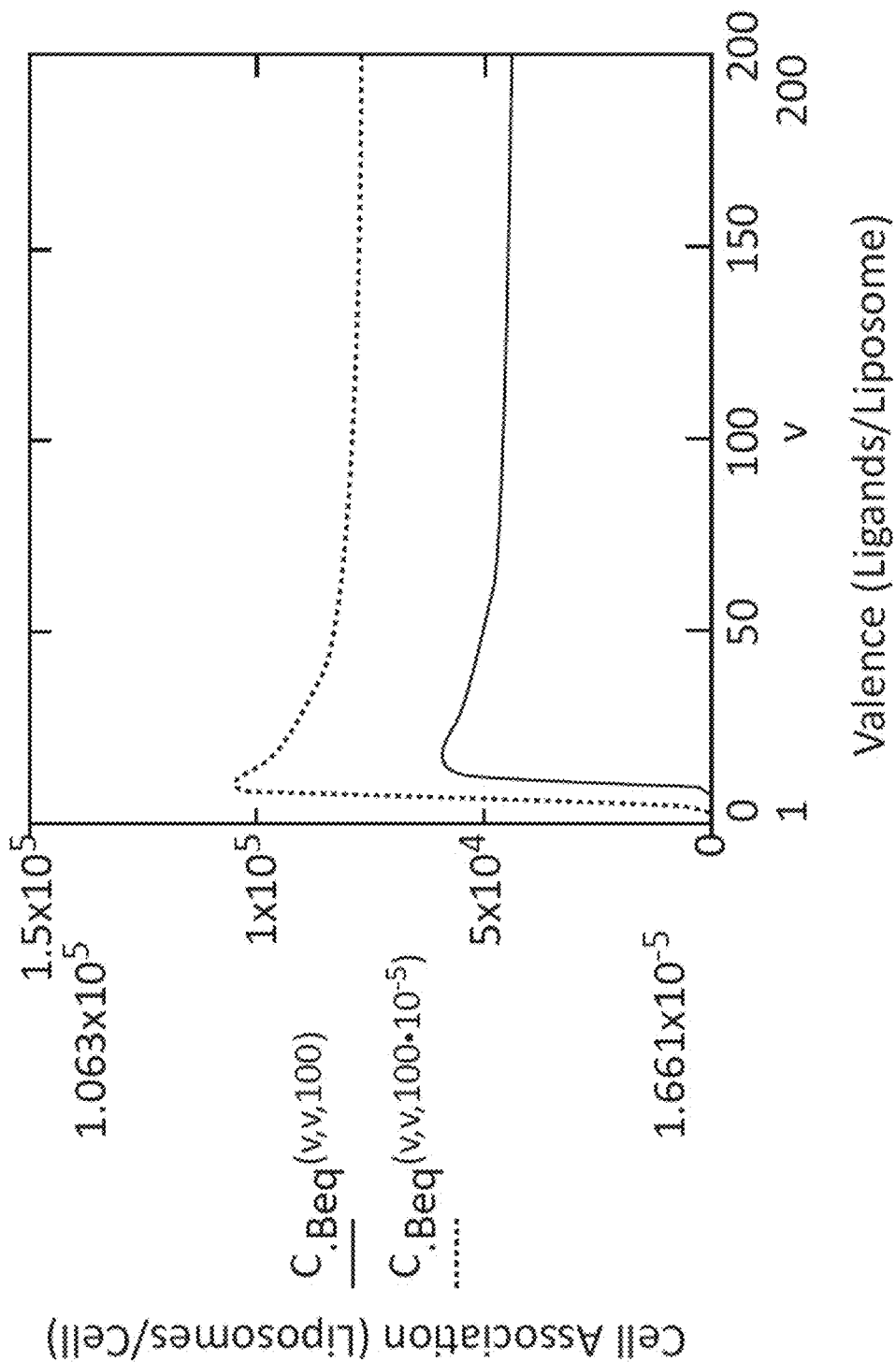
FIG. 7 provides a crosslink multivalent binding model prediction for increased affinity. The equilibrium dissociation constant was decreased from 100 nM to $100*10^{-5}$ nM in the high reception expression model with f=v, resulting in approximately only 2-fold increase in cell association.
Figure 8:
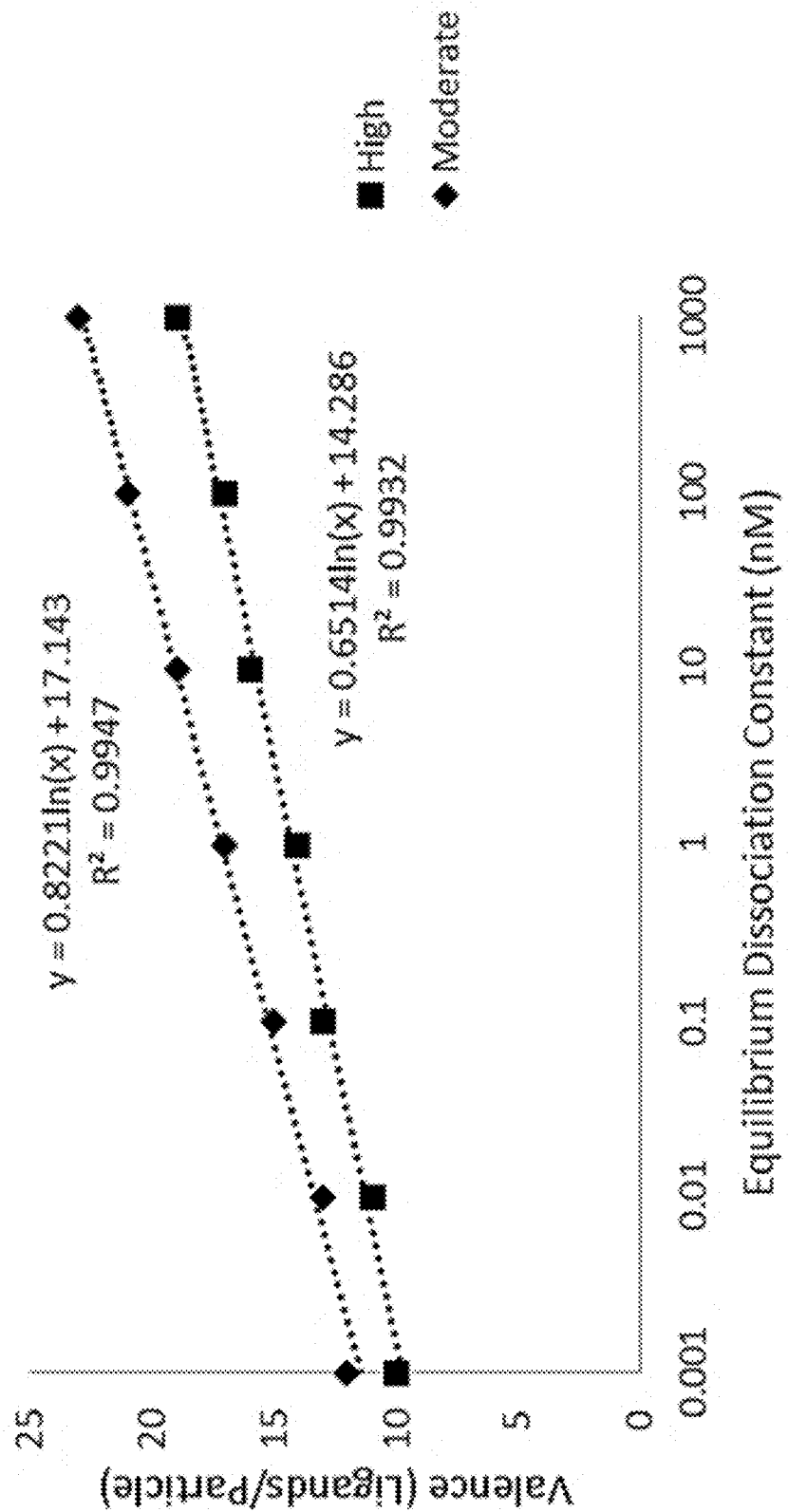
FIG. 8 provides a plot of optimal calculated valence for a single ligand (#ligands/particle) against equilibrium dissociation constant for ligand-receptor binding under both high receptor expression (on the order of $10^6$) or moderate receptor expression (on the order of $10^5$) models. Additional data based on this curve may be found in Table 1 below.
Figure 9A:
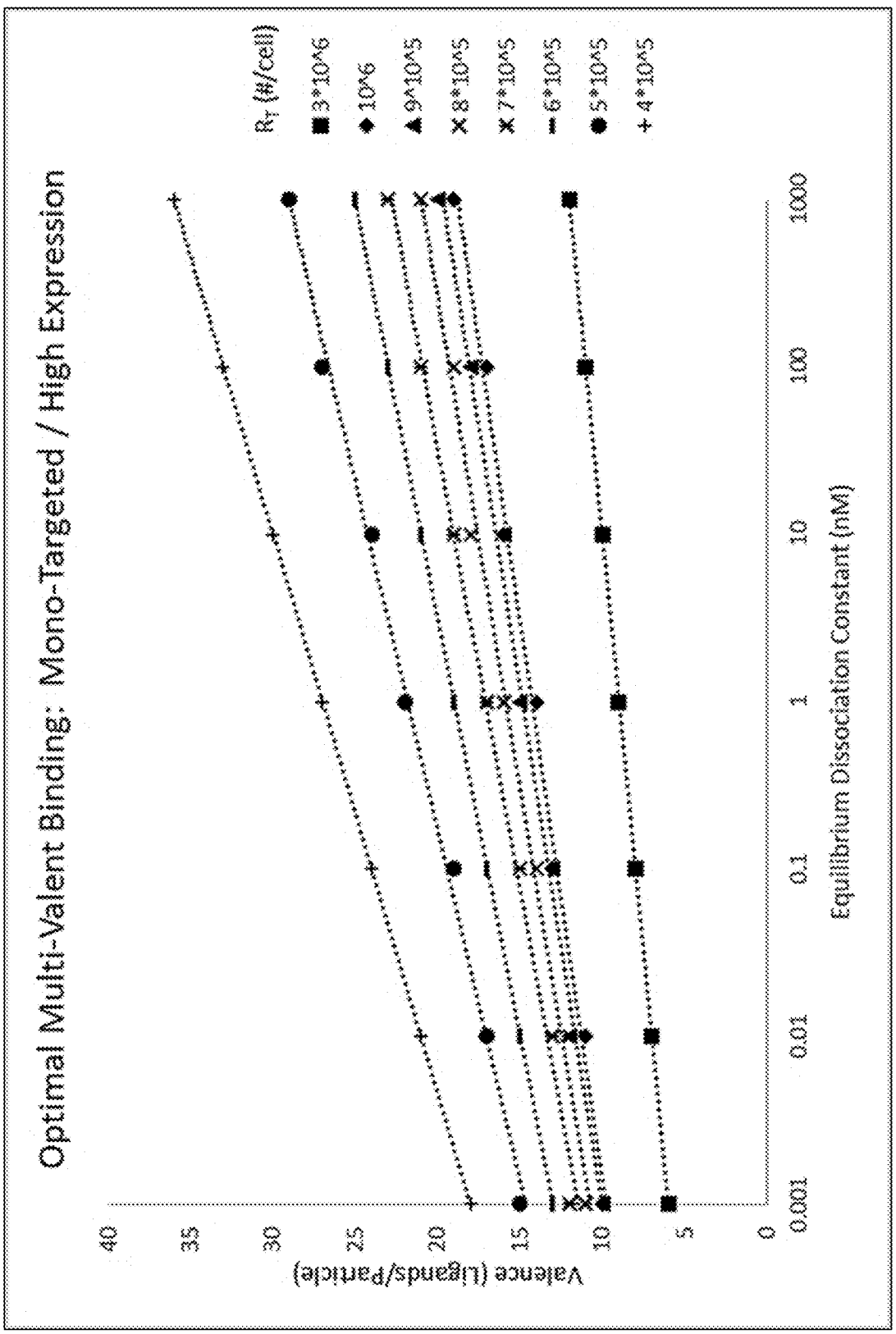
FIG. 9A provides a plot of optimal calculated valence for a single ligand (#ligands/particle) against equilibrium dissociation constant for ligand-receptor binding under several different receptor expression levels.
Figure 9B:
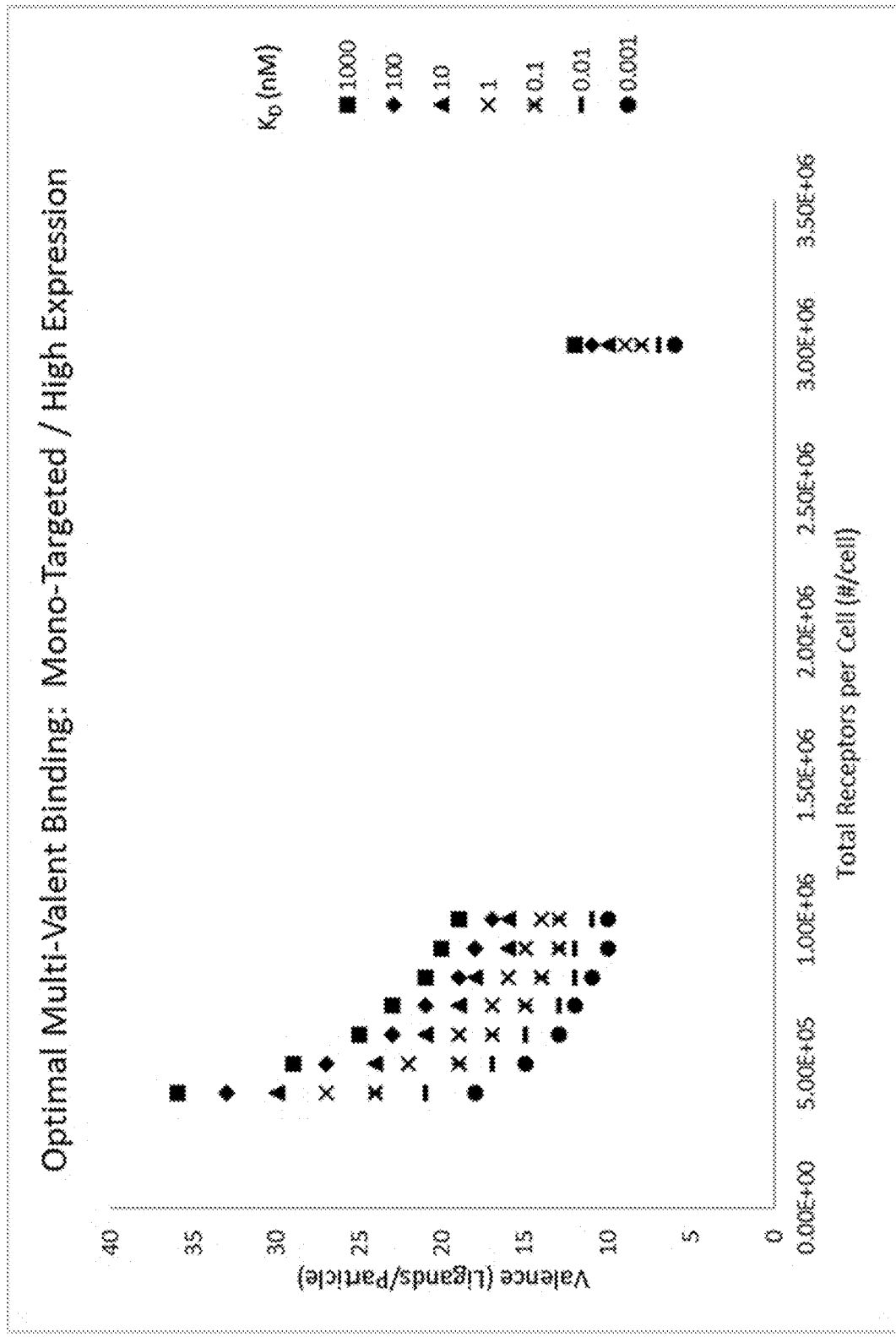
FIG. 9B provides the relationship of optimal valence against receptor expression level (#receptors/cell) at different ligand-receptor equilibrium dissociation constants. Additional data based on FIGS. 9A and 9B may be found in Table 2 below.
Figure 10C:
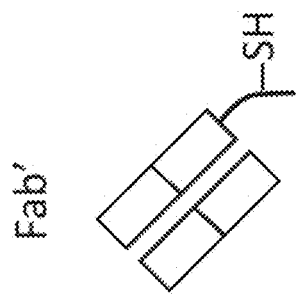
FIGS. 10A, 10B, 10C and 10D show a schematic of steps in a synthesis of a Fab'-PEG-DSPE linkage, for example, as means of attaching a Fab' ligand to a lipid surface layer of a ligand-drug particle.
Figure 10B:
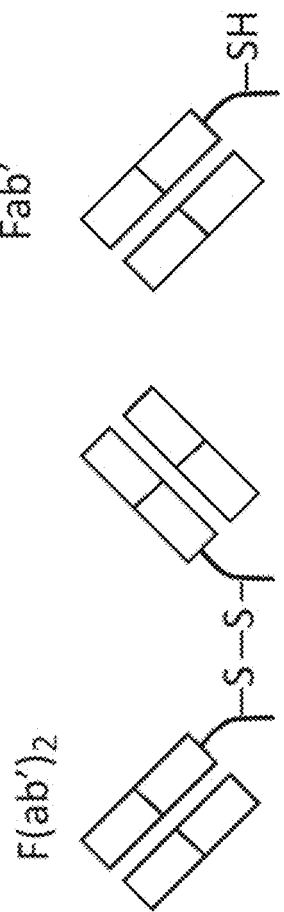
Figure 10D:
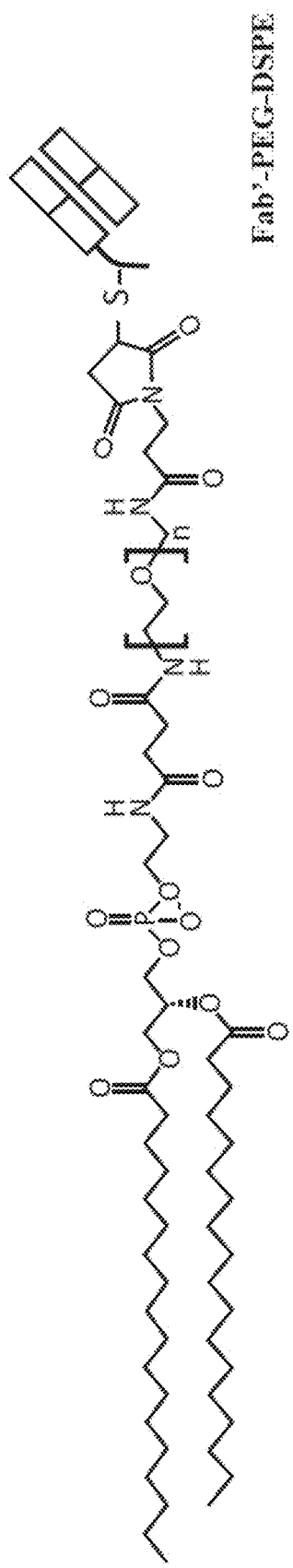
Figure 10A:
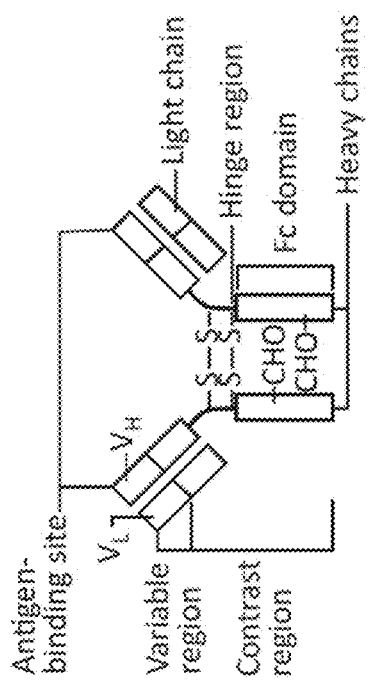

In addition, the model also predicted the limitations of ligand affinity as experimentally observed by Zhou and associates, where ultrahigh affinity anti-EGFR scFv is unnecessary for optimal nanoparticle targeting(93). Zhou empirically detected an increase of 24% in targeted liposomal cell association when comparing surface attached C10 scFv (264 nM $K_D$) to 224 scFv (0.94 nM $K_D$). Using the listed $K_D$'s, the model precisely predicted a 23.7% increase at v=74 (valence evaluated by the paper). Based on the model for F5 scFv, the affinity must be improved by an order of 5 magnitudes to merely increase cell association by 2-fold (FIG. 7).

How can cell association be increased? As evidence by equations 5-3b and 5-3d, $C_{Beq}$ is exponentially proportional to $R_{eq}$ which is exponentially proportional to $R_T$. Hence, increasing the total receptor will in effect increase the concentration of bound nanoparticles. This hypothesis was experimentally examined with dual-targeted immunoliposomes, showing additive uptake effects. In addition, quite simply, the liposomal uptake in cells directly correlates with expression level, ie SK-BR-3 cells>BT-474 cells. Still, the overall uptake, despite being higher, is not quite valuable in applications that rely mainly on increased accumulation for bioactivity since the increase is marginal. However, applications where the receptor expression level is uncertain, such as drug delivery to tumors since expressed receptors can be both heterogeneous and transient, may still be an avenue worth pursing for dual-targeted systems.

Optimizing Cell Association, Drug Delivery, and Efficacy

In addition to examples targeting cells expressing HER2 or EGFR, the model has been expanded to design and optimize the uptake efficiency of ligand-based drugs and nanomedicines relative to ligand surface valency, receptor expression level, mono-targeting as well as dual-targeting to multiple receptors, multi-targeted and multi-valent, and ultimately the consequential biological activity in the delivery of drugs for any ligand and to any antigen target.

Cell association, drug uptake, and cytotoxicity experiments have validated aspects of the model for HER2-targeted lipid nanoparticles to HER2-expressing cells. Likewise, the model may be applied to any ligand and to any antigen target. Equilibrium dissociation constants and total receptors on a cell are measurable parameters through various quantification assays. These parameters are often disclosed in the literature, especially for antibodies and established cell lines. For example, ranges of equilibrium dissociation constants in the literature are abciximab 5 nM, adalimumab 0.05-0.1 nM, alemtuzumab 3-10 nM, atezolizumab 0.4 nM, avelumab 0.7 nM, basiliximab 0.1 nM, belimumab 0.1-0.3 nM, benralizumab 0.016 nM, bevacizumab 0.5-20 nM, bezlotoxumab 0.02-0.04 nM, blinatumomab 1.5 nM, brentuximab 0.2 nM, brodalumab 0.24 nM, canakinumab 0.02-1.3 nM, certolizumab 0.09 nM, cetuximab 0.1-0.4 nM, daclizumab 0.3-0.5 nM, daratumumab 4.4 nM, denosumab 0.003 nM, dinutuximab 11-12 nM, dupilumab 0.01-0.03 nM, durvalumab 0.022 nM, eculizumab 0.12 nM, elotuzumab 30-45 nM, emicizumab 900-1800 nM, evolocumab 0.016 nM, golimumab 0.018 nM, ibritumomab 17 nM, idarucizumab 0.0021 nM, infliximab 0.1-0.45 nM, inotuzumab 0.12-0.15 nM, ipilimumab 1-10 nM, ixekizumab 0.0018 nM, mepolizumab 0.0042 nM, natalizumab 0.3 nM, necitumumab 0.32 nM, nivolumab 2-3 nM, obiltoxaximab 0.33 nM, obinutuzumab 4 nM, ocrelizumab 0.47-1.2 nM, ofatumumab 3-6 nM, olaratumab 0.33 nM, omalizumab 2-8 nM, palivizumab 1 nM, panitumumab 0.05 nM, pembrolizumab 0.029 nM, pertuzumab 9-15 nM, ramucirumab 0.05 nM, ranibizumab 0.19 nM, raxibacumab 1-4 nM, reslizumab 0.081 nM, rituximab 5-11 nM, sarilumab 0.054 nM, secukinumab 0.06-0.37 nM, siltuximab 0.034 nM, tocilizumab 1-3 nM, trastuzumab 1-14 nM, and EGF & TGFα 2-3 nM.

Optimal Multi-Valent Binding: For Any Ligand and to Any Antigen Target

To design multi-targeted multi-valent nanoparticles with optimal cell association, drug delivery, and efficacy, data discloses concentration profile examples of the cell associated particle concentration at equilibrium ($C_{Beq}$) as a function of $C_{Beq}(v, f_X, R_T, K_D, K_X)$. Examples depict dual-targeted multi-valent nanoparticles to dual receptors where each ligand/receptor may have unique $R_T$, $K_D$, and/or $K_X$. For multi-targeting such as dual-targeting nanoparticles, additive and synergetic binding benefits were explored. For optimal cell association, of design interest are the peak $C_{Beq}$ and its corresponding valences. Table 3 below shows the optimal valencies from application of the model to particles with two ligands binding to two different receptors on a target cell.

TABLE 3

Optimal Multi-Targeted Multi-Valent Binding: For Any Ligand and to Any Antigen Target
Optimal Multi-Valent Binding: Dual-Targeted

| $K_D$ (nM) | | Valence (Ligands/Particle) | | | | | |
|---|---|---|---|---|---|---|---|
| Ligand 1 | Ligand 2 | HHa | HMa | MMa | HHs | HMs | MMs |
| 100 | 100 | 17 | 17 | 21 | 13 | 10 | 15 |
| 100 | 10 | 16 | 17 | 20 | 13 | 10 | 15 |
| 100 | 1 | 16 | 17 | 19 | 13 | 10 | 15 |
| 100 | 0.1 | 15 | 17 | 19 | 13 | 10 | 15 |
| 10 | 10 | 16 | 16 | 19 | 12 | 9 | 13 |
| 10 | 1 | 15 | 16 | 18 | 12 | 9 | 13 |
| 10 | 0.1 | 14 | 16 | 17 | 12 | 9 | 13 |
| 1 | 1 | 14 | 14 | 17 | 10 | 8 | 12 |
| 1 | 0.1 | 13 | 14 | 16 | 10 | 8 | 12 |
| 0.1 | 0.1 | 13 | 13 | 15 | 9 | 7 | 11 |

Example 2. Engineering of HER2-Targeted and EGFR-Targeted Lipid Particles, Uptake Efficiency and Effect An array of anti-HER2, anti-EGFR, and dual-targeted lipid nanoparticles at varying ligand valencies were formulated with receptor-specific targeting against cell lines expressing HER2 and/or EGFR. For HER2-targeting, liposomes were functionalized with an antigen-binding fragment (Fab') derived from trastuzumab or F5 single-chain variable fragment (scFv). For EGFR-targeting, liposomes were functionalized with a Fab' derived from cetuximab, or with epidermal growth factor (EGF), or transforming growth factor alpha (TGFα). The surface attachment of ligand conjugates onto liposomes was achieved by the micelle transfer method or a novel sequential micelle transfer—conjugation method. Through a combination of both the sequential micelle transfer—conjugation and the micelle transfer methods, dual-targeted immunoliposomes of various ligand ratios of anti-HER2 F5 scFv and anti-EGFR cetuximab-Fab' were constructed. (See FIGS. 10A to 13B.) EGF and TGFα were investigated as potential targeting groups for liposomal delivery to EGFR-expressing cell lines. Cell association, uptake, and cytotoxicity studies were performed on a panel of human breast cancer cell lines that express either or both HER2 and EGFR at different expression levels.

For HER2-overexpessing and EGFR-overexpressing cell lines, the receptor-mediated uptake studies confirmed the observation that increasing ligand valency per liposome increases targeted uptake until saturation (trastuzumab, F5 scFv, and cetuximab). For ligand surface valencies at optimum binding and higher, as well as high liposomal concentration in incubation, there is roughly a 1:1 ratio of ligands to expressed receptors for MCF-7/HER2, BT-474, SK-BR-3, and MDA-468 cells. In addition, the accumulation of liposomes and ligands for anti-HER2 and anti-EGFR dual-targeted immunoliposomes were roughly additive of their mono-targeted counterparts in BT-474 and MKN-7 cells. No antagonistic effects were observed from the additional of a non-targeted ligand in all cell lines except for SK-BR-3 cells unless beyond 10 anti-EGFR ligand per liposome, where anti-EGFR ligands decreased overall uptake. Despite the additive uptake effect, dual-targeted liposomal delivery of doxorubicin to cell lines expressing HER2 and EGFR was only slightly better in the inhibition of cell proliferation.

Engineering Antigen-Targeted Lipid Nanoparticles

To study the receptor-specific targeted drug delivery of liposomes against cells lines expressing HER2 and/or EGFR, an array of anti-HER2, anti-EGFR, and dual-targeted lipid nanoparticles at varying ligand valencies (trastuzumab, F5 scFv, cetuximab, EGF and TGFα) were formulated. The various engineered liposomal formulations served as probes to help understand the uptake efficiency of liposomes relative to ligand surface valency and receptor expression level, mono-targeting as well as dual-targeting to multiple receptors, intracellular trafficking, and ultimately the consequential biological activity in the delivery of drugs. For receptor-specific targeting, sterically stabilized liposomes were functionalized with the attachment of anti-HER2 and/or anti-EGFR ligands. Liposomes were approximately 80-120 nm in diameter, composed of 1,2-distearoyl-sn-glycero-3-phosphocholine (DSPC), cholesterol, 1,2-distearoyl-sn-glycero-3-phosphoethanolamine-N-[methoxy(polyethylene glycol)-2000] (PEG-DSPE), and a fluorescent lipophilic tracer 1,1'-dioctadecyl-3,3,3',3'-tetramethylindodicarbocyanine perchlorate (DiD), or 3,3'-dioctadecyloxacarbocyanine perchlorate (DiO). For cell viability and tumor growth inhibition experiments, doxorubicin or paclitaxel were also encapsulated.

Amphiphilic targeting ligand conjugates synthesized by maleimide chemistry consisting of a hydrophilic polymer spacer PEG between a lipid anchor DSPE and a ligand group were attached to the surface of liposomes to offer receptor-specific targeting. The conjugation of ligands such as antibody fragments by reactions between maleimide derivatives and thiols using naturally occurring cysteine residue, engineered C-terminal cysteine, or thiolated with Traut's reagent provide strong stable thioether bonds. Reactions with the cysteine on antibody fragments can offer ideal orientation, distant from antibody binding site, minimizing interference with binding. A polymer linker like PEG also helps with the orientation, extending the ligand far enough from the PEG shielding so the ligand are accessible to receptors on cells.

Conjugates of Antibody Fragments and Growth Factors

Fab' conjugates of cetuximab and trastuzumab with 1,2-distearoyl-sn-glycero-3-phosphoethanolamine-N-[maleimide(polyethylene glycol)-2000]) (Mal-PEG-DSPE) were synthesized as previously described(35, 36), taking advantage of the naturally occurring cysteine residue of Fab'. Briefly, cetuximab and trastuzumab IgG were cleaved with pepsin to two antigen-binding fragments connected by disulfide bonds (Fab$_2$), reduced with cysteamine to Fab', and conjugated to Mal-PEG-DSPE (FIG. 10A-10D). The yielded efficiency of Fab'-PEG-DSPE confirmed by size-exclusion chromatography and SDS-PAGE was a reasonable 25-50%. Unfortunately, Fab' conjugates derived from Mal-PEG-DSPE manufactured by Avanti Polar Lipids poorly incorporated to the surface of liposomes by the micelle transfer method.

Figure 11A:
FIGS. 11A and 11B show a schematic of steps in a synthesis of a peptide or protein ligand (such as EGF or TGFα) to PEG-DSPE as a means of attaching the ligand to a lipid surface layer of a ligand-drug particle.
Figure 11B:
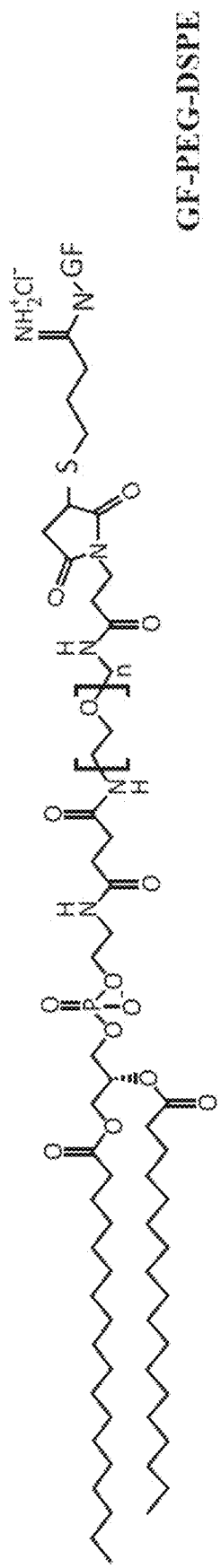

Due to the lack of free cysteine residues, EGF and TGFα were thiolated with Traut's reagent before conjugation to Mal-PEG-DSPE (FIG. 11A-11B). Similar to the conjugation with Fab', the yielded growth factor-PEG-DSPE was 25-50% efficient as confirmed by size-exclusion chromatography and SDS-PAGE. 100% conjugation efficiency was achievable when the growth factors were reacted with higher concentrations of Traut's reagent (>500 fold), but the ligand conjugates were prone to crosslink resulting in poor receptor binding. F5 scFv conjugated to Mal-PEG-DSPE was manufactured by the National Cancer Institute as previously described(38, 42). The surface attachment of ligand conjugates onto liposomes was achieved by the micelle transfer method or the sequential micelle transfer—conjugation method.

Figure 12A:
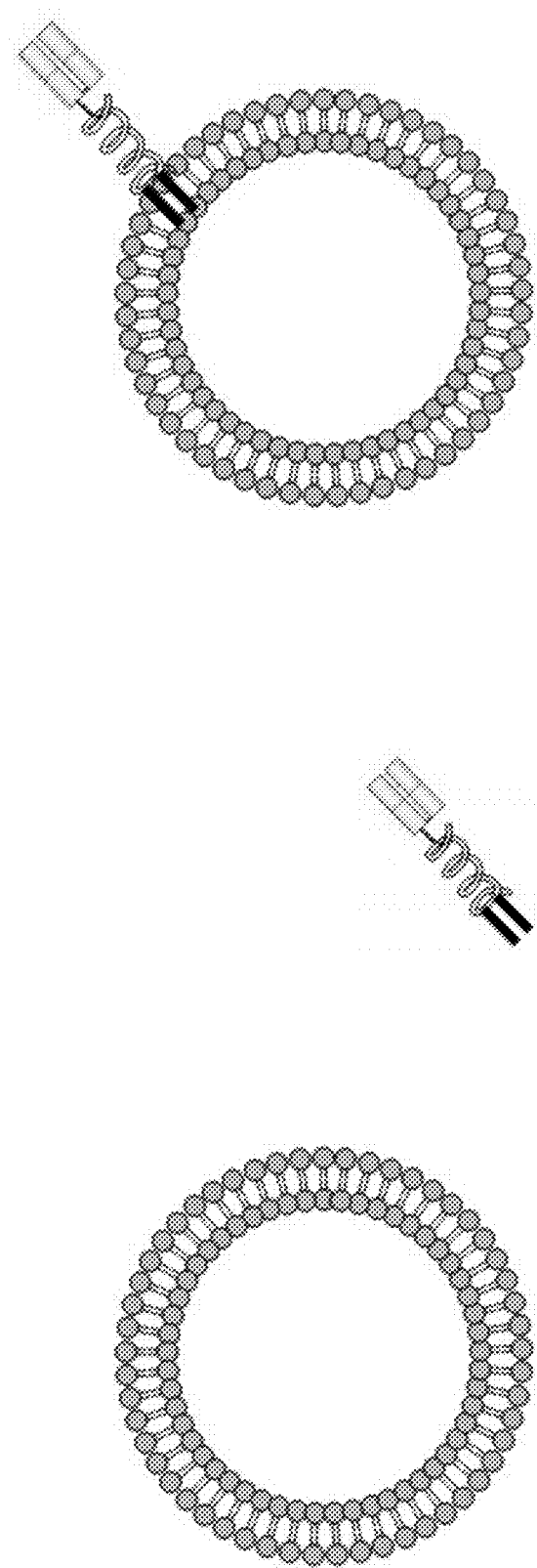
FIGS. 12A and 12B provide schematics showing how a ligand-PEG-DSPE compound can be incorporated into a lipid surface layer of a liposome particle, by a micelle transfer method (FIG. 12A) or by a sequential micelle transfer—conjugation method (FIG. 12B).
Figure 12B:
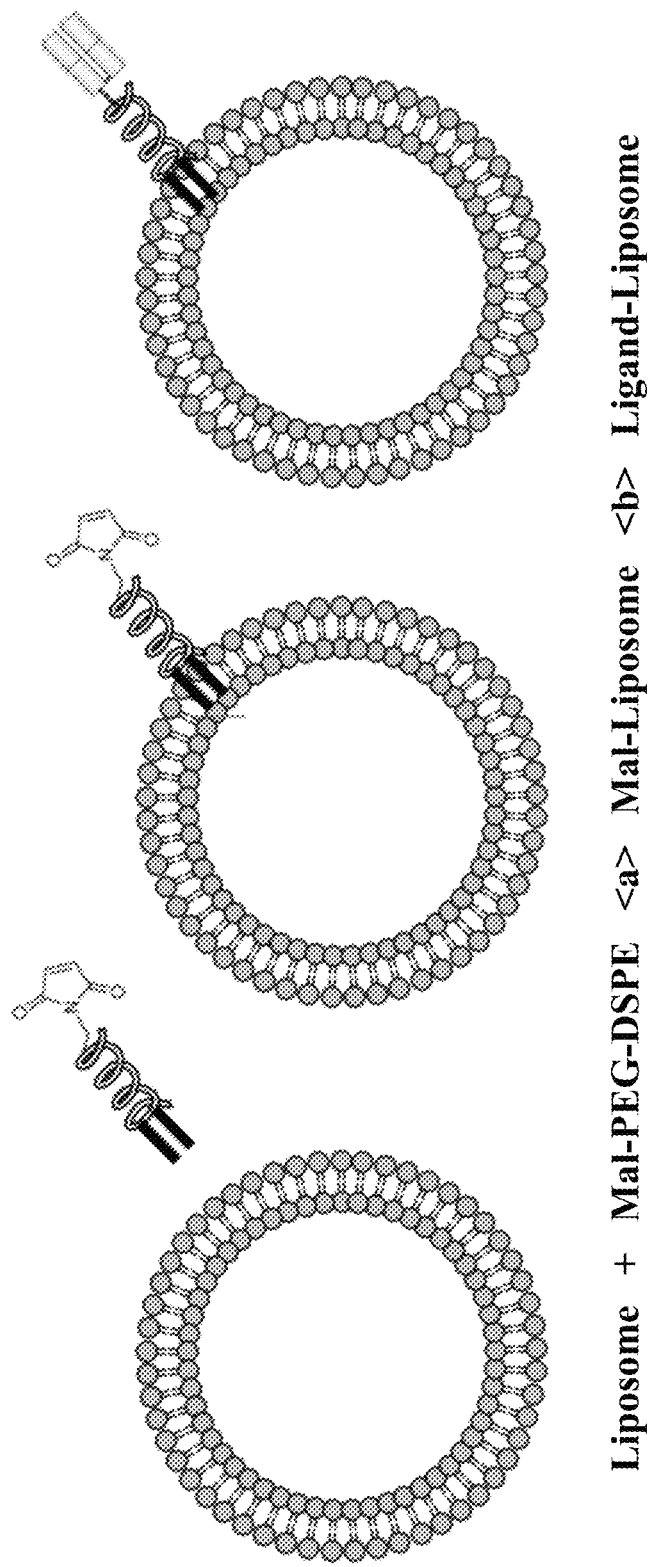

Ligand Conjugation onto Liposomes by the Micelle Transfer Method and Sequential Micelle Transfer—Conjugation Method Through the micelle transfer method(35, 44), micellar conjugates of the ligand and an amphiphilic lipid co-incubated with preformed liposomes spontaneously insert themselves into liposome bilayers without the loss of the liposome integrity(47), providing a rapid and simple method for transforming non-targeted liposomes into antibody-targeted liposomes(48, 49) (FIG. 12A-12B). Insertion is performed at 50-60° C., so the denaturation of protein ligands is a concern, but longer overnight incubation at 37° C. is also possible(34, 48). Liposomes remain mostly unaltered through conjugations, and the techniques have shown to be simple and reproducible.

In the experiments, insertion efficiency for ligand conjugates of F5 scFv-PEG-DSPE, EGF-PEG-DSPE and TGFα-PEG-DSPE onto liposomes via the micelle transfer method (35, 44) was highly efficient (90-100%). Unfortunately, the insertion efficiency of Fab'-PEG-DSPE from trastuzumab and cetuximab onto liposomes was low (5-10%). No more than 10 Fab' per liposome was possible despite an excessive concentration of Fab'-PEG-DSPE incubation, and receptor-specific cell association was low. Previously attempts of the micelle transfer of Fab'-PEG-DSPE were more successful using Mal-PEG-DSPE manufactured by Shearwaters Polymers(35, 36) instead of the current available stock from Avanti Polar Lipids, but they are no longer in production.

Figure 13A:
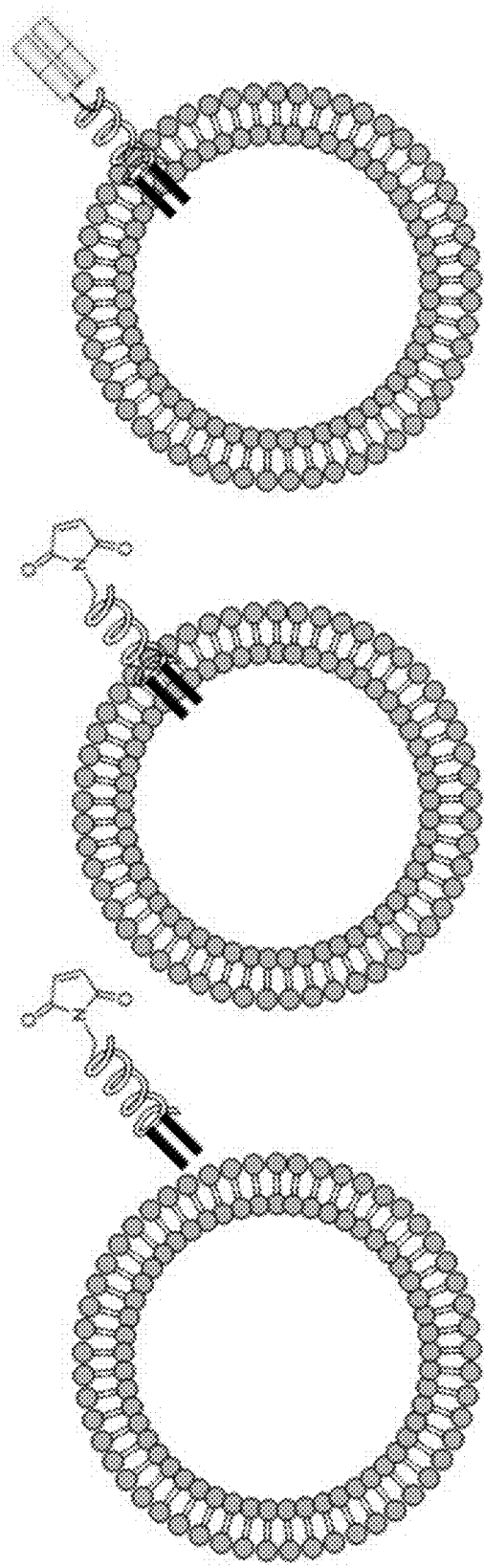
FIGS. 13A and 13B provide schematics of constructing two antibody ligand dual-targeted ligand-drug liposome particles via a micelle transfer-conjugation method.
Figure 13B:
Figure 14A:
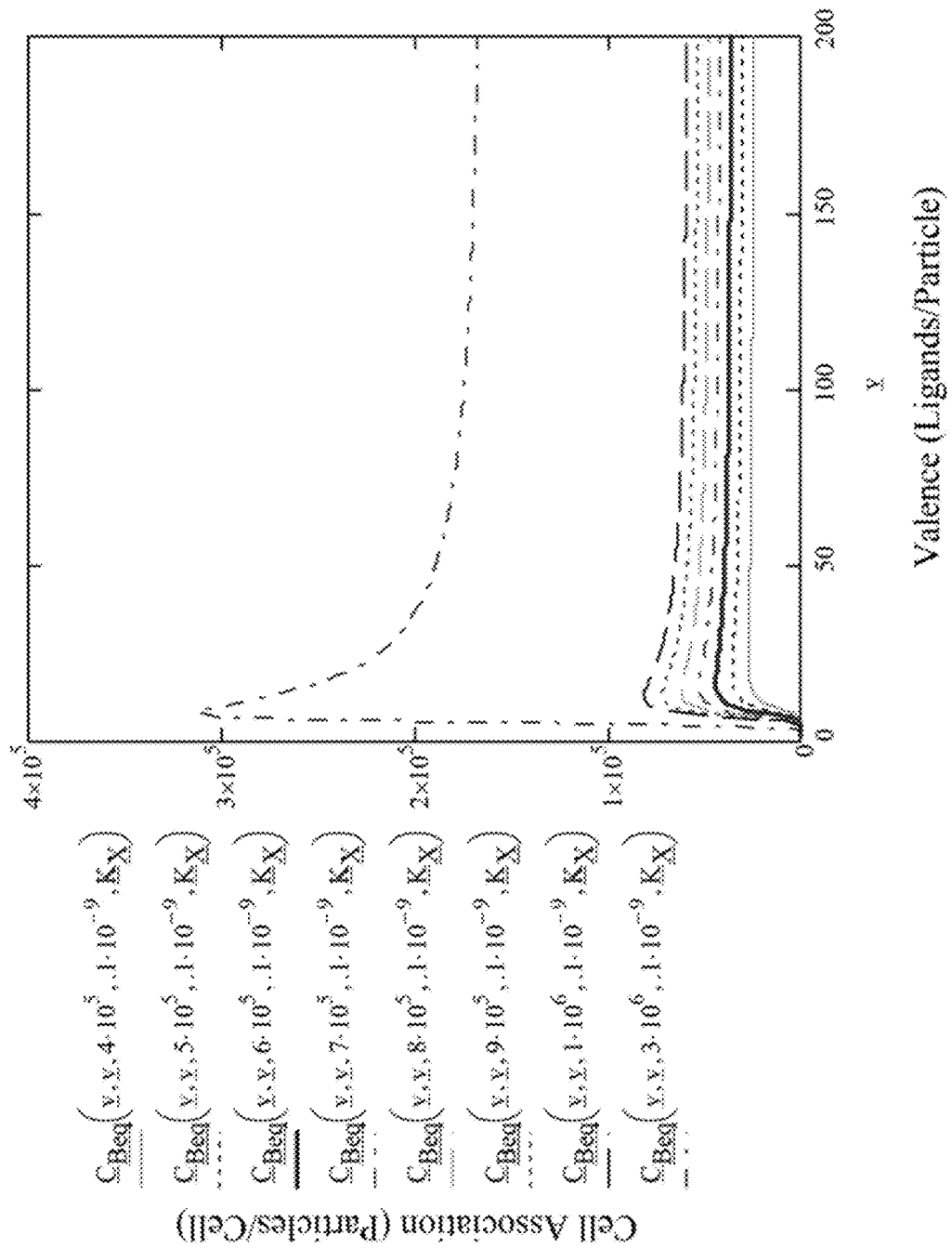
FIGS. 14A-14F show concentration profile examples of the cell associated particle concentration at equilibrium ($C_{Beq}$) as a function of $C_{Beq}(v,fx,R_T,K_D,K_X)$ under different conditions. Plots of cell associated particle concentration at equilibrium ($C_{Beq}$) against valency (ligands/particle) are provided. For optimal cell association, of design interest, for example, are the peak $C_{Beq}$ and its corresponding valences.
Figure 14B:
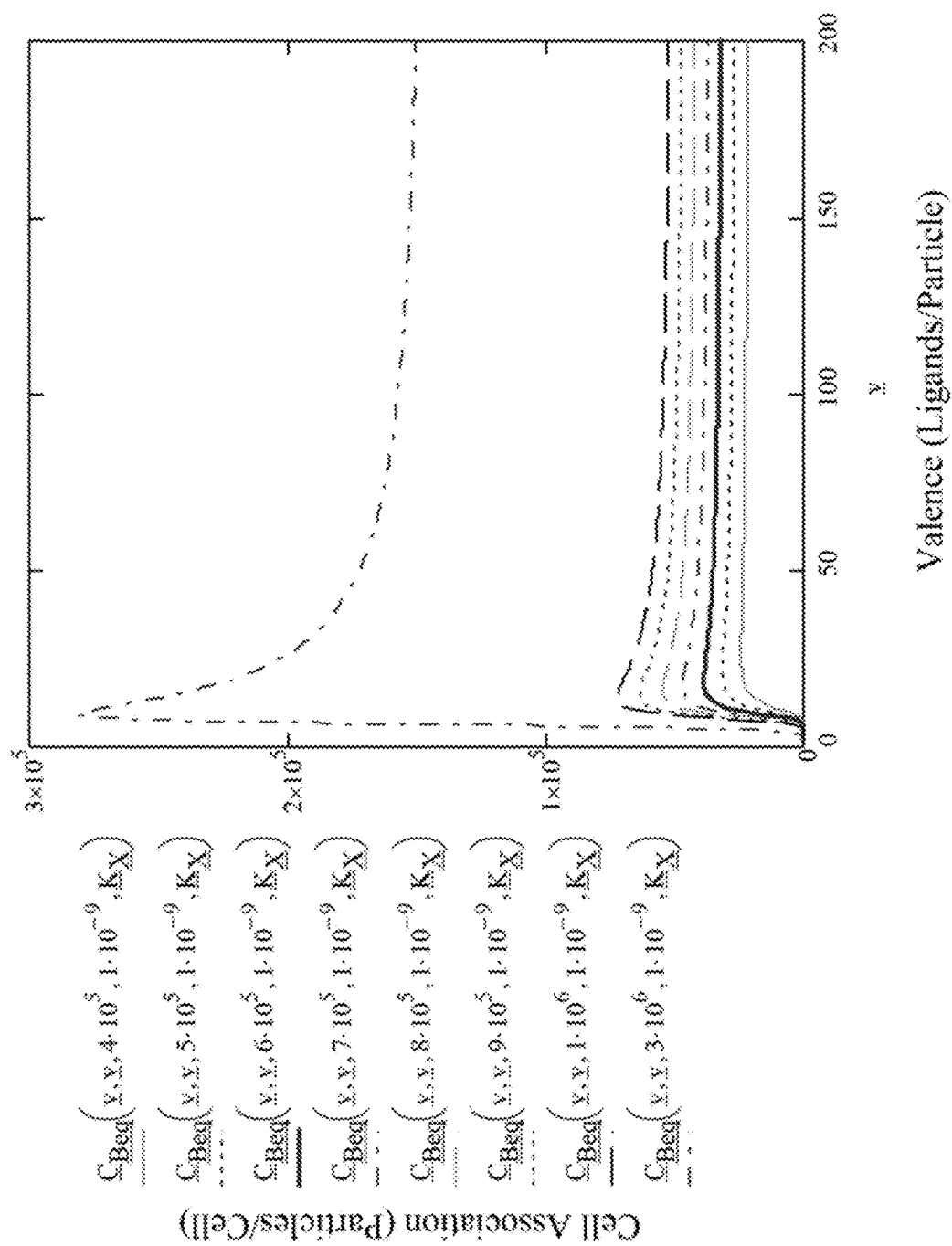
Figure 14C:
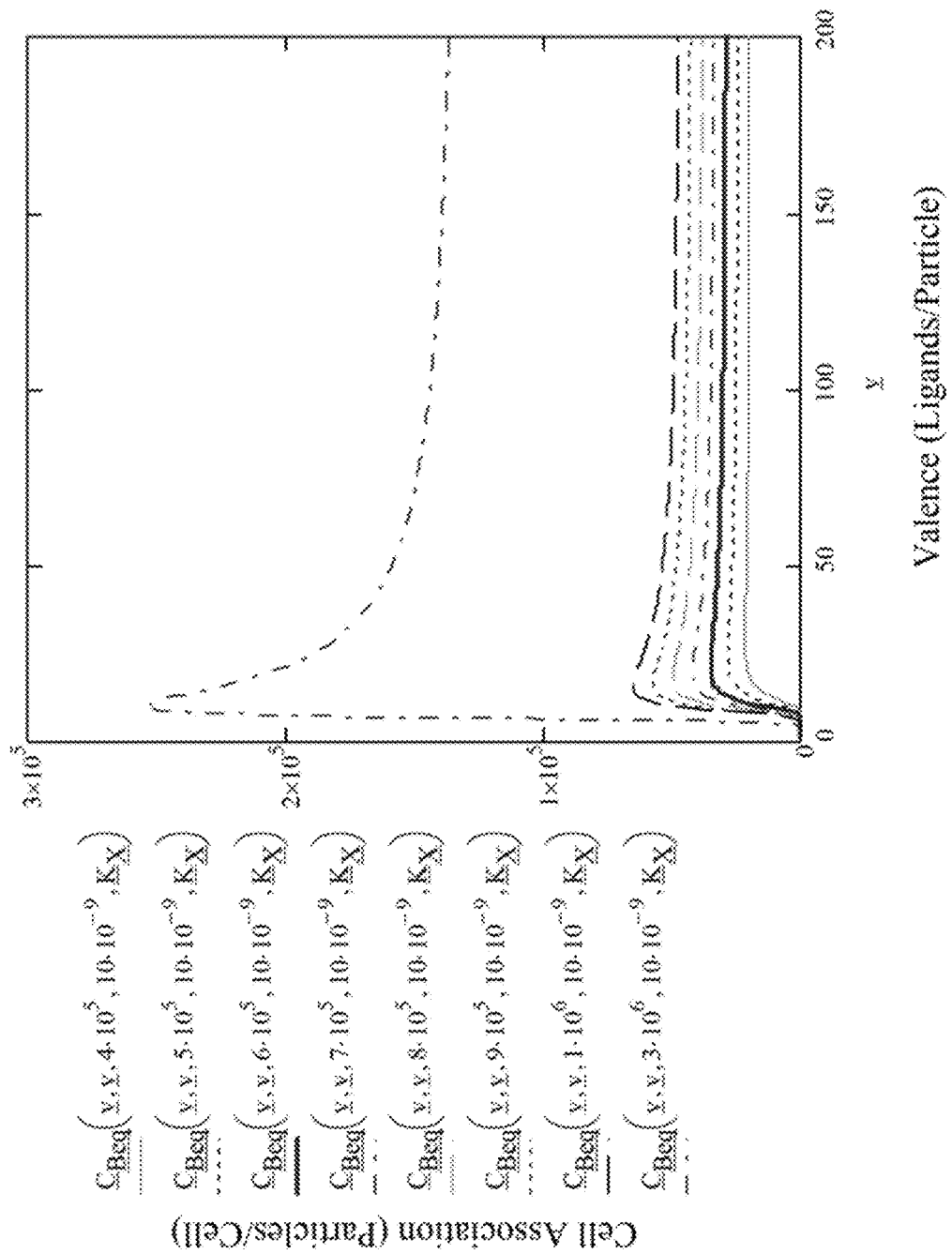
Figure 14D:
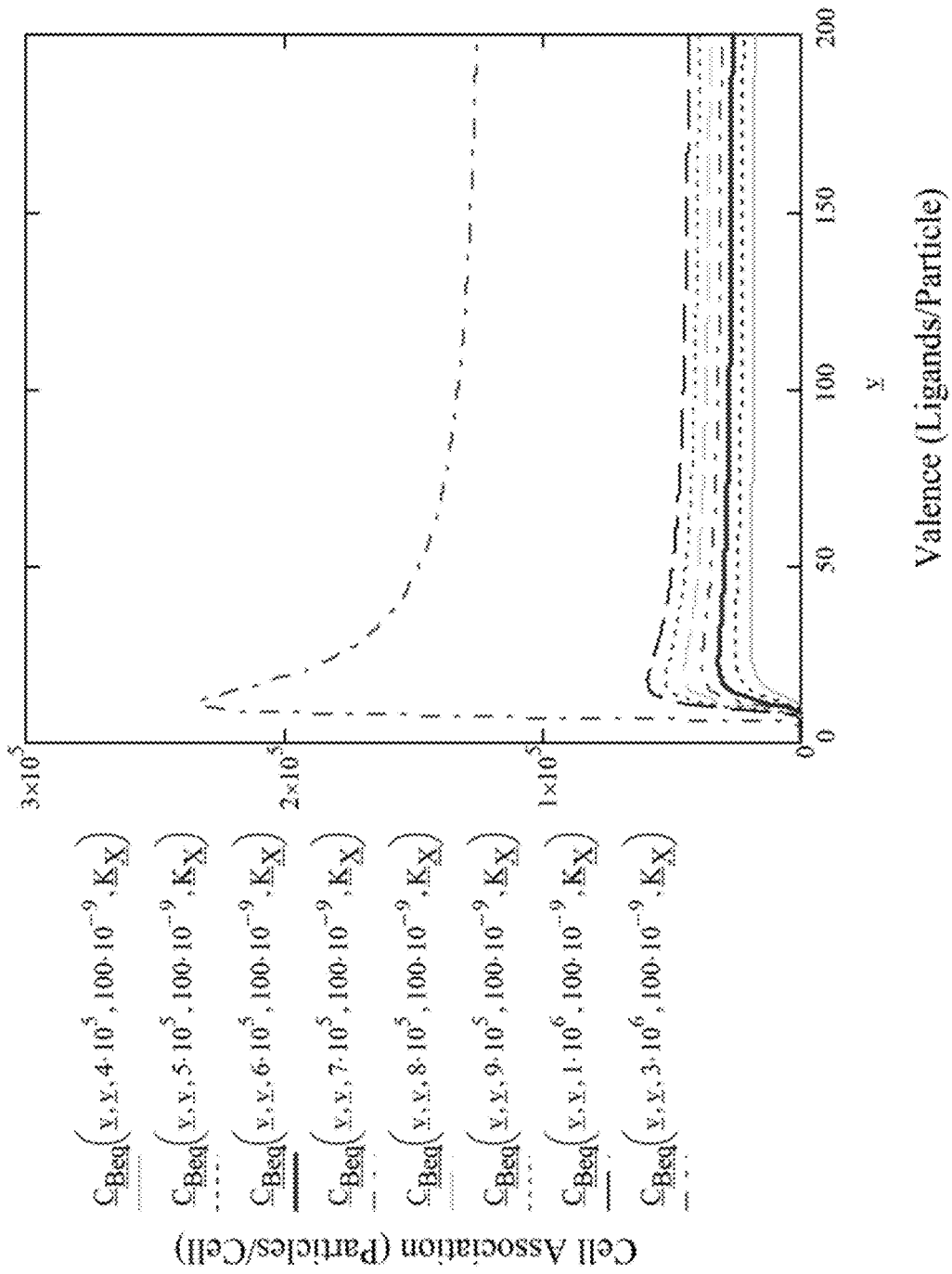
Figure 14E:
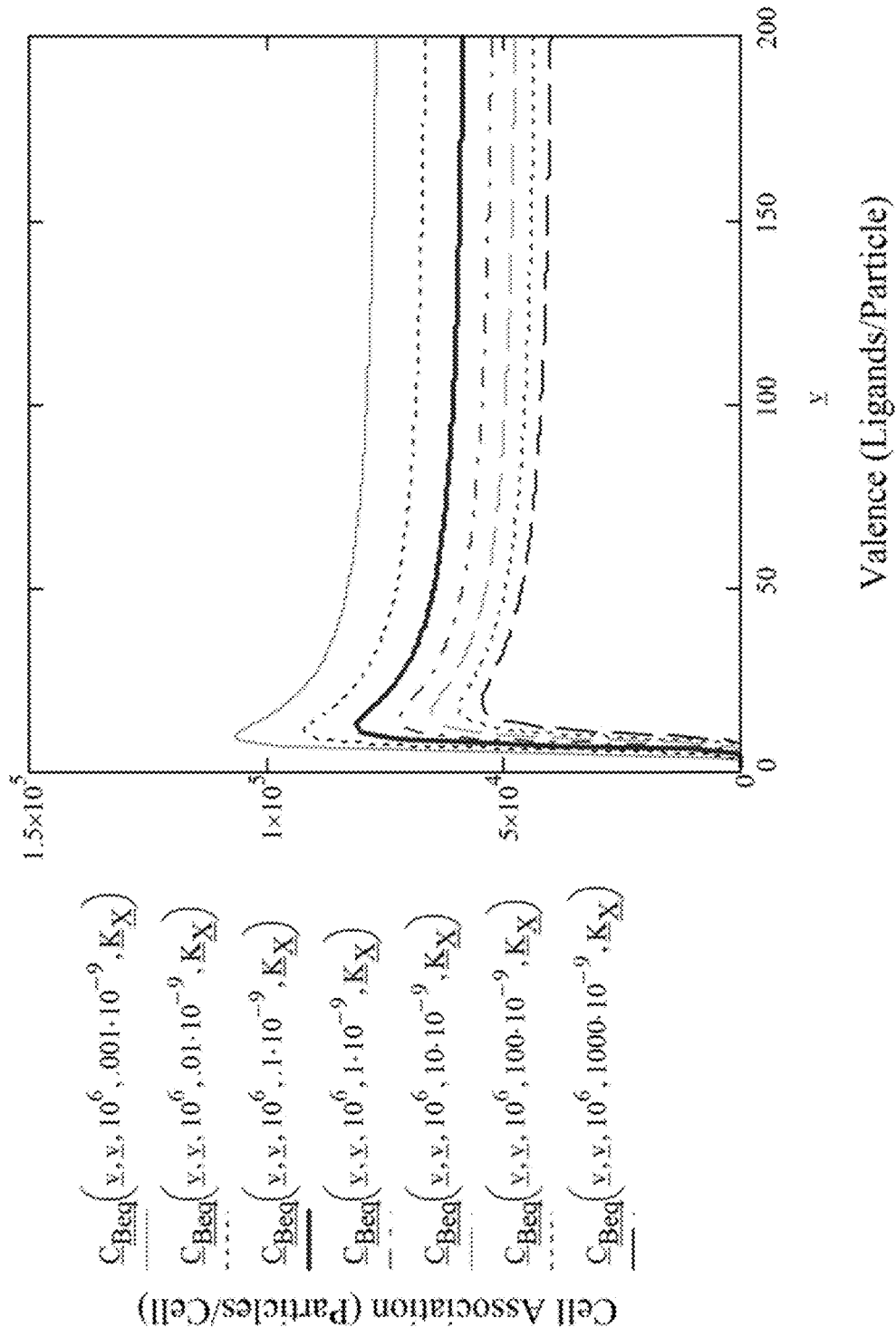
Figure 14F:
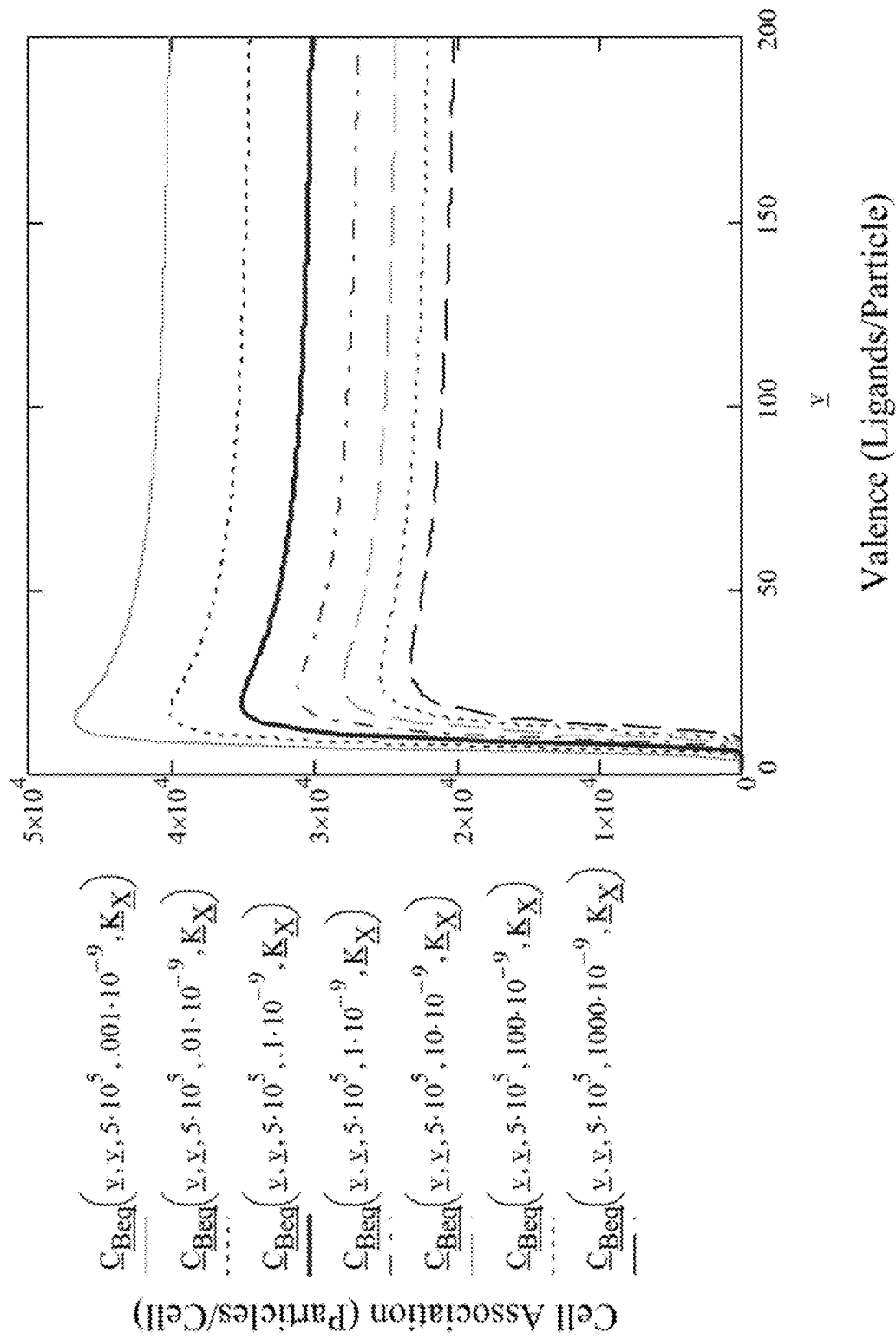
Figure 15A:
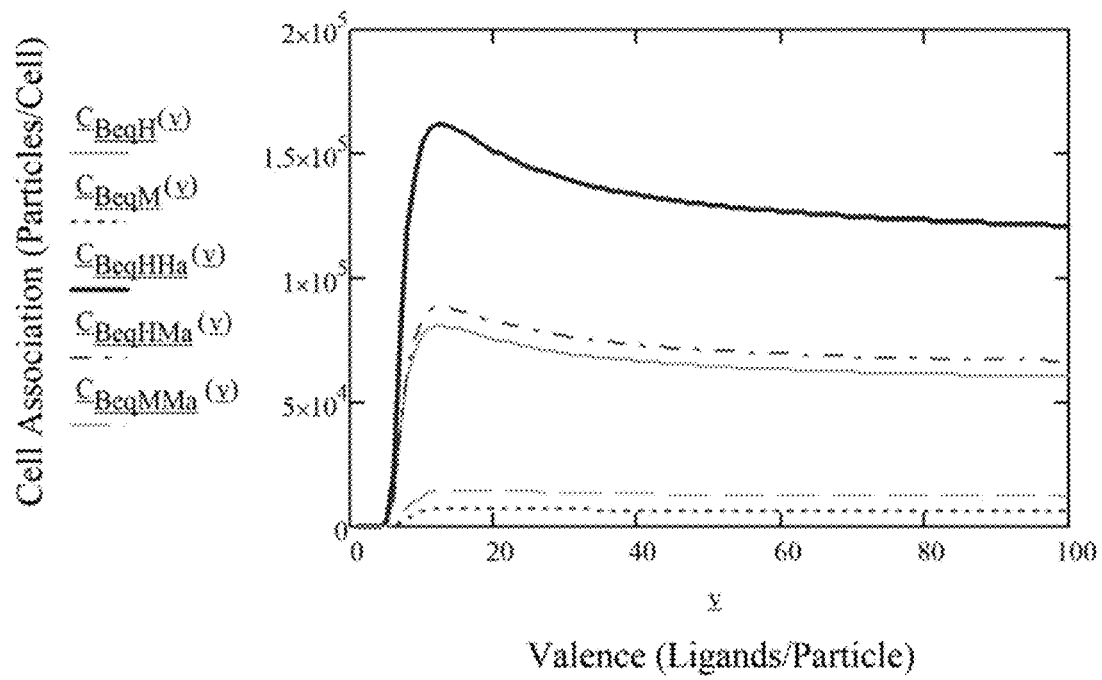
FIGS. 15A-15D show plots of cell associated particle concentration at equilibrium ($C_{Beq}$) against valency (ligands/particle) for a multi-targeted multi-valent crosslink binding model under different conditions. These examples depict dual-targeted multi-valent nanoparticles to dual receptors where each ligand/receptor may have unique $R_T$, $K_D$, and/or $K_X$. Additive and synergetic binding benefits were explored. For optimal cell association, of design interest are, for example, the peak $C_{Beq}$ and its corresponding valences.
Figure 15B:
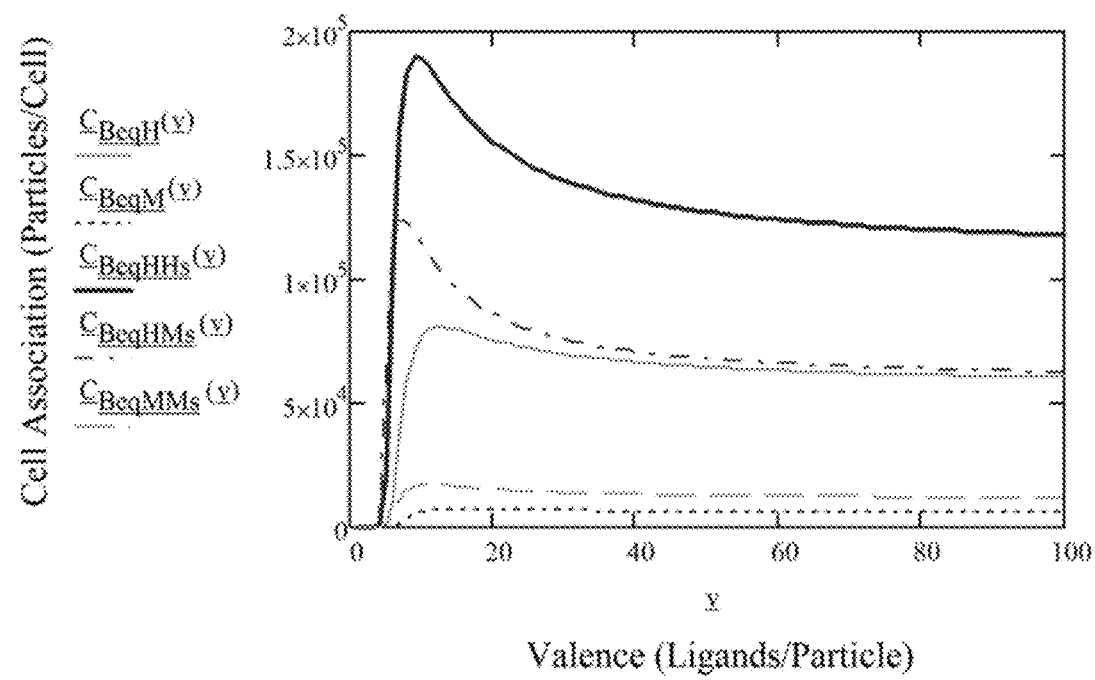
Figure 15C:
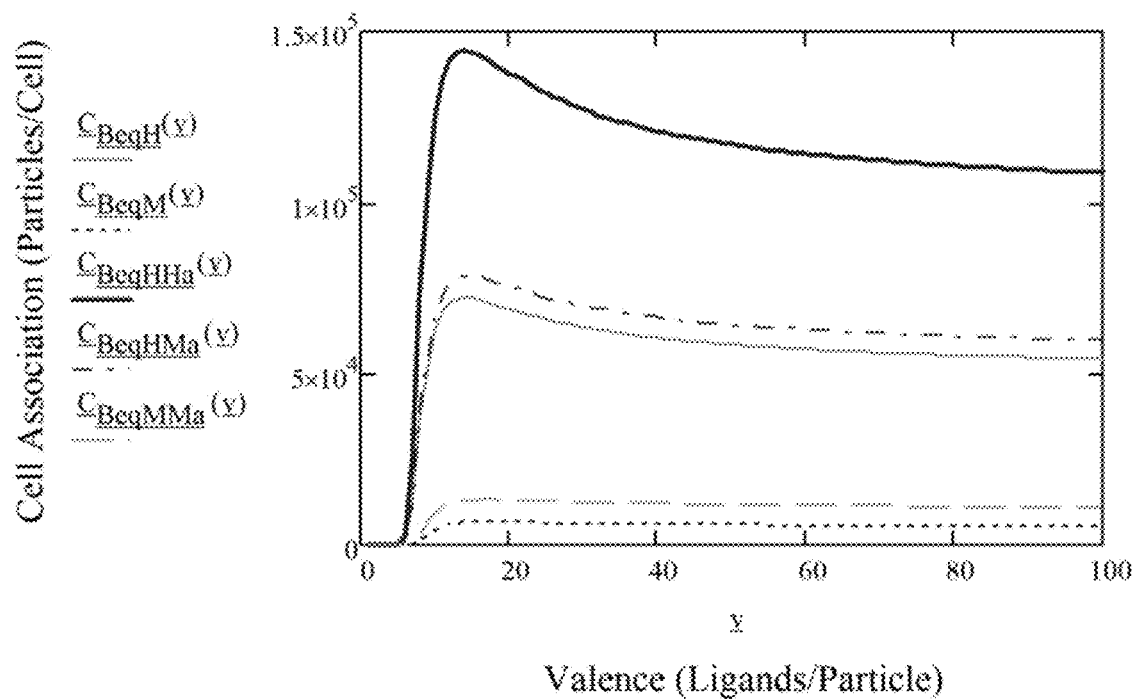
Figure 15D:
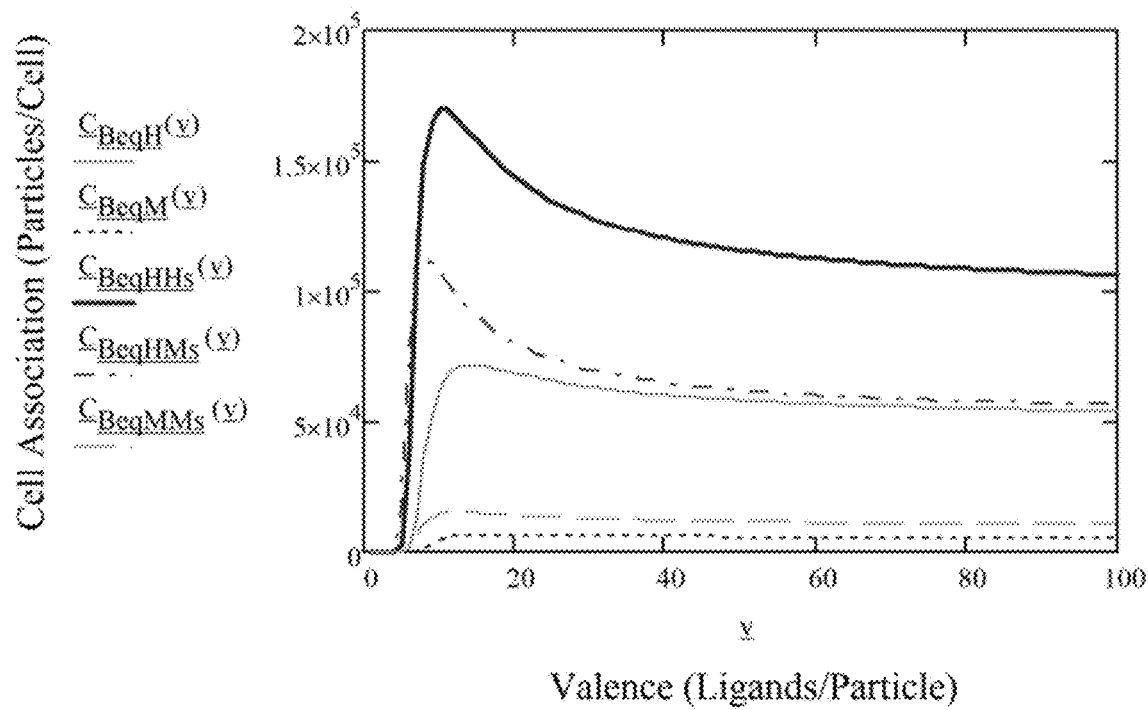

Due to the low transfer of Fab'-PEG-DSPE synthesized from Mal-PEG-DSPE by Avanti Polar Lipids onto liposomes by the micelle transfer method, a novel sequential micelle transfer—conjugation method was developed. IgG (cetuximab & trastuzumab) were cleaved with pepsin, reduced with cysteamine, and conjugated to liposomes micelle transferred with Mal-PEG-DSPE (FIG. 13A-13B). Through this method, a range of 0-200 Fab' per liposome at approximately 25-50% efficiency was achieved. Approximately 50 Fab' per liposome was conjugated for every 0.25% Mal-PEG-DSPE transferred. Attempts of higher valencies (ie, >1% Mal-PEG-DSPE transferred) often resulted in liposomal precipitation.

Hence, Mal-PEG-DSPE available from Avanti Polar Lipids conjugated to small ligands (F5 scFv, EGF, and TGFα) is effective for liposomal insertion by the micelle transfer method, but is also effective for Fab' if Mal-PEG-DSPE is sequential micelle transfer—onto liposomes prior to Fab' conjugation. Another benefit of the sequential micelle transfer—conjugation method is the reduced exposure of the ligands to high temperature incubations required of micelle transfer. This may help with protein stability. Compared to constructing liposomes pre-consisting of Mal-PEG-DSPE, this method allows for a more controlled means to functionalized pre-existing liposomes. Finally, the method also allows for the serial addition of a second targeting group in the case of anti-HER2 and anti-EGFR dual-targeted.

Anti-HER2 and Anti-EGFR Dual-Targeted Immunoliposomes

Through a combination of both the sequential micelle transfer—conjugation and the micelle transfer methods, dual-targeted immunoliposomes of various ligand ratios of anti-HER2 F5 scFv and anti-EGFR cetuximab-Fab' were achieved. Liposomes were functionalized with cetuximab-Fab' via the sequential micelle transfer—conjugation method, followed by insertion of F5 scFv-PEG-DSPE via the micelle transfer method (FIG. 13A-13B). Based on the optimum ligand valencies for the cell association of mono-targeted immunoliposomes as previously determined by flow cytometry, liposomes of varying ligand valencies of anti-HER2 F5 scFv (0-40 ligands/liposomes), anti-EGFR cetuximab-Fab' (0-60 ligands/liposomes), and combinations of both for dual-targeting were constructed.

Conjugate incorporation efficiency was measured and determined by ImageJ (National Institutes of Health) from SDS-PAGE (Bio-Rad) stained with SYPRO Ruby. Because the conjugation efficiency of cetuximab-Fab' to Mal-PEG-DSPE sequential micelle transfer—conjugated liposomes was variable at 25-50%, lower than the ~100% insertion efficiency of F5 scFv-PEG-DSPE, a range of cetuximab-Fab'-conjugated immunoliposomes were first constructed and quantified for ligand valency. From these, cetuximab-Fab' conjugated liposomes of desired ligand valencies were selected for F5 scFv-PEG-DSPE micelle transfer. Cell association studies showed ligand valency dependent binding of liposomes with cells overexpressing HER2 and/or EGFR, and were further investigated for dose-uptake and cytotoxicity studies.

EGF-Conjugated and TGFα-Conjugated Liposomes

As mentioned previously, EGF and TGFα were thiolated with Traut's reagent, conjugated to Mal-PEG-DSPE, and micelle transferred onto liposomes. An array of liposomes with up to 50 growth factors of either EGF or TGFα per liposome was constructed. Although the cell association and trafficking of EGF and TGFα are well characterized, little has been documented for their EGFR-targeting capabilities as functional groups on liposomes in EGFR-overexpressing cells. Cell association studies of EGF-conjugated and TGFα-conjugated liposomes in EGFR-overexpressing MDA-468 cells were conducted to determine optimum ligand valencies, incubation times, and phospholipid concentrations. MDA-468 cells were incubated with EGFR-targeted liposomes labeled with DiD of varying ligand valencies of EGF (0-50 ligands/liposomes) and TGFα (0-50 ligands/liposomes) at 37° C. for 1-24 hr, 0-750 µM PL, and analyzed by flow cytometry and fluorometry.

Increasing the valency of EGF and TGFα ligands per liposomes correlated to amplified targeted binding in MDA-468 cells until a plateau. Similar to the binding results of other anti-HER2 and anti-EGFR targeted immunoliposomes, maximum binding was achieved at ~20 ligand per liposome for both EGF-conjugated and TGFα-conjugated liposomes. Although the ligand valency ratio dependent uptake was similar for 0-50 ligands per liposomes, the binding of EGF-conjugated liposomes was 10-fold higher than that of TGFα-conjugated liposomes. By increasing the incubation times from 1-11 hr, binding also increased but saturation was not reached. Increasing the phospholipid concentration from 0-750 µM PL showed evidence of a possible plateau. There was a less than a magnitude difference in binding between EGF-conjugated and TGFα-conjugated liposomes at higher incubation times and concentration.

In addition to the cell association analysis by flow cytometry, the uptake of anti-EGFR liposomes encapsulated with doxorubicin in MDA-468 cells was also evaluated by fluorometry. Results correlated with the binding experiments where maximum binding was achieved at ~20 ligands per liposome in a ligand valency ratio dependent uptake fashion, and that EGF-conjugated liposomes had a magnitude of higher binding than TGFα-conjugated liposomes. Because the equilibrium dissociation constants for both ligands are close ($K_D$ 2.2-2.6 nM)(77), one hypothesis that may explain the difference in uptake is due to the sterical hindrance resulting from binding to different epitopes on EGFR(115). Unlike F5 scFv, there binding and internalizing abilities may also be altered by surface attachment to liposomes.

EGF-conjugated and TGFα-conjugated liposomes also exhibited 1-2 magnitude lower cell association than cetuximab-conjugated immunoliposomes as expected since the equilibrium dissociation constant for cetuximab (0.1-0.4 nM)(116) is one magnitude lower than that of the growth factors. With the lower binding of EGF-conjugated and TGFα-conjugated liposomes, it may explain why the plateau is harder to reach despite higher concentrations and incubation times. EGFR is not depleted, insuring a constant stream of binding and uptake. EGF-conjugated and TGFα-conjugated liposomes proved effective in cell association with MDA-468 cells. In addition, the modeling of crosslink multivalent binding of lipid nanoparticles to monovalent receptors can offer some insights on the relationship of equilibrium dissociation constant and cell association.

Cell Association of HER2-Targeted, EGFR-Targeted, and Dual-Targeted Immunoliposomes in HER2-Expressing and EGFR-Expressing Cell Lines To determine the optimum ligand valencies and ligand combinations for HER2-targeted, EGFR-targeted, and dual-targeted immunoliposomes in HER2-expressing and EGFR-expressing cell lines, the targeted binding of immunoliposomes labeled with DiD was evaluated by flow cytometry. Cells were incubated with liposomes of varying ligand valencies of anti-HER2 F5 scFv (0-40 ligands/liposomes), anti-EGFR cetuximab-Fab' (0-40 ligands/liposomes), and combinations of both for dual-targeting at 37° C. for 4 hr (75 µM phospholipid (PL)). The mean fluorescent intensity with a tight spread of $5*10^3$ cells was recorded per liposomal formulation.

In EGFR-overexpressing MDA-468 cells, maximum binding was confirmed at ~20-40 anti-EGFR cetuximab- Fab' per liposome (~500 fold>non-targeted liposomes, NT). There was negligible binding for anti-HER2 F5 scFv-conjugated immunoliposomes (ILS) at all ligand valencies (=NT), and correspondingly no additive binding effects for dual-targeted immunoliposomes (~500 fold>NT). In HER2-overexpressing BT-474 cells, maximum binding was confirmed at ~15-20 F5 scFv per liposome (~400 fold>NT). Binding was low but significant for cetuximab-ILS (~20-40 fold>NT). EGFR has been documented to be moderately expressed in BT-474 cells(123). In comparison to mono-targeted immunoliposomes, dual-targeted immunoliposomes offered no additive binding effects for combinations with 15+F5 scFv per liposome (~400 fold>NT), but appeared to be additive for combinations with 5 F5 scFv per liposome (~300 fold vs. ~200 fold>NT).

In HER2 and EGFR moderately expressing MKN-7 cells, binding was low but significant for HER2-targeted and EGFR-targeted immunoliposomes in comparison to non-targeted liposomes (~300 fold>NT). Similar to liposomal cell association in MDA-468 and BT-474 cells, maximum binding was observed at ~20 cetuximab-Fab' per liposome for EGFR-targeted immunoliposomes and ~15-20 F5 scFv per liposome for HER2-targeted immunoliposomes in MKN-7 cells. Dual-targeted immunoliposomes resulted in higher binding than their mono-targeted counterparts (~500 fold>NT), indicating possible synergistic or additive effects. The cell association studies were quick preliminary tests for targeted functionality and were further investigated in the dose-uptake studies.

For mono-targeted immunoliposomes against HER2 and EGFR, the optimum ligand valencies for maximum binding were in line with previous research(34-37), ~20-40 cetuximab-Fab' per liposome for EGFR-targeted immunoliposomes and ~15-20 F5 scFv per liposome for HER2-targeted immunoliposomes. At maximum cell association, these results also provide a baseline to compare to dual-targeted immunoliposomes for potential additive, synergistic, or antagonistic effects. Because MDA-468 cells overexpress EGFR but negligible HER2, binding was only observed with EGFR-targeted immunoliposomes. Dual-targeted immunoliposomes resulted in similar cell association as EGFR-targeted immunoliposomes, confirming negligible HER2 binding as well as a lack of antagonistic effects from additional non-targeted functional groups or sterical hindrance.

Although BT-474 cells overexpress HER2, they also moderately express EGFR, corroborating with the results for high HER2-targeted and low EGFR-targeted cell association. Interestingly, potential additive effects were observed with dual-targeted liposomes only with low F5 scFv valencies. Again, no antagonistic binding effects were observed for dual-targeted immunoliposomes. MKN-7 cells express moderate levels of both HER2 and EGFR, and accordingly moderate cell association with immunoliposomes targeting either receptor was observed. Dual-targeted immunoliposomes resulted in higher cell association than all mono-targeted counterparts. Hence, immunoliposomes with dual-targeting to HER2 and EGFR may increase cell association with targeted cells when conditions are not optimum, in the case of low F5 scFv valencies in BT-474 cells and moderately HER2-expressing and EGFR-expressing MKN-7 cells. Based on these results, ligand valencies were chosen for uptake studies for further investigation.

Uptake of HER2-Targeted Immunoliposomes and Trastuzumab in Relationship to Receptor Expression Level To investigate whether the accumulation of trastuzumab is higher when attached to immunoliposomes or as a free antibody in HER2-overexpressing cell lines, an uptake study was conducted and evaluated by fluorometry. MCF-7/HER2 and BT-474 cells were oversaturated with trastuzumab labeled with Alexa Fluor 488 (40 nM) or immunoliposomes labeled with DiD (23 trastuzumab-Fab' per liposome, 375 μM PL). After a 4 hr incubation, the total accumulation of trastuzumab as an IgG and trastuzumab-Fab' from the immunoliposomes were comparable in MCF-7/HER2 cells, $5-7*10^5$ ligands per cell (P<0.1). Although the accumulation was significantly different in BT-474 cells, $0.8-1.2*10^6$ trastuzumab ligands per cell (P<0.002), they were in the same range. Results from a dose-uptake study in BT-474 cells for F5 scFv-ILS in the next section also yielded similar uptake levels, $1.0*10^6$ ligands per cell at valence of 15 ligands per liposomes, which is comparable to the amount of ligands delivered from trastuzumab-ILS (P<0.14) and free trastuzumab (P<0.07). These results suggest that multiple ligands on the liposomes may contribute the uptake of the lipid nanoparticles. If only a few ligands are required for uptake, it is more likely that the accumulation of liposomes would be closer to the free trastuzumab accumulation range and hence the ligands delivered from the liposomes would be many folds higher (up to 15-20 fold).

HER2 is overexpressed in the human breast cancer cell lines BT-474 ($10^6$ HER2/cell)(44, 124) and MCF-7/HER2 ($10^6$ HER2/cell)(44, 125). Regardless as a free antibody or conjugated as an antibody fragment onto liposomes, the total accumulation of the trastuzumab ligands is close to a 1:1 ratio of ligands to HER2 expressed on BT-474 and MCF-7/HER2 cells. This raises an interesting question in the targeted delivering of drugs, whether it is more efficient as an antibody-ligand-drug such as trastuzumab emtansine (Roche) or drug-encapsulated liposomal formulations? Typical immunoliposomes (100 nm) can encapsulate $15-40*10^3$ drug molecules per liposome, but may require 15-40 ligands per liposome for optimum delivery(4). Hence, the total maximum accumulation of liposomal particles compared to antibody-drug particles can be 1-2 magnitudes less due to the rate limiting 1:1 ratio of ligands to HER2 expressed. However, in a controlled environment in vitro, immunoliposomes still offer roughly a 3 magnitude advantage in drug delivery over antibody-ligand-drugs (assuming 1:1 ratio) due to the high drug-loading efficiency and large payload of liposomal delivery. The advantage may be even higher in vivo due to other benefits from liposomal delivery compared to antibody-bound delivery, such as increased drug stability, prolonged circulation, and enhanced permeability and retention effect.

Dose-Uptake of HER2-Targeted and EGFR-Targeted Immunoliposomes of Varying Ligand Valence To evaluate the targeted uptake of HER2-targeted and EGFR-targeted immunoliposomes relative to ligand valency, ligand combinations, and lipid concentration, dose-uptake studies were performed with increasing concentrations of liposomes labeled with DiO at 37° C. for 4 hr. Immunoliposomes consisted of varying ligand valencies of anti-HER2 F5 scFv (0-15 ligands/liposomes), anti-EGFR cetuximab-Fab' (0-20 ligands/liposomes), and combinations of both for dual-targeting. Similar studies using immunoliposomes labeled with DiD, loaded with doxorubicin, and slightly different ligand combinations were also evaluated and yielded comparable results (data not shown).

In MDA-468 cells, immunoliposomes with higher cetuximab-Fab' per liposome valencies correlated with higher targeted uptake. 20 cetuximab-Fab' per liposome reached a plateau at ~300 μM PL, resulting in ~$5*10^5$ liposomes and ~$10^6$ cetuximab-Fab' per cell (Table 4). Similarly, there was an accumulation of ~$10^6$ cetuximab-Fab' per cell in all cases for dual-targeted immunoliposomes with 20 cetuximab-Fab' and 0-15 F5 scFv per liposome. Immunoliposomes with varying F5 scFv valencies had no significant uptake compared to non-targeted liposomes.

In HER2-overexpressing SK-BR-3 cells, immunoliposomes with high F5 scFv per liposome valencies correlated with high targeted uptake. 10-15 F5 scFv per liposome reached a plateau at ~200 µM PL, resulting in ~2-3*$10^5$ liposomes and ~3*$10^6$ F5 scFv per cell. Similarly, there was an accumulation of ~2-3*$10^6$ F5 scFv per cell in all cases for dual-targeted immunoliposomes with 10-15 F5 scFv and 0-20 cetuximab-Fab' per liposome. Immunoliposomes with varying cetuximab-Fab' valencies had no significant uptake compared to non-targeted liposomes. There is higher uptake of anti-HER2 targeted immunoliposomes in SK-BR3 cells than in BT-474 cells.

The MDA-468 human breast cancer cell line overexpresses roughly $10^6$ EGFR per cell(126, 127) but negligible HER2, and the SK-BR-3 human breast cancer cell line overexpresses 2-3*$10^6$ HER2 per cell(128, 129) but negligible EGFR. At the plateau, there is roughly a 1:1 ratio of ligands to receptors for both cell lines with their respective overexpressed receptors. Similar to the cell association studies in MDA-468 cells, non-specific anti-HER2 ligands did not interfere with targeted uptake. In the case of anti-HER2 and anti-EGFR dual-targeted immunoliposomes, uptake was not significantly different compared to anti-EGFR immunoliposomes of similar cetuximab-Fab' valencies ($P<0.95$ for E20Hy; $P<0.53$ for E10Hy).

Interestingly in SK-BR-3 cells, non-specific anti-EGFR ligands can interfere with targeted uptake in an antagonistic manner beyond 10 anti-EGFR ligands per liposome. At 10 anti-EGFR ligands per liposome, there is no significant effect. Although mono-targeted cetuximab-immunoliposomes had no significant uptake compared to non-targeted liposomes, in the case of anti-HER2 and anti-EGFR dual-targeted immunoliposomes with 20 cetuximab-Fab' per liposome, uptake was lower for all combinations with F5 scFv compared to mono-targeted counterparts. These results provide evidence that the addition of non-specific ligands may interfere with the uptake of some cell lines such as SK-BR-3, but not others like MDA-468, at high enough of ligand valence. It could also be due to the larger size of Fab' compared to scFv.

Additive Dose-Uptake Effect of Anti-HER2 and Anti-EGFR Dual-Targeted Immunoliposomes To investigate the effects of true dual-targeting, dose-uptake studies were continued on cell lines expressing moderate to high levels of both HER2 and EGFR. In BT-474 cells ($10^6$ HER2 per cell and moderate levels of EGFR(44, 124)), F5 scFv-ILS reached a plateau at ~100-200 µM PL, resulting in ~7*$10^4$ liposomes and ~1*$10^6$ F5 scFv per cell.

At the plateau, there is again roughly a 1:1 ratio of ligands to receptors, similar ratios seen from trastuzumab as an IgG and trastuzumab-Fab' from the immunoliposomes. Immunoliposomes with varying cetuximab-Fab' valencies exhibited low uptake (~2*$10^4$ liposomes/cell), but significantly higher compared to non-targeted liposomes. In the case of anti-HER2 and anti-EGFR dual-targeted immunoliposomes, uptake was significantly higher compared to anti-HER2 immunoliposomes of similar F5 scFv valencies ($P<4*10^{-3}$ for ExH15; $P<8*10^{-5}$ for ExH10; $P<9*10^{-5}$ for ExH5).

The accumulation of liposomes and ligands for dual-targeted immunoliposomes was roughly additive of their mono-targeted counterparts in BT-474 cells (Table 4). Dual-targeted immunoliposomes with 15 F5 scFv and 20 cetuximab-Fab' resulted in 8.3*$10^4$ liposomes per cell, which is also the additive accumulation of mono-targeted 15 F5 scFv-ILS (6.8*$10^4$ liposomes/cell) and 20 cetuximab-ILS (1.5*$10^4$ liposomes/cell). Similarly, dual-targeted immunoliposomes resulted in 1.2*$10^6$F5 scFv per cell, which is also the additive accumulation of mono-targeted F5 scFv (1*$10^6$F5 scFv/cell) and cetuximab-ILS (2*$10^5$F5 scFv/cell, extrapolated from 3*$10^5$ cetuximab-Fab' assuming 15:20 ratio). The additive accumulation of liposomes and ligands for dual-targeted immunoliposomes from their mono-targeted counterparts were close for all ratios, 0-15 F5 scFv and 0-20 cetuximab-Fab' per liposome.

In MKN-7 cells (moderate levels of both HER2 and EGFR), HER2-targeted and EGFR-targeted immunoliposomes did not reach an uptake plateau for any ligand valencies. Immunoliposomes exhibited low uptake (<2*$10^4$ liposomes/cell), but significantly higher compared to non-targeted liposomes, except for 10 cetuximab-Fab' per liposome. In the case of dual-targeted immunoliposomes, uptake was significantly higher compared to anti-EGFR or anti-HER2 immunoliposomes of similar ligand valencies, in line with previous cell association studies ($P<10^{-6}$ for ExH15, ExH10, ExH5, E20Hy, & E10Hy). Similar to the BT-474 cell line, the accumulation of liposomes and ligands for dual-targeted immunoliposomes were roughly additive of their mono-targeted counterparts (Table 4). Dual-targeted immunoliposomes with 15 F5 scFv and 20 cetuximab-Fab' resulted in ~9*$10^3$ liposomes per cell, which is the additive accumulation of mono-targeted 15 F5 scFv-ILS (4*$10^3$ liposomes/cell) and 20 cetuximab-ILS (4*$10^3$ liposomes/cell). Similarly, dual-targeted immunoliposomes resulted in ~1.3*$10^5$F5 scFv per cell, which is the additive accumulation of mono-targeted F5 scFv (6.1*$10^5$F5 scFv/cell) and cetuximab-ILS (5.4*$10^5$F5 scFv/cell, extrapolated from 7.2*$10^5$ cetuximab-Fab' assuming 15:20 ratio). The additive accumulation of liposomes and ligands for dual-targeted immunoliposomes from their mono-targeted counterparts were close for all ratios, 0-15 F5 scFv and 0-20 cetuximab-Fab' per liposome.

TABLE 4

|  | LS/Cell | | Anti-EGFR Lg/Cell | | Anti-HER2 Lg/Cell | |
| --- | --- | --- | --- | --- | --- | --- |
|  | Max | Sum | Max | Sum | Max | Sum |
| BT-474 | | | | | | |
| E0H0/NT | 1.7E3 ± 3.6E2 | | | | | |
| E10H0 | 2.0E4 ± 6.6E3 | | 2.0E5 ± 6.6E4 | | | |
| E20H0 | 1.5E4 ± 4.8E3 | | 3.0E5 ± 9.6E4 | | | |
| E0H5 | 4.0E4 ± 6.0E2 | | | | 2.0E5 ± 3.0E3 | |
| E0H10 | 7.2E4 ± 8.0E3 | | | | 7.2E5 ± 8.0E4 | |
| E0H15 | 6.8E4 ± 7.3E3 | | | | 1.0E6 ± 1.1E5 | |

TABLE 4-continued

| | LS/Cell | | Anti-EGFR Lg/Cell | | Anti-HER2 Lg/Cell | |
|---|---|---|---|---|---|---|
| | Max | Sum | Max | Sum | Max | Sum |
| E10H5 | 6.1E4 ± 2.8E3 | 5.9E4 | 6.1E5 ± 2.8E4 | 5.9E5 | 3.1E5 ± 1.4E4 | 3.0E5 |
| E10H10 | 9.9E4 ± 8.4E3 | 9.1E4 | 9.9E5 ± 8.4E4 | 9.1E5 | 9.9E5 ± 8.4E4 | 9.1E5 |
| E20H5 | 5.6E4 ± 1.8E3 | 5.5E4 | 1.1E6 ± 3.5E4 | 1.1E6 | 2.8E5 ± 8.8E3 | 2.7E5 |
| E20H10 | 9.7E4 ± 4.6E3 | 8.7E4 | 1.9E6 ± 9.2E4 | 1.7E6 | 9.7E5 ± 4.6E4 | 8.7E5 |
| E20H15 | 8.3E4 ± 1.4E3 | 8.3E4 | 1.7E6 ± 2.7E4 | 1.7E6 | 1.2E6 ± 2.1E4 | 1.2E6 |
| MKN-7 | | | | | | |
| E0H0/NT | 1.8E3 ± 4.7E2 | | | | | |
| E10H0 | 2.1E3 ± 2.5E2 | | 2.1E4 ± 2.5E3 | | | |
| E20H0 | 3.6E3 ± 7.8E2 | | 7.2E4 ± 1.6E4 | | | |
| E0H5 | 8.1E3 ± 4.5E2 | | | | 4.1E4 ± 2.3E3 | |
| E0H10 | 4.9E3 ± 2.2E2 | | | | 4.9E4 ± 2.2E3 | |
| E0H15 | 4.1E3 ± 3.3E2 | | | | 6.1E4 ± 5.0E3 | |
| E10H5 | 9.8E3 ± 3.4E2 | 1.0E4 | 9.8E4 ± 3.4E3 | 1.0E5 | 4.9E4 ± 1.7E3 | 5.1E4 |
| E10H10 | 7.9E3 ± 3.3E2 | 7.0E3 | 7.9E4 ± 3.3E3 | 7.0E4 | 7.9E4 ± 3.3E3 | 7.0E4 |
| E20H5 | 1.3E4 ± 6.9E2 | 1.2E4 | 2.5E5 ± 1.4E4 | 2.3E5 | 6.3E4 ± 3.4E3 | 5.9E4 |
| E20H10 | 5.5E3 ± 3.4E2 | 8.5E3 | 1.1E5 ± 6.8E3 | 1.7E5 | 5.5E4 ± 3.4E3 | 8.5E4 |
| E20H15 | 8.5E3 ± 5.7E2 | 7.7E3 | 1.7E5 ± 1.1E4 | 1.5E5 | 1.3E5 ± 8.5E3 | 1.2E5 |
| MDA-468 | | | | | | |
| E0H0/NT | 1.4E4 ± 8.6E3 | | | | | |
| E10H0 | 2.0E4 ± 5.8E2 | | 2.0E5 ± 5.8E3 | | | |
| E20H0 | 5.3E3 ± 2.3E3 | | 1.1E6 ± 4.6E4 | | | |
| E0H5 | 5.3E3 ± 2.0E2 | | | | 2.6E4 ± 1.0E3 | |
| E0H10 | 1.1E3 ± 2.2E2 | | | | 1.1E4 ± 2.2E3 | |
| E0H15 | 8.0E3 ± 2.0E2 | | | | 1.2E5 ± 2.0E3 | |
| E10H5 | 2.7E4 ± 8.5E2 | 2.5E4 | 2.7E5 ± 8.5E3 | 2.5E5 | 1.4E5 ± 4.2E3 | 1.3E5 |
| E10H10 | 2.2E4 ± 1.6E3 | 2.1E4 | 2.2E5 ± 1.6E4 | 2.1E5 | 2.2E5 ± 1.6E4 | 2.1E5 |
| E20H5 | 6.1E4 ± 2.0E3 | 5.8E4 | 1.2E6 ± 4.1E4 | 1.2E6 | 3.1E5 ± 1.0E4 | 2.9E5 |
| E20H10 | 5.3E4 ± 2.6E3 | 5.4E4 | 1.1E6 ± 5.2E4 | 1.1E6 | 5.3E5 ± 2.6E4 | 5.4E5 |
| E20H15 | 5.9E4 ± 2.2E3 | 6.1E4 | 1.2E6 ± 4.3E4 | 1.2E6 | 8.8E5 ± 3.2E4 | 9.1E5 |

Table 4 above shows the accumulation of liposomes (LS) and ligands (Lg) from HER2-targeted, EGFR-targeted, and dual-targeted immunoliposomes (ILS) in BT-474, MKN-7, and MDA-468 cells from dose-uptake studies. Max is the maximum measured accumulation; Sum is the total calculated accumulation from mono-targeted immunoliposomes counterparts. For ExHy ILS, x and y specify the number of ligands per liposome against EGFR (cetuximab-Fab') and HER2 (F5 scFv), respectively, while NT stands for non-targeted (i.e., no ligands).

The dose-uptake experiments were also evaluated on Scatchard plots for cooperativity, which compares the binding affinity with the extent of receptor occupancy. Although Scatchard plots are traditionally used to assess binding, uptake and binding for lipid nanoparticles are directly and proportionally linked with internalizing surface ligands. For all cases where mono-targeted immunoliposomes were incubated with a receptor overexpressing cell line (ie, anti-EGFR in MDA-468, anti-HER2 in BT-474, & anti-HER2 in SK-BR-3), the plot concave downwards indicating positive cooperativity. This implies that the equilibrium dissociation constant increases with occupancy. For all cases where mono-targeted immunoliposomes were incubated with a receptor moderately expressing cell line (ie, anti-EGFR in BT-474, both anti-EGFR and anti-HER2 in MKN-7, lesser extent with anti-EGFR in SK-BR-3), the plot concave upwards indicating negative cooperativity. The equilibrium dissociation constant hence decreases with occupancy. Interestingly, for BT-474 cells, dual-targeted immunoliposomes changes the curvilinear profile, with cooperativity being negative at low concentrations and linear to positive at higher concentrations. The cooperativity for all the liposomal samples is apparent, indicating other possible associating interactions such as multivalent binding.

In HER2-overexpressing and EGFR-overexpressing human breast cancer cell lines, increasing the valency of ligands per liposomes increased targeted uptake until saturation. After which point, increased ligand valency may decrease uptake, maintaining a 1:1 ratio of ligands to receptors. The equal ligands to receptors ratio may be explained by multivalent binding and receptor crosslinking. In such ideal situations with both high receptor expression on the cells and high affinity constants for ligands to receptors, it may be possible that multiple ligands are binding to multiple receptors during the process of receptor-mediated endocytosis. In essence, a liposome is behaving as a multivalent ligand that can multivalent bind and crosslink monovalent receptors expressed on the cells. HER2 have been shown to form clusters in cell membranes which may even increase the chances of crosslink binding(130, 131). In addition, per surface area, there are more receptors available per ligand. Assuming an average cell diameter of 10 μm with $10^6$ receptors and an average liposome diameter of 100 nm with 20 ligands, the receptor to ligand per surface area ratio is 5, meaning that for every ligand there are 5 receptors available to bind. Crosslink multivalent binding of liposomes to clustered receptors is a possible and plausible outcome.

For cell lines that express both receptors such as BT-474 and MKN-7, anti-HER2 and anti-EGFR dual-targeted immunoliposomes can increase the overall accumulation of liposomes and ligands beyond the saturation point of mono-targeted immunoliposomes. In addition, the uptake is roughly additive of their mono-targeted counterparts. Because the uptake of dual-targeted immunoliposomes appears to be additive instead of synergistic, the overall accumulation is only marginally higher (folds, not magnitudes), and hence may result only in marginally increased benefits from increased accumulation. The main advantage may be more of a simplified multi-targeting formulation, where the immunoliposomes can target multiple receptors, and hence effective with more cell lines and accordingly heterogeneous receptor expressing tumors. Only in the SK-BR-3 cell line that the addition of a non-targeting functional group may be antagonistic to uptake at high anti-EGFR ligand valence. Despite that, uptake was only marginally lower.

Cytotoxicity Studies of Doxorubicin-Encapsulated HER2-Targeted, EGFR-Targeted, and Dual-targeted Immunoliposomes In parallel to the dose-uptake studies, cytotoxicity studies with doxorubicin-encapsulated HER2-targeted, EGFR-targeted, and dual-targeted immunoliposomes were also examined for any correlations between increased targeted uptake and toxicity benefits of dual-targeted drug delivery. In MDA-468 cells, immunoliposomes with higher cetuximab-Fab' per liposome ligand valencies (0-60 ligands/liposome) correlated with higher cell death. Immunoliposomes with varying F5 scFv valencies (0-15 ligands/liposome) had no significant cytotoxicity compared to non-targeted liposomes. In the case of anti-HER2 and anti-EGFR dual-targeted immunoliposomes, cell viability was not significantly lower to anti-EGFR immunoliposomes of similar cetuximab-Fab' valencies ($P<0.6$ for E10Hy; $P<0.99$ for E60Hy). Results were in agreement with the dose-uptake studies, higher uptake resulting in higher toxic effect in cells.

In BT-474 cells, immunoliposomes with varying F5 scFv per liposome valencies (5-15 ligands/liposome) yielded significant cytotoxicity compared to non-targeted liposomes, but no significant difference among each other. Immunoliposomes with varying cetuximab-Fab' valencies (0-60 ligands/liposome) resulted in no significant cell viability. In the case of anti-HER2 and anti-EGFR dual-targeted immunoliposomes, cell growth inhibition was significantly better compared to anti-HER2 immunoliposomes of similar F5 scFv only in two cases where cetuximab was also high: E60H10 ($P<10^{-6}$) and E60H15 ($P<9*10^{-4}$). Compared to the dose-uptake studies, the degree of toxic effect is not as pronounced as targeted uptake.

In MKN-7 cells, immunoliposomes with varying cetuximab-Fab' per liposome ligand valencies (10-60 ligands/liposome) yielded higher cytotoxicity compared to non-targeted liposomes ($P<10^{-4}$), but no significant difference among each other. Immunoliposomes with varying F5 scFv valencies (0-15 ligands/liposome) resulted in no significant cell growth inhibition ($P<1$). In the case of anti-HER2 and anti-EGFR dual-targeted immunoliposomes, cell viability was not significant compared to any mono-targeted immunoliposomes ($0.01<P<1$). Compared to the dose-uptake studies, the degree of toxic effect again is not as pronounced as targeted uptake. In OVCA-420 cells which moderately express both EGFR and HER2, immunoliposomes with varying F5 scFv per liposome (0-15 ligands/liposome) and cetuximab-Fab' per liposome (0-60 ligands/liposome) ligand valencies for mono-targeting had no significant cytotoxicity compared to non-targeted liposomes. However, similar to BT-474 cells, anti-HER2 and anti-EGFR dual-targeted immunoliposomes yielded enhanced cytotoxicity for a few cases cases: E60H10, E60H15, & E10F15; $P<10^{-6}$). Results were in agreement with the dose-uptake studies (data not shown).

For these cytotoxicity studies in vitro, free doxorubicin is the most effective since it easily and quickly penetrate the cell membrane and internalized into the nucleus, the site of action. On the contrary, free doxorubicin is not as effective as liposomal doxorubicin in vivo since free doxorubicin has a fast clearance rate and liposomal doxorubicin are passively targeted to the tumors through the enhanced permeability and retention effect. Cytotoxicity studies in vitro with less membrane diffusible drugs such as topotecan and vinorelbine are more effective in a targeted liposomal formulation compared to free form. Cytotoxicity studies were conducted with doxorubicin as it is the staple drug for liposomal delivery. Changing to more membrane less permeable drugs will likely increase the resolution for the cytotoxicity studies.

In comparison to the cytotoxicity studies with doxorubicin, the targeted uptake studies with anti-HER2 and anti-EGFR immunoliposomes resulted in higher resolution, showing differences between ligand valencies and the additive effects of using dual-targeted immunoliposomes. The additive and possible synergistic effects of using dual-targeting ligands only significantly enhanced the cell growth inhibition with doxorubicin for a few formulations where both anti-EGFR and anti-HER2 ligands were of high valency in the BT-474 and OVA-420 cell lines. As discussed earlier, the uptake of dual-targeted immunoliposomes appears to be additive instead of synergistic where the accumulation is only marginally higher, and hence it is expected that the biological effect of drug delivery was only marginally better if at all. The main advantage was evident in the cocktail-targeting approach, where the immunoliposomes can target multiple receptors, and hence effective with more cell lines. The same dual-targeting liposomal formulations were used with all the cell lines with no observed antagonistic effects with cell viability, even in the case of SK-BR-3 cells (data not shown). Hence, the dozen formulations can be reduced to one.

Conclusion

Anti-HER2, anti-EGFR, and dual-targeted lipid nanoparticles at varying ligand valencies (trastuzumab, F5 scFv, cetuximab, EGF and TGFα) were formulated with receptor-specific targeting against cells lines expressing HER2 and/or EGFR. For HER2-targeting, liposomes were functionalized with Fab' reduced from trastuzumab or F5 scFv. For EGFR-targeting, liposomes were functionalized with Fab' reduced from cetuximab, EGF, or TGFα. Although the surface attachment of F5 scFv, EGF, and TGFα conjugates onto liposomes was effective with the micelle transfer method, Fab' of trastuzumab and cetuximab benefited from the sequential micelle transfer—conjugation method where Fab' is directly conjugated to maleimide micelle transferred onto the liposomes. Through a combination of both the sequential micelle transfer—conjugation and the micelle transfer methods, dual-targeted immunoliposomes of various ligand ratios of anti-HER2 F5 scFv and anti-EGFR cetuximab-Fab' were made possible for further studies.

For HER2-overexpessing and EGFR-overexpressing cell lines, the receptor-mediated cell association studies confirmed the observation where increasing ligand valency per liposome increases targeted uptake until saturation (trastuzumab, F5 scFv, and cetuximab). At the optimum ligand valency and higher valence, there is roughly a 1:1 ratio of ligands (F5 scFv and cetuximab-Fab') to receptor for MCF-7/HER2, BT-474, SK-BR-3, and MDA-468 cells. There was also comparable accumulation of free trastuzumab as trastuzumab-Fab' delivered from immunoliposomes in MCF-7/HER2 and BT-474 cells.

In addition, the accumulation of liposomes and ligands for anti-HER2 and anti-EGFR dual-targeted immunoliposomes were roughly additive of their mono-targeted counterparts in BT-474 and MKN-7 cells. No antagonistic effects were observed from the additional of a non-targeted ligand in all cell lines except for SK-BR-3 at high anti-EGFR ligand valence, where anti-EGFR ligands decreased overall uptake. Despite the additive uptake effect, dual-targeted liposomal delivery of doxorubicin to cell lines expressing HER2 and EGFR only significantly enhanced the cell growth inhibition compared to mono-targeted liposomal delivery for a few liposomal formulations where both anti-EGFR and anti-HER2 ligands were of high valency. Although significant, the improvement was minimal and hence not valuable on a purely increased of cellular drug accumulation standpoint. Dual-targeting lipid nanoparticles can still be beneficial as a system to target heterogeneous cancers.

Materials and Methods

Materials 1,2-distearoyl-sn-glycero-3-phosphocholine (DSPC), 1,2-distearoyl-sn-glycero-3-phosphoethanolamine-N-[methoxy (polyethylene glycol)-2000] (PEG-DSPE), and 1,2-distearoyl-sn-glycero-3-phosphoethanolamine-N-[maleimide (polyethylene glycol)-2000] (Mal-PEG-DSPE) were purchased from Avanti Polar Lipids (Alabaster, Ala.). 1,1'-dioctadecyl-3,3,3',3'-tetramethylindodicarbocyanine perchlorate (DiD) and 3,3'-dioctadecyloxacarbocyanine perchlorate (DiO), and Alexa Fluor 488 carboxylic acid succinimidyl ester mixed isomers were purchased from Life Technologies (Grand Island, N.Y.). Cholesterol was obtained from Calbiochem (San Diego, Calif.).

Trastuzumab/Herceptin® (Roche) and cetuximab/Erbitux® (ImClone LLC) were donated for research purposes. F5 single-chain variable fragment (scFv) conjugated to Mal-PEG-DSPE was manufactured by the National Cancer Institute as previously described(38, 42). EGF and TGFα were purchased from Millipore (Billerica, Mass.) and Peprotech (Rocky Hill, N.J.). Doxorubicin (Dox; Bedford Laboratories) was purchased from the UCSF Pharmacy (San Francisco, Calif.). Pepsin, cysteamine, 2-iminothiolane, glycine, and thiazolyl blue tetrazolium bromide were purchased from Sigma-Aldrich (St. Louis, Mo.). Cell culture media, fetal calf serum, penicillin-streptomycin, trypsin, and phosphate buffered saline (PBS) were purchased from the UCSF Cell Culture Facility (San Francisco, Calif.).

Cell Lines

MDA-468 and BT-474 human breast cancer cell lines were obtained from the American Type Culture Collection (Rockville, Md.), MKN-7 and SK-BR-3 human breast cancer cell lines from the UCSF Cell Culture Facility (San Francisco, Calif.), and MCF-7/HER2(125) human breast cancer cell line from the UCSF Preclinical Therapeutics Core (San Francisco, Calif.). MDA-468 cells were maintained in Leibovitz's L-15 medium without $NaHCO_3$, BT-474 and MKN-7 cells in RPMI-1640 medium, SK-BR-3 in McCoy's 5A medium, and MCF-7/HER2 in DEM H-21 medium with gentamycin (200 μg/ml). All media were supplemented with 10% fetal calf serum and 1% penicillin-streptomycin. All cells were cultured as monolayer at 37° C. in 5% $CO_2$ except in the absence of $CO_2$ for MDA-468 cells.

Liposome Preparation

Liposomes were prepared by the lipid film hydration-extrusion method(117). Lipid solution of DSPC, cholesterol, PEG-DSPE (3:2:0.3), and a fluorescent lipophilic tracer (DiD or DiO, 0.5%) were dissolved in chloroform with a few drops of methanol, and dried under reduced pressure at 60° C. using rotary evaporation. Lipid films were hydrated in HEPES buffered saline (HBS 6.5; 5 mM HEPES, 135 mM NaCl, pH 6.5), and liposomes were prepared according to the repeated freeze-thawing method (6 cycles). Liposomes were subsequently extruded 10 times through 100 nm polycarbonate membrane filters using an extruder, resulting in liposomes of 80-120 nm diameter as determined by dynamic light scattering. Liposome concentration was measured using a standard phosphate assay(118).

For encapsulation of doxorubicin, the remote-loading method using ammonium sulfate was performed(119, 120). Lipid films were hydrated in ammonium sulfate (250 mM, pH 6), followed by the freeze-thawing method and extrusion as described. Free ammonium sulfate was removed by size-exclusion chromatography using a Sephadex G75 column eluted with MES buffered saline (20 mM MES, 135 mM NaCl, pH 5.5). Liposomes were then incubated with doxorubicin (150 μg Dox/μmol PL) at 60° C. for 1 hr. Unencapsulated drugs were removed by size-exclusion chromatography using a Sephadex G75 column eluted with HBS 6.5. Loading efficiencies were typically in the range of 95-100% as determined by fluorometry (485/20:590/35 nm). Final liposomal formulations were all filtered through a 0.2 μm Nalgene® polyethersulfone membrane (Thermo Scientific) before cellular experiments.

Conjugates of Trastuzumab and Cetuximab Fab'

IgG (trastuzumab or cetuximab) was cleaved and reduced to Fab'(35, 36), but incorporated onto liposomes via a modified version of the micelle transfer method(35, 44). IgG was cleaved with pepsin (weight ratio 1:20) in sodium acetate (0.1 M, pH 3.7) at 37° C. for 2 h under argon, followed by dialysis against MES buffered saline (5 mM MES, 135 mM NaCl, pH 6.0). The $Fab_2$ was reduced with cysteamine (16 mM) at 37° C. for 1 h under argon, followed by size-exclusion chromatography on a Sephadex G25 column eluted with MOPS buffered saline (5 mM MOPS, 135 mM NaCl, pH 7.0). For standards, the resulting Fab' was conjugated with a 5:1 excess of Mal-PEG-DSPE at room temperature for 2 hr under argon. The mixture was quenched with 1 mM 2-mercaptoethanol at room temperature for 15 min under argon. Unbound Fab' was removed by size-exclusion chromatography on an AcA34 column eluted with HBS (5 mM HEPES, 135 mM NaCl, pH 7.4) in 1 ml fractions. The fraction of Fab' conjugated to micellar lipids was measured and determined by UV absorbance (280 nm) and SDS-PAGE (Bio-Rad).

Conjugates of EGF and TGFα

EGF and TGFα were thiolated with Traut's reagent(121), conjugated to Mal-PEG-DSPE, and incorporated onto liposomes via the micelle transfer method(35, 44). EGF or TGFα at 0.2-0.5 g/l in Traut's buffer (50 mM triethanolamine, 150 mM NaCl, 1 mM ethylenediaminetetraacetic acid, pH 8) was modified with a 7:1 excess of 2-iminothiolane at room temperature for 1 hr under argon. Excess reagent was removed by size-exclusion chromatography on a Sephadex G25 column eluted with sodium phosphate buffer (0.1 M sodium phosphate, 0.1 M NaCl, pH 7.5) in 200 ul fractions. The thiolated EGF or TGFα was conjugated with a 5:1 excess of Mal-PEG-DSPE at room temperature for 2 hr under argon. The mixture was quenched with 1 mM 2-mercaptoethanol (200 mM stock in 5 mM MES, 135 mM NaCl, pH 6.0) at room temperature for 15 min under argon. Unbound growth factor was removed by size-exclusion chromatography on a Sephadex G75 column eluted with HBS (20 mM Hepes, 150 mM NaCl, pH 7.4) in 200 ul fractions. The fraction of growth factor conjugated to micellar lipids was measured and determined by BCA Protein Assay Kit (Thermo Scientific), Quant-iT Protein Assay Kit (Life Technologies), and SDS-PAGE (Bio-Rad).

Ligand Conjugation onto Liposomes by the Micelle Transfer Method and Sequential Micelle Transfer—Conjugation Method Ligands were incorporated onto liposomes either by the micelle transfer method(35, 44) or the sequential micelle transfer—conjugation method. For the micelle transfer method, conjugates of F5 scFv-PEG-DSPE, EGF-PEG-DSPE or TGFα-PEG-DSPE were incubated with liposomes at 50° C. for 40 min under argon (0-100 ligands per liposome, assuming $8*10^4$ PL per liposome)(35, 122). Unincorporated conjugates were removed by size-exclusion chromatography on a Sepharose 4B column eluted with HBS 6.5. For the sequential micelle transfer—conjugation method, Mal-PEG-DSPE (0-1%) was first incubated with liposomes at 50° C. for 40 min under argon, followed by incubation with freshly reduced Fab' (trastuzumab or cetuximab) at room temperature for 2 hr under argon (1:1 Fab':Mal-PEG-DSPE). Unbound Fab' was removed by size-exclusion chromatography on a Sepharose 4B eluted with HBS 6.5. Conjugate incorporation efficiency was measured and determined by ImageJ (National Institutes of Health) from SDS-PAGE (Bio-Rad) stained with SYPRO Ruby.

Anti-HER2 and Anti-EGFR Dual-Targeted Immunoliposomes

Dual-targeted immunoliposomes of various ligand ratios were achieved by a combination of both the sequential micelle transfer—conjugation and the micelle transfer methods. For anti-HER2 and anti-EGFR dual-targeted immunoliposomes, Mal-PEG-DSPE (0-1%) was first incubated with liposomes at 50° C. for 40 min under argon, followed by incubation with cetuximab-Fab' at room temperature for 2 hr under argon (1:1 Fab':Mal-PEG-DSPE). Unbound Fab' was removed by size-exclusion chromatography on a Sepharose® 4B eluted with HBS 6.5. Subsequently, F5 scFv-PEG-DSPE (0-1%) was incubated with cetuximab-ILS at 50° C. for 40 min under argon. Unincorporated conjugates were again removed by size-exclusion chromatography on a Sepharose® 4B column eluted with HBS 6.5. Alternatively, F5 scFv-PEG-DSPE (0-1%) and Mal-PEG-DSPE (0-1%) can simultaneously be incubated with liposomes at 50° C. for 40 min under argon, followed by incubation with cetuximab-Fab' at room temperature for 2 hr under argon. Conjugate incorporation efficiency was measured and determined by ImageJ (National Institutes of Health) from SDS-PAGE (Bio-Rad) stained with SYPRO Ruby following each conjugation step. F5 scFv conjugation was assumed to be 100% as previously determined.

Fluorescent Ligands

For ligand trafficking experiments, ligands were fluorescently labeled with Alexa Fluor 488 or 546. Trastuzumab, F5 scFv, cetuximab, EGF, and TGFα were conjugated with Alexa Fluor 488 carboxylic acid succinimidyl ester (Life Technologies) as described by vendor, yielding 1-2 fluorophores per ligand. Alexa Fluor 546 carboxylic acid succinimidyl ester (Life Technologies) yielded 3-4 fluorophores per ligand. The relative efficiency of labeling was determined by measurements on the NanoDrop 1000 spectrophotometer and Quant-iT Protein Assay Kit (Life Technologies).

Cell Association Studies

For the assessment of targeted binding by flow cytometry, cells cultured overnight in 24-well plates ($75-100*10^3$ cells/well) were incubated with liposomes labeled with DiD or DiO (0-750 µM PL) at 37° C. for 1-11 hr, washed with PBS 3×, detached with trypsin, resuspended in PBS, and immediately subjected to flow cytometry (BD FACSCalibur). Detached cells were analyzed on fluorescence channels FL4 and FL1 for liposomes labeled with DiD and DiO, respectively. The mean fluorescent intensity with a tight spread of $5*10^3$ cells was recorded per liposomal formulation.

Uptake Studies

For the assessment of targeted uptake by fluorometry, cells cultured overnight in 96-well plates ($80*10^3$ cells/well) were incubated with liposomes labeled with DiD (400 µM PL) at 37° C. for 24 hr, washed with PBS 3×, freeze-thawed 3×, and lysed with 80% isopropyl alcohol (IPA) and 1% Triton X-100. Lysed samples along with standards using labeled liposomes added to the plates were read on a fluorescent microplate reader (Wallac Victor). Measurements were read with excitation and emission band-pass filters as follow: DiD 644:665 nm and doxorubicin 485/20:590/35 nm. Cell count was estimated based on a hemacytometer and MTT assay ((3-(4,5-Dimethylthiazol-2-yl)-2,5-diphenyltetrazolium bromide), showing negligible cell detachment or toxicity under these conditions between groups.

Uptake and Dose-Uptake Studies

For the assessment of targeted uptake by fluorometry, cells cultured overnight in 96-well plates ($50*10^3$ cells/well) were incubated with liposomes labeled with DiD (75 or 375 µM PL) or ligands labeled with Alexa Fluor 488 (40 nM) at 37° C. for 4 hr, stripped with an acid wash (50 mM glycine, 150 mM NaCl, pH 3) at 4° C. for 5 min, washed with PBS 2×, freeze-thawed 3×, and lysed with 80% isopropyl alcohol (IPA) and 1% Triton X-100. For the assessment of targeted dose-uptake by fluorometry, cells cultured overnight in 96-well plates ($50*10^3$ cells/well) were incubated with liposomes labeled with DiD or DiO (800 µM PL with ⅓ dilutions) at 37° C. for 4 hr, washed with PBS 3×, freeze-thawed 3×, and lysed with 80% IPA and 1% Triton X-100. Lysed samples along with standards using labeled liposomes and ligands added to the plates were read on a fluorescent microplate reader (Biotek Synergy HT or Wallac Victor). Measurements were read with excitation and emission band-pass filters as follow: DiO 485/20:528/20 nm, DiD 644:665 nm, Alexa Fluor 488 485/20:528/20 nm, and doxorubicin 485/20:590/35 nm. Cell count was estimated based on a hemacytometer and MTT assay ((3-(4,5-Dimethylthiazol-2-yl)-2,5-diphenyltetrazolium bromide), showing negligible cell detachment or toxicity under these conditions between groups.

Cytotoxicity Studies

For cytotoxicity studies, cells cultured overnight in 96-well plates ($10*10^3$ cells/well) were incubated with doxorubicin-load liposomes (100 µg/ml with ⅓ dilutions) at 37° C. for 4 hr, washed with PBS, and grown in medium for 3 additional days. Cell viability was analyzed by MTT assay. Bars of standard deviations were adjusted for the error of propagation.

Statistical Analysis

For dose-uptake studies, the uptake of liposomes was analyzed by two-way ANOVA via SPSS Statistics 20 (IBM) using two factors, liposomal formulation and incubated liposomal concentration. For cytotoxicity studies, cell growth inhibition was analyzed by two-way ANOVA via SPSS Statistics 20 (IBM) using two factors, liposomal formulation and incubated drug concentration. For group comparisons, the largest P value was selected to generalize the overall group. For mean comparisons, student's t-test was applied.

Abbreviations

The following abbreviations are used herein:
Ab Antibody
ADC Antibody drug conjugate
API Active pharmaceutical ingredient $C_{Beq}$ Cell associated particle concentration at equilibrium (#/cell)

$C_{Beq}(v,f_X,R_T,K_D,K_X)$ $C_{Beq}$ as a function of 5 parameters; Order of function as listed $C_{Beq}(v,fx)$ $C_{Beq}$ as a function of 2 parameters; Order of function as listed $C_{Beq}(v)$ $C_{Beq}$ as a function of 1 parameters; Order of function as listed $C_i$ Concentration of a particle bound to the cell surface via I of its available surface-attached ligands $C_{Lg}$ Ligand/receptor complex DiD 1,1'-Dioctadecyl-3,3,3',3'-tetramethylindodicarbocyanine perchlorate DiO 3,3'-Dioctadecyloxacarbocyanine perchlorate Dox Doxorubicin DSPC 1,2-Distearoyl-sn-glycero-3-phosphocholine DSPE 1,2-Distearoyl-sn-glycero-3-phosphoethanolamine EDTA Ethylenediaminetetraacetic acid EGF Epidermal growth factor EGFR Epidermal growth factor receptor EPR Enhanced permeability and retention effect Eq Equilibrium Equiv. Equivalent ExHy Immunoliposomes with x anti-EGFR ligands and y anti-HER2 ligands per liposome f or fx Effective valence (#/particle)

F5 scFv F5 single-chain variable fragment that binds HER2

Fab' Antigen-binding fragment $Fab_2$ Two antigen-binding fragments connected by disulfide bonds Fc Crystallizable fragment GF Growth factor HBS HEPES-buffered saline HEPES 4-(2-Hydroxyethyl)-1-piperazineethanesulfonic acid HER1 Human epidermal growth factor receptor 1

HER2 Human epidermal growth factor receptor 2

HER3 Human epidermal growth factor receptor 3

HER4 Human epidermal growth factor receptor 4

HHa Dual-targeted against cells with dual High/High; Additive binding

HHs Dual-targeted against cells with dual High/High; Synergetic binding

High or H High receptor expression ($R_T$=~10^6)

HMa Dual-targeted against cells with dual High/Moderate; Additive binding

HMs Dual-targeted against cells with dual High/Moderate; Synergetic binding i Number of bounds IC50 Half maximal inhibitory concentration IgG Immunoglobulin G ILS Immunoliposome $K_D$ Equilibrium dissociation constant (nM)

$k_d$ Dissociation rate constant $k_f$ Associating rate constant $K_X$ Crosslinking equilibrium constant (1/(#/cell))

$k_x$ Receptor crosslinking rate constant $k_{-x}$ Receptor decrosslinking rate constant L Particle concentration in solution per cell (#/cell)

LDC Ligand drug conjugate $L_o$ Particle concentration in solution per cell (~1M #/cell); initial Lg Ligand Low Low receptor expression ($R_T$=~10^4)

LS Liposome mAb Monoclonal antibody

Mal Maleimide

Mal-PEG-DSPE 1,2-Distearoyl-sn-glycero-3-phosphoethanolamine-N-[maleimide(polyethylene glycol)-2000]

MES 2-(N-Morpholino)ethanesulfonic acid

MFI Mean fluorescent intensity

MMa Dual-targeted against cells with dual Moderate/Moderate; Additive binding

MMs Dual-targeted against cells with dual Moderate/Moderate; Synergetic binding

Moderate or M Moderate receptor expression ($R_T$=~10^5)

MOPS 3-(N-Morpholino)propanesulfonic acid

MTT (3-(4,5-Dimethylthiazol-2-yl)-2,5-diphenyltetrazolium bromide

NA Avogadro's number

NaCl Sodium chloride

NE Not evaluable

NT Non-targeted (liposome)

PBS Phosphate-buffered saline

PEG Polyethylene glycol

PEG-DSPE 1,2-Distearoyl-sn-glycero-3-phosphoethanolamine-N-[methoxy(polyethylene glycol)-2000]

PL Phospholipid

Q Pertaining to receptor or nanoparticle

R Receptor concentration $R_{eq}$ or $R_{eqF}$ Free receptors per cell at equilibrium (#/cell)

$R_{eqF}(v,fx,R_T,K_D,K_X)$ Free as a function of 5 parameters; Order of function as listed $R_{eq}(v,fx)$ $R_{eqF}$ as a function of 2 parameters; Order of function as listed $R_{eq}(v)$ $R_{eqF}$ as a function of 1 parameters; Order of function as listed RES Reticuloendothelial system RhuMAb Recombinant humanized monoclonal antibody RT Room temperature $R_T$ Total receptors per cell (#/cell)

scFv Single-chain variable fragment

SDS-PAGE Sodium dodecyl sulfate polyacrylamide gel electrophoresis

SE Standard error

SH Sulfhydryl group

TEA Triethanolamine

TGFα Transforming growth factor receptor alpha

TNFα Tumor necrosis factor alpha

Tras Trastuzumab

UCSF University of California San Francisco

UV Ultraviolet

VEGF Vascular endothelial growth factor

VEGFR Vascular endothelial growth factor receptor v Ligand valence per particle (#/particle)

REFERENCE LIST

The references below are cited by number in the text of the Examples above:

1. D. C. Drummond, O. Meyer, K. Hong, D. B. Kirpotin, D. Papahadjopoulos, Optimizing liposomes for delivery of chemotherapeutic agents to solid tumors. *Pharmacological reviews* 51, 691 (December 1999).

2. D. Papahadjopoulos, A. Gabizon, *Sterically stabilized (Stealth®) liposomes: Pharmacological properties and drug carrying potential in cancer*. J. R. Philippot, F. Schuber, Eds., Liposomes as Tools in Basic Research and Industry (CRC Press, Boca Raton, Fla., 1995), pp. 177-188.

3. P. A. Speth, Q. G. van Hoesel, C. Haanen, Clinical pharmacokinetics of doxorubicin. *Clinical pharmacokinetics* 15, 15 (July 1988).

4. C. O. Noble, D. B. Kirpotin, M. E. Hayes, C. Mamot, K. Hong, J. W. Park, C. C. Benz, J. D. Marks, D. C. Drummond, Development of ligand-targeted liposomes for cancer therapy. *Expert opinion on therapeutic targets* 8, 335 (August 2004).

5. T. M. Allen, L. Murray, S. MacKeigan, M. Shah, Chronic liposome administration in mice: effects on reticuloendothelial function and tissue distribution. *The Journal of pharmacology and experimental therapeutics* 229, 267 (April 1984).

6. G. Storm, C. Oussoren, P. J. Peters, Y. Barenholz, *Tolerability of liposomes in vivo*. G. Gregoriadis, Ed., Liposome Technology (CRC Press, Inc., Boca Raton, Fla., 1993).

7. C. P. Carpenter, M. D. Woodside, E. R. Kinkead, J. M. King, L. J. Sullivan, Response of dogs to repeated intravenous injection of polyethylene glycol 4000 with notes on excretion and sensitization. *Toxicology and applied pharmacology* 18, 35 (January 1971).

8. T. M. Allen, C. Hansen, J. Rutledge, Liposomes with prolonged circulation times: factors affecting uptake by reticuloendothelial and other tissues. *Biochimica et biophysica acta* 981, 27 (May 19, 1989).

9. D. Liu, A. Mori, L. Huang, Role of liposome size and RES blockade in controlling biodistribution and tumor uptake of GM1-containing liposomes. *Biochimica et biophysica acta* 1104, 95 (Feb. 17, 1992).

10. M. C. Woodle, K. K. Matthay, M. S. Newman, J. E. Hidayat, L. R. Collins, C. Redemann, F. J. Martin, D. Papahadjopoulos, Versatility in lipid compositions showing prolonged circulation with sterically stabilized liposomes. *Biochimica et biophysica acta* 1105, 193 (Apr. 13, 1992).

11. T. Allen, C. Hansen, D. E. Lopes de Menezes, Pharmacokinetics of long-circulating liposomes. *Advanced drug delivery reviews* 16, 267 (September 1995).

12. T. M. Allen, Long-circulating (sterically stabilized) liposomes for targeted drug delivery. *Trends in pharmacological sciences* 15, 215 (July 1994).

13. T. M. Allen, C. Hansen, Pharmacokinetics of stealth versus conventional liposomes: effect of dose. *Biochimica et biophysica acta* 1068, 133 (Sep. 30, 1991).

14. M. S. Webb, D. Saxon, F. M. Wong, H. J. Lim, Z. Wang, M. B. Bally, L. S. Choi, P. R. Cullis, L. D. Mayer, Comparison of different hydrophobic anchors conjugated to poly(ethylene glycol): effects on the pharmacokinetics of liposomal vincristine. *Biochimica et biophysica acta* 1372, 272 (Jul. 17, 1998).

15. M. S. Webb, T. O. Harasym, D. Masin, M. B. Bally, L. D. Mayer, Sphingomyelin-cholesterol liposomes significantly enhance the pharmacokinetic and therapeutic properties of vincristine in murine and human tumour models. *British journal of cancer* 72, 896 (October 1995).

16. A. Gabizon, D. Papahadjopoulos, The role of surface charge and hydrophilic groups on liposome clearance in vivo. *Biochimica et biophysica acta* 1103, 94 (Jan. 10, 1992).

17. J. Senior, J. C. Crawley, G. Gregoriadis, Tissue distribution of liposomes exhibiting long half-lives in the circulation after intravenous injection. *Biochimica et biophysica acta* 839, 1 (Mar. 29, 1985).

18. J. H. Senior, Fate and behavior of liposomes in vivo: a review of controlling factors. *Critical reviews in therapeutic drug carrier systems* 3, 123 (1987).

19. F. M. Muggia, J. D. Hainsworth, S. Jeffers, P. Miller, S. Groshen, M. Tan, L. Roman, B. Uziely, L. Muderspach, A. Garcia, A. Burnett, F. A. Greco, C. P. Morrow, L. J. Paradiso, L. J. Liang, Phase II study of liposomal doxorubicin in refractory ovarian cancer: antitumor activity and toxicity modification by liposomal encapsulation. *Journal of clinical oncology: official journal of the American Society of Clinical Oncology* 15, 987 (March 1997).

20. O. Lyass, B. Uziely, R. Ben-Yosef, D. Tzemach, N. I. Heshing, M. Lotem, G. Brufman, A. Gabizon, Correlation of toxicity with pharmacokinetics of pegylated liposomal doxorubicin (Doxil) in metastatic breast carcinoma. *Cancer* 89, 1037 (Sep. 1, 2000).

21. F. Yuan, M. Dellian, D. Fukumura, M. Leunig, D. A. Berk, V. P. Torchilin, R. K. Jain, Vascular permeability in a human tumor xenograft: molecular size dependence and cutoff size. *Cancer research* 55, 3752 (Sep. 1, 1995).

22. S. K. Hobbs, W. L. Monsky, F. Yuan, W. G. Roberts, L. Griffith, V. P. Torchilin, R. K. Jain, Regulation of transport pathways in tumor vessels: role of tumor type and microenvironment. *Proceedings of the National Academy of Sciences of the United States of America* 95, 4607 (Apr. 14, 1998).

23. Y. Matsumura, H. Maeda, A new concept for macromolecular therapeutics in cancer chemotherapy: mechanism of tumoritropic accumulation of proteins and the antitumor agent smancs. *Cancer research* 46, 6387 (December 1986).

24. H. Maeda, J. Wu, T. Sawa, Y. Matsumura, K. Hori, Tumor vascular permeability and the EPR effect in macromolecular therapeutics: a review. *Journal of controlled release: official journal of the Controlled Release Society* 65, 271 (Mar. 1, 2000).

25. S. K. Huang, K. D. Lee, K. Hong, D. S. Friend, D. Papahadjopoulos, Microscopic localization of sterically stabilized liposomes in colon carcinoma-bearing mice. *Cancer research* 52, 5135 (Oct. 1, 1992).

26. V. P. Torchilin, Passive and active drug targeting: drug delivery to tumors as an example. *Handbook of experimental pharmacology*, 3 (2010).

27. A. Gabizon, M. Chemla, D. Tzemach, A. T. Horowitz, D. Goren, Liposome longevity and stability in circulation: effects on the in vivo delivery to tumors and therapeutic efficacy of encapsulated anthracyclines. *Journal of drug targeting* 3, 391 (1996).

28. L. D. Mayer, P. Cullis, M. Bally, *Medical Applications of Liposomes*. D. Lasic, D. Papahadjopoulos, Eds., (Elsevier Science, B.V., New York, 1998).

29. P. Sapra, T. M. Allen, Ligand-targeted liposomal anticancer drugs. *Progress in lipid research* 42, 439 (September 2003).

30. T. M. Allen, Ligand-targeted therapeutics in anticancer therapy. *Nature reviews. Cancer* 2, 750 (October 2002).

31. G. A. Niehans, T. P. Singleton, D. Dykoski, D. T. Kiang, Stability of HER-2/neu expression over time and at multiple metastatic sites. *Journal of the National Cancer Institute* 85, 1230 (Aug. 4, 1993).

32. D. S. Salomon, R. Brandt, F. Ciardiello, N. Normanno, Epidermal growth factor-related peptides and their receptors in human malignancies. *Critical reviews in oncology/hematology* 19, 183 (July 1995).

33. S. Zalipsky, B. Puntambekar, P. Boulikas, C. M. Engbers, M. C. Woodle, Peptide attachment to extremities of liposomal surface grafted PEG chains: preparation of the long-circulating form of laminin pentapeptide, YIGSR. *Bioconjugate chemistry* 6, 705 (November-December 1995).

34. U. B. Nielsen, D. B. Kirpotin, E. M. Pickering, K. Hong, J. W. Park, M. Refaat Shalaby, Y. Shao, C. C. Benz, J. D. Marks, Therapeutic efficacy of anti-ErbB2 immunoliposomes targeted by a phage antibody selected for cellular endocytosis. *Biochimica et biophysica acta* 1591, 109 (Aug. 19, 2002).
35. D. Kirpotin, J. W. Park, K. Hong, S. Zalipsky, W. L. Li, P. Carter, C. C. Benz, D. Papahadjopoulos, Sterically stabilized anti-HER2 immunoliposomes: design and targeting to human breast cancer cells in vitro. *Biochemistry* 36, 66 (Jan. 7, 1997).
36. C. Mamot, D. C. Drummond, U. Greiser, K. Hong, D. B. Kirpotin, J. D. Marks, J. W. Park, Epidermal growth factor receptor (EGFR)-targeted immunoliposomes mediate specific and efficient drug delivery to EGFR- and EGFRvIII-overexpressing tumor cells. *Cancer research* 63, 3154 (Jun. 15, 2003).
37. K. Maruyama, T. Takizawa, T. Yuda, S. J. Kennel, L. Huang, M. Iwatsuru, Targetability of novel immunoliposomes modified with amphipathic poly(ethylene glycol)s conjugated at their distal terminals to monoclonal antibodies. *Biochimica et biophysica acta* 1234, 74 (Mar. 8, 1995).
38. M. A. Poul, B. Becerril, U. B. Nielsen, P. Morisson, J. D. Marks, Selection of tumor-specific internalizing human antibodies from phage libraries. *Journal of molecular biology* 301, 1149 (Sep. 1, 2000).
39. B. Becerril, M. A. Poul, J. D. Marks, Toward selection of internalizing antibodies from phage libraries. *Biochemical and biophysical research communications* 255, 386 (Feb. 16, 1999).
40. M. D. Sheets, P. Amersdorfer, R. Finnern, P. Sargent, E. Lindquist, R. Schier, G. Hemingsen, C. Wong, J. C. Gerhart, J. D. Marks, Efficient construction of a large nonimmune phage antibody library: the production of high-affinity human single-chain antibodies to protein antigens. *Proceedings of the National Academy of Sciences of the United States of America* 95, 6157 (May 26, 1998).
41. E. T. Boder, K. S. Midelfort, K. D. Wittrup, Directed evolution of antibody fragments with monovalent femtomolar antigen-binding affinity. *Proceedings of the National Academy of Sciences of the United States of America* 97, 10701 (Sep. 26, 2000).
42. U. B. Nielsen, J. D. Marks, Internalizing antibodies and targeted cancer therapy: direct selection from phage display libraries. *Pharmaceutical science & technology today* 3, 282 (August 2000).
43. D. Goren, A. T. Horowitz, S. Zalipsky, M. C. Woodle, Y. Yarden, A. Gabizon, Targeting of stealth liposomes to erbB-2 (Her/2) receptor: in vitro and in vivo studies. *British journal of cancer* 74, 1749 (December 1996).
44. J. W. Park, K. Hong, D. B. Kirpotin, G. Colbern, R. Shalaby, J. Baselga, Y. Shao, U. B. Nielsen, J. D. Marks, D. Moore, D. Papahadjopoulos, C. C. Benz, Anti-HER2 immunoliposomes: enhanced efficacy attributable to targeted delivery. *Clinical cancer research: an official journal of the American Association for Cancer Research* 8, 1172 (April 2002).
45. D. Aragnol, L. D. Leserman, Immune clearance of liposomes inhibited by an anti-Fc receptor antibody in vivo. *Proceedings of the National Academy of Sciences of the United States of America* 83, 2699 (April 1986).
46. J. A. Harding, C. M. Engbers, M. S. Newman, N. I. Goldstein, S. Zalipsky, Immunogenicity and pharmacokinetic attributes of poly(ethylene glycol)-grafted immunoliposomes. *Biochimica et biophysica acta* 1327, 181 (Jul. 25, 1997).
47. S. Zalipsky, Functionalized poly(ethylene glycol) for preparation of biologically relevant conjugates. *Bioconjugate chemistry* 6, 150 (March-April 1995).
48. T. Ishida, D. L. Iden, T. M. Allen, A combinatorial approach to producing sterically stabilized (Stealth) immunoliposomal drugs. *FEBS letters* 460, 129 (Oct. 22, 1999).
49. D. L. Iden, T. M. Allen, In vitro and in vivo comparison of immunoliposomes made by conventional coupling techniques with those made by a new post-insertion approach. *Biochimica et biophysica acta* 1513, 207 (Aug. 6, 2001).
50. D. Kirpotin, J. W. Park, K. Hong, Y. Shao, R. Shalaby, G. Colbern, C. C. Benz, D. Papahadjopoulos, Targeting of Liposomes to Solid Tumors: The Case of Sterically Stabilized Anti-Her2 Immunoliposomes. *Journal of liposome research* 7, 391 (1997).
51. C. Mamot, D. C. Drummond, C. O. Noble, V. Kallab, Z. Guo, K. Hong, D. B. Kirpotin, J. W. Park, Epidermal growth factor receptor-targeted immunoliposomes significantly enhance the efficacy of multiple anticancer drugs in vivo. *Cancer research* 65, 11631 (Dec. 15, 2005).
52. J. W. Park, K. Hong, D. B. Kirpotin, O. Meyer, D. Papahadjopoulos, C. C. Benz, Anti-HER2 immunoliposomes for targeted therapy of human tumors. *Cancer letters* 118, 153 (Oct. 14, 1997).
53. J. N. Moreira, R. Gaspar, T. M. Allen, Targeting Stealth liposomes in a murine model of human small cell lung cancer. *Biochimica et biophysica acta* 1515, 167 (Dec. 1, 2001).
54. C. Mamot, D. C. Drummond, K. Hong, D. B. Kirpotin, J. W. Park, Liposome-based approaches to overcome anticancer drug resistance. *Drug resistance updates reviews and commentaries in antimicrobial and anticancer chemotherapy* 6, 271 (October 2003).
55. D. Sadava, A. Coleman, S. E. Kane, Liposomal daunorubicin overcomes drug resistance in human breast, ovarian and lung carcinoma cells. *Journal of liposome research* 12, 301 (November 2002).
56. C. Mamot, R. Ritschard, A. Wicki, W. Kung, J. Schuller, R. Herrmann, C. Rochlitz, Immunoliposomal delivery of doxorubicin can overcome multidrug resistance mechanisms in EGFR-overexpressing tumor cells. *Journal of drug targeting* 20, 422 (June 2012).
57. I. Mellman, Endocytosis and molecular sorting. *Annual review of cell and developmental biology* 12, 575 (1996).
58. A. Sorkin, M. von Zastrow, Endocytosis and signalling: intertwining molecular networks. *Nature reviews. Molecular cell biology* 10, 609 (September 2009).
59. S. L. Schmid, Clathrin-coated vesicle formation and protein sorting: an integrated process. *Annual review of biochemistry* 66, 511 (1997).
60. Q. Al-Awqati, Proton-translocating ATPases. *Annual review of cell biology* 2, 179 (1986).
61. I. Mellman, R. Fuchs, A. Helenius, Acidification of the endocytic and exocytic pathways. *Annual review of biochemistry* 55, 663 (1986).
62. M. Forgac, Structure and properties of the coated vesicle proton pump. *Annals of the New York Academy of Sciences* 671, 273 (Nov. 30, 1992).
63. A. Alexander, Endocytosis and intracellular sorting of receptor tyrosine kinases. *Frontiers in bioscience: a journal and virtual library* 3, d729 (Jul. 26, 1998).
64. A. Spang, Vesicle transport: a close collaboration of Rabs and effectors. *Current biology: CB* 14, R33 (Jan. 6, 2004).

65. M. Zerial, H. McBride, Rab proteins as membrane organizers. *Nature reviews. Molecular cell biology* 2, 107 (February 2001).
66. C. Bucci, P. Thomsen, P. Nicoziani, J. McCarthy, B. van Deurs, Rab7: a key to lysosome biogenesis. *Molecular biology of the cell* 11, 467 (February 2000).
67. M. Ren, G. Xu, J. Zeng, C. De Lemos-Chiarandini, M. Adesnik, D. D. Sabatini, Hydrolysis of GTP on rab 11 is required for the direct delivery of transferrin from the pericentriolar recycling compartment to the cell surface but not from sorting endosomes. *Proceedings of the National Academy of Sciences of the United States of America* 95, 6187 (May 26, 1998).
68. M. Trischler, W. Stoorvogel, O. Ullrich, Biochemical analysis of distinct Rab5- and Rab11-positive endosomes along the transferrin pathway. *Journal of cell science* 112 (Pt 24), 4773 (December 1999).
69. D. Duan, Y. Yue, Z. Yan, P. B. McCray, Jr., J. F. Engelhardt, Polarity influences the efficiency of recombinant adeno associated virus infection in differentiated airway epithelia. *Human gene therapy* 9, 2761 (Dec. 10, 1998).
70. C. R. Hopkins, I. S. Trowbridge, Internalization and processing of transferrin and the transferrin receptor in human carcinoma A431 cells. *The Journal of cell biology* 97, 508 (August 1983).
71. C. R. Hopkins, Intracellular routing of transferrin and transferrin receptors in epidermoid carcinoma A431 cells. *Cell* 35, 321 (November 1983).
72. M. Karin, B. Mintz, Receptor-mediated endocytosis of transferrin in developmentally totipotent mouse teratocarcinoma stem cells. *The Journal of biological chemistry* 256, 3245 (Apr. 10, 1981).
73. J. N. Octave, Y. J. Schneider, R. R. Crichton, A. Trouet, Transferrin uptake by cultured rat embryo fibroblasts. The influence of temperature and incubation time, subcellular distribution and short-term kinetic studies. *European journal of biochemistry/FEBS* 115, 611 (April 1981).
74. J. D. Bleil, M. S. Bretscher, Transferrin receptor and its recycling in HeLa cells. *The EMBO journal* 1, 351 (1982).
75. C. Harding, J. Heuser, P. Stahl, Receptor-mediated endocytosis of transferrin and recycling of the transferrin receptor in rat reticulocytes. *The Journal of cell biology* 97, 329 (August 1983).
76. A. R. French, G. P. Sudlow, H. S. Wiley, D. A. Laufenburger, Postendocytic trafficking of epidermal growth factor-receptor complexes is mediated through saturable and specific endosomal interactions. *The Journal of biological chemistry* 269, 15749 (Jun. 3, 1994).
77. R. Ebner, R. Derynck, Epidermal growth factor and transforming growth factor-alpha: differential intracellular routing and processing of ligand-receptor complexes. *Cell regulation* 2, 599 (August 1991).
78. M. Perez-Tones, M. Guix, A. Gonzalez, C. L. Arteaga, Epidermal growth factor receptor (EGFR) antibody down-regulates mutant receptors and inhibits tumors expressing EGFR mutations. *The Journal of biological chemistry* 281, 40183 (Dec. 29, 2006).
79. C. D. Austin, A. M. De Maziere, P. I. Pisacane, S. M. van Dijk, C. Eigenbrot, M. X. Sliwkowski, J. Klumperman, R. H. Scheller, Endocytosis and sorting of ErbB2 and the site of action of cancer therapeutics trastuzumab and geldanamycin. *Molecular biology of the cell* 15, 5268 (December 2004).
80. T. Yoshida, I. Okamoto, T. Okabe, T. Iwasa, T. Satoh, K. Nishio, M. Fukuoka, K. Nakagawa, Matuzumab and cetuximab activate the epidermal growth factor receptor but fail to trigger downstream signaling by Akt or Erk. *International journal of cancer. Journal international du cancer* 122, 1530 (Apr. 1, 2008).
81. D. Patel, A. Lahiji, S. Patel, M. Franklin, X. Jimenez, D. J. Hicklin, X. Kang, Monoclonal antibody cetuximab binds to and down-regulates constitutively activated epidermal growth factor receptor vIII on the cell surface. *Anticancer research* 27, 3355 (September-October 2007).
82. W. S. Chen, C. S. Lazar, M. Poenie, R. Y. Tsien, G. N. Gill, M. G. Rosenfeld, Requirement for intrinsic protein tyrosine kinase in the immediate and late actions of the EGF receptor. *Nature* 328, 820 (Aug. 27-Sep. 2, 1987).
83. E. Kornilova, T. Sorkina, L. Beguinot, A. Sorkin, Lysosomal targeting of epidermal growth factor receptors via a kinase-dependent pathway is mediated by the receptor carboxyl-terminal residues 1022-1123. *The Journal of biological chemistry* 271, 30340 (Nov. 29, 1996).
84. S. J. Kil, M. Hobert, C. Carlin, A leucine-based determinant in the epidermal growth factor receptor juxtamembrane domain is required for the efficient transport of ligand-receptor complexes to lysosomes. *The Journal of biological chemistry* 274, 3141 (Jan. 29, 1999).
85. S. J. Kil, C. Carlin, EGF receptor residues leu(679), leu(680) mediate selective sorting of ligand-receptor complexes in early endosomal compartments. *Journal of cellular physiology* 185, 47 (October 2000).
86. J. Bao, I. Alroy, H. Waterman, E. D. Schejter, C. Brodie, J. Gruenberg, Y. Yarden, Threonine phosphorylation diverts internalized epidermal growth factor receptors from a degradative pathway to the recycling endosome. *The Journal of biological chemistry* 275, 26178 (Aug. 25, 2000).
87. K. A. Lund, C. S. Lazar, W. S. Chen, B. J. Walsh, J. B. Welsh, J. J. Herbst, G. M. Walton, M. G. Rosenfeld, G. N. Gill, H. S. Wiley, Phosphorylation of the epidermal growth factor receptor at threonine 654 inhibits ligand-induced internalization and down-regulation. *The Journal of biological chemistry* 265, 20517 (Nov. 25, 1990).
88. L. K. Opresko, C. P. Chang, B. H. Will, P. M. Burke, G. N. Gill, H. S. Wiley, Endocytosis and lysosomal targeting of epidermal growth factor receptors are mediated by distinct sequences independent of the tyrosine kinase domain. *The Journal of biological chemistry* 270, 4325 (Mar. 3, 1995).
89. W. Ding, L. N. Zhang, C. Yeaman, J. F. Engelhardt, rAAV2 traffics through both the late and the recycling endosomes in a dose-dependent fashion. *Molecular therapy: the journal of the American Society of Gene Therapy* 13, 671 (April 2006).
90. R. J. Lee, P. S. Low, Delivery of liposomes into cultured KB cells via folate receptor-mediated endocytosis. *The Journal of biological chemistry* 269, 3198 (Feb. 4, 1994).
91. A. Gabizon, A. T. Horowitz, D. Goren, D. Tzemach, F. Mandelbaum-Shavit, M. M. Qazen, S. Zalipsky, Targeting folate receptor with folate linked to extremities of poly (ethylene glycol)-grafted liposomes: in vitro studies. *Bioconjugate chemistry* 10, 289 (March-April 1999).
92. G. Blume, G. Cevc, M. D. Crommelin, I. A. Bakker-Woudenberg, C. Kluft, G. Storm, Specific targeting with poly(ethylene glycol)-modified liposomes: coupling of homing devices to the ends of the polymeric chains combines effective target binding with long circulation times. *Biochimica et biophysica acta* 1149, 180 (Jun. 18, 1993).
93. Y. Zhou, D. C. Drummond, H. Zou, M. E. Hayes, G. P. Adams, D. B. Kirpotin, J. D. Marks, Impact of single-chain Fv antibody fragment affinity on nanoparticle targeting of epidermal growth factor receptor-expressing tumor cells. *Journal of molecular biology* 371, 934 (Aug. 24, 2007).

94. J. W. Park, K. Hong, P. Carter, H. Asgari, L. Y. Guo, G. A. Keller, C. Wirth, R. Shalaby, C. Kotts, W. I. Wood, et al., Development of anti-p185HER2 immunoliposomes for cancer therapy. *Proceedings of the National Academy of Sciences of the United States of America* 92, 1327 (Feb. 28, 1995).

95. D. Ye, J. Mendelsohn, Z. Fan, Augmentation of a humanized anti-HER2 mAb 4D5 induced growth inhibition by a human-mouse chimeric anti-EGF receptor mAb C225. *Oncogene* 18, 731 (Jan. 21, 1999).

96. K. Laginha, D. Mumbengegwi, T. Allen, Liposomes targeted via two different antibodies: assay, B-cell binding and cytotoxicity. *Biochimica et biophysica acta* 1711, 25 (Jun. 1, 2005).

97. S. Grant, L. Qiao, P. Dent, Roles of ERBB family receptor tyrosine kinases, and downstream signaling pathways, in the control of cell growth and survival. *Frontiers in bioscience: a journal and virtual library* 7, d376 (Feb. 1, 2002).

98. S. A. Eccles, The epidermal growth factor receptor/ErbB/HER family in normal and malignant breast biology. *The International journal of developmental biology* 55, 685 (2011).

99. E. M. Bublil, Y. Yarden, The EGF receptor family: spearheading a merger of signaling and therapeutics. *Current opinion in cell biology* 19, 124 (April 2007).

100. R. I. Nicholson, J. M. Gee, M. E. Harper, EGFR and cancer prognosis. *Eur J Cancer* 37 Suppl 4, S9 (September 2001).

101. J. J. Laskin, A. B. Sandler, Epidermal growth factor receptor: a promising target in solid tumours. *Cancer treatment reviews* 30, 1 (February 2004).

102. T. Heitner, A. Moor, J. L. Garrison, C. Marks, T. Hasan, J. D. Marks, Selection of cell binding and internalizing epidermal growth factor receptor antibodies from a phage display library. *Journal of immunological methods* 248, 17 (Feb. 1, 2001).

103. S. Paik, C. Park, HER-2 and choice of adjuvant chemotherapy in breast cancer. *Seminars in oncology* 28, 332 (August 2001).

104. N. Prenzel, O. M. Fischer, S. Streit, S. Hart, A. Ullrich, The epidermal growth factor receptor family as a central element for cellular signal transduction and diversification. *Endocrine-related cancer* 8, 11 (March 2001).

105. D. J. Slamon, G. M. Clark, S. G. Wong, W. J. Levin, A. Ullrich, W. L. McGuire, Human breast cancer: correlation of relapse and survival with amplification of the HER-2/neu oncogene. *Science* 235, 177 (Jan. 9, 1987).

106. D. J. Slamon, W. Godolphin, L. A. Jones, J. A. Holt, S. G. Wong, D. E. Keith, W. J. Levin, S. G. Stuart, J. Udove, A. Ullrich, et al., Studies of the HER-2/neu proto-oncogene in human breast and ovarian cancer. *Science* 244, 707 (May 12, 1989).

107. A. D. Santin, S. Bellone, J. J. Roman, J. K. McKenney, S. Pecorelli, Trastuzumab treatment in patients with advanced or recurrent endometrial carcinoma overexpressing HER2/neu. *International journal of gynaecology and obstetrics: the official organ of the International Federation of Gynaecology and Obstetrics* 102, 128 (August 2008).

108. J. Baselga, D. Tripathy, J. Mendelsohn, S. Baughman, C. C. Benz, L. Dantis, N. T. Sklarin, A. D. Seidman, C. A. Hudis, J. Moore, P. P. Rosen, T. Twaddell, I. C. Henderson, L. Norton, Phase II study of weekly intravenous recombinant humanized anti-p185HER2 monoclonal antibody in patients with HER2/neu-overexpressing metastatic breast cancer. *Journal of clinical oncology: official journal of the American Society of Clinical Oncology* 14, 737 (March 1996).

109. M. A. Cobleigh, C. L. Vogel, D. Tripathy, N. J. Robert, S. Scholl, L. Fehrenbacher, J. M. Wolter, V. Paton, S. Shak, G. Lieberman, D. J. Slamon, Multinational study of the efficacy and safety of humanized anti-HER2 monoclonal antibody in women who have HER2-overexpressing metastatic breast cancer that has progressed after chemotherapy for metastatic disease. *Journal of clinical oncology: official journal of the American Society of Clinical Oncology* 17, 2639 (September 1999).

110. D. J. Slamon, B. Leyland-Jones, S. Shak, H. Fuchs, V. Paton, A. Bajamonde, T. Fleming, W. Eiermann, J. Wolter, M. Pegram, J. Baselga, L. Norton, Use of chemotherapy plus a monoclonal antibody against HER2 for metastatic breast cancer that overexpresses HER2. *The New England journal of medicine* 344, 783 (Mar. 15, 2001).

111. R. M. Neve, U. B. Nielsen, D. B. Kirpotin, M. A. Poul, J. D. Marks, C. C. Benz, Biological effects of anti-ErbB2 single chain antibodies selected for internalizing function. *Biochemical and biophysical research communications* 280, 274 (Jan. 12, 2001).

112. M. Sznol, J. Holmlund, Antigen-specific agents in development. *Seminars in oncology* 24, 173 (April 1997).

113. P. Carter, M. L. Rodriguez, J. W. Park, G. Zapata, *Preparation and uses of Fab' fragments from E. coli*. J. G. McCaffrey, H. R. Hoogenboom, D. J. Chiswell, Eds., Antibody Engineering: A Practical Approach (IRL Press, Oxford, 1996).

114. R. Schier, J. D. Marks, E. J. Wolf, G. Apell, C. Wong, J. E. McCartney, M. A. Bookman, J. S. Huston, L. L. Houston, L. M. Weiner, et al., In vitro and in vivo characterization of a human anti-c-erbB-2 single-chain Fv isolated from a filamentous phage antibody library. *Immunotechnology: an international journal of immunological engineering* 1, 73 (May 1995).

115. A. E. Lenferink, A. D. De Roos, M. J. Van Vugt, M. L. Van de Poll, E. J. Van Zoelen, The linear C-terminal regions of epidermal growth factor (EGF) and transforming growth factor-alpha bind to different epitopes on the human EGF receptor. *The Biochemical journal* 336 (Pt 1), 147 (Nov. 15, 1998).

116. N. I. Goldstein, M. Prewett, K. Zuklys, P. Rockwell, J. Mendelsohn, Biological efficacy of a chimeric antibody to the epidermal growth factor receptor in a human tumor xenograft model. *Clinical cancer research: an official journal of the American Association for Cancer Research* 1, 1311 (November 1995).

117. F. Szoka, Jr., D. Papahadjopoulos, Comparative properties and methods of preparation of lipid vesicles (liposomes). *Annual review of biophysics and bioengineering* 9, 467 (1980).

118. G. R. Bartlett, Phosphorus assay in column chromatography. *The Journal of biological chemistry* 234, 466 (March 1959).

119. D. D. Lasic, P. M. Frederik, M. C. Stuart, Y. Barenholz, T. J. McIntosh, Gelation of liposome interior. A novel method for drug encapsulation. *FEBS letters* 312, 255 (Nov. 9, 1992).

120. G. Haran, R. Cohen, L. K. Bar, Y. Barenholz, Transmembrane ammonium sulfate gradients in liposomes produce efficient and stable entrapment of amphipathic weak bases. *Biochimica et biophysica acta* 1151, 201 (Sep. 19, 1993).

121. E. Bohl Kullberg, N. Bergstrand, J. Carlsson, K. Edwards, M. Johnsson, S. Sjoberg, L. Gedda, Development of EGF-conjugated liposomes for targeted delivery of boronated DNA-binding agents. *Bioconjugate chemistry* 13, 737 (July-August 2002).

122. D. A. Marsh, CRC Handbook of Lipid Bilayers. *CRC Press, Boca Raton, Fla.,* 163 (1990).

123. K. Subik, J. F. Lee, L. Baxter, T. Strzepek, D. Costello, P. Crowley, L. Xing, M. C. Hung, T. Bonfiglio, D. G. Hicks, P. Tang, The Expression Patterns of ER, PR, HER2, CK5/6, EGFR, Ki-67 and AR by Immunohistochemical Analysis in Breast Cancer Cell Lines. *Breast cancer: basic and clinical research* 4, 35 (2010).

124. G. D. Lewis, I. Figari, B. Fendly, W. L. Wong, P. Carter, C. Gorman, H. M. Shepard, Differential responses of human tumor cell lines to anti-p185HER2 monoclonal antibodies. *Cancer immunology, immunotherapy: CII* 37, 255 (September 1993).

125. C. C. Benz, G. K. Scott, J. C. Sarup, R. M. Johnson, D. Tripathy, E. Coronado, H. M. Shepard, C. K. Osborne, Estrogen-dependent, tamoxifen-resistant tumorigenic growth of MCF-7 cells transfected with HER2/neu. *Breast cancer research and treatment* 24, 85 (1992).

126. J. Filmus, M. N. Pollak, R. Cailleau, R. N. Buick, MDA-468, a human breast cancer cell line with a high number of epidermal growth factor (EGF) receptors, has an amplified EGF receptor gene and is growth inhibited by EGF. *Biochemical and biophysical research communications* 128, 898 (Apr. 30, 1985).

127. J. Filmus, J. M. Trent, M. N. Pollak, R. N. Buick, Epidermal growth factor receptor gene-amplified MDA-468 breast cancer cell line and its nonamplified variants. *Molecular and cellular biology* 7, 251 (January 1987).

128. S. Yang, M. A. Raymond-Stintz, W. Ying, J. Zhang, D. S. Lidke, S. L. Steinberg, L. Williams, J. M. Oliver, B. S. Wilson, Mapping ErbB receptors on breast cancer cell membranes during signal transduction. *Journal of cell science* 120, 2763 (Aug. 15, 2007).

129. D. L. Costantini, K. Bateman, K. McLarty, K. A. Vallis, R. M. Reilly, Trastuzumab-resistant breast cancer cells remain sensitive to the auger electron-emitting radiotherapeutic agent 111In-NLS-trastuzumab and are radiosensitized by methotrexate. *Journal of nuclear medicine: official publication, Society of Nuclear Medicine* 49, 1498 (September 2008).

130. P. Nagy, A. Jenei, A. K. Kirsch, J. Szollosi, S. Damjanovich, T. M. Jovin, Activation-dependent clustering of the erbB2 receptor tyrosine kinase detected by scanning near-field optical microscopy. *Journal of cell science* 112 (Pt 11), 1733 (June 1999).

131. R. Kaufmann, P. Muller, G. Hildenbrand, M. Hausmann, C. Cremer, Analysis of Her2/neu membrane protein clusters in different types of breast cancer cells using localization microscopy. *Journal of microscopy* 242, 46 (April 2011).

132. B. J. Woodcroft, L. Hammond, J. L. Stow, N. A. Hamilton, Automated organelle-based colocalization in whole-cell imaging. *Cytometry. Part A: the journal of the International Society for Analytical Cytology* 75, 941 (November 2009).

133. D. A. Lauffenburger, J. J. Linderman, *Receptors Models for Binding, Trafficking, and Signaling.* (Oxford University Press, New York, N.Y., 1993), pp. 365.

134. A. S. Perelson, Receptor Clustering on a Cell Surface. I. Theory of Receptor Cross-linking by Ligands Rearing Two Chemically Identical Functional Groups. *Mathematical Biosciences* 48, 71 (1980).

135. A. S. Perelson, Receptor clustering on a cell surface. III. Theory of receptor cross-linking by multivalent ligands: description by ligand states. *Mathematical Biosciences* 53, 1 (1981).

136. A. S. Perelson, Receptor Clustering on a Cell Surface. II. Theory of Receptor Cross-linking by Ligands Bearing Two Chemically Distinct Functional Groups. *Mathematical Biosciences* 49, 87 (1980).

137. C. M. Waters, K. C. Oberg, G. Carpenter, K. A. Overholser, Rate constants for binding, dissociation, and internalization of EGF: effect of receptor occupancy and ligand concentration. *Biochemistry* 29, 3563 (Apr. 10, 1990).

138. C. Wofsy, B. Goldstein, K. Lund, H. S. Wiley, Implications of epidermal growth factor (EGF) induced egf receptor aggregation. *Biophysical journal* 63, 98 (July 1992).

139. A. Gandolfi, M. A. Giovenco, Reversible binding of multivalent antigen in the control of B lymphocyte activation. *Journal of theoretical biology* 74, 513 (Oct. 21, 1978).

140. C. DeLisi, The biophysics of ligand-receptor interactions. *Quarterly reviews of biophysics* 13, 201 (May, 1980).

141. B. S. Hendriks, L. K. Opresko, H. S. Wiley, D. Lauffenburger, Quantitative analysis of HER2-mediated effects on HER2 and epidermal growth factor receptor endocytosis: distribution of homo- and heterodimers depends on relative HER2 levels. *The Journal of biological chemistry* 278, 23343 (Jun. 27, 2003).

142. T. C. Werner, J. R. Bunting, R. E. Cathou, The shape of immunoglobulin G molecules in solution. *Proceedings of the National Academy of Sciences of the United States of America* 69, 795 (April 1972).

143. R. E. Cathou, D. A. Holowka, Evolution of conformational flexibility of immunoglobulin M. *Advances in experimental medicine and biology* 64, 207 (1975).

The foregoing written specification and the claims that follow are considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

What is claimed is:

1. A ligand-drug particle comprising a lipid surface layer, at least one drug in the interior of the particle or embedded in the lipid surface layer, and a ligand specific for a cell surface receptor on a target cell, wherein:
   a. the ligand is exposed on the lipid surface layer;
   b. the ligand binds to its receptor with an in vitro binding affinity of 0.001 to 1000 nM;
   c. the target cell that the particle targets comprises an average number of receptors per cell ranging from $10^5$ to $10^7$ receptors per cell; and
   d. the particle has a ligand valency that depends upon the ligand-receptor in vitro binding affinity and the average number of receptors per target cell, wherein the ligand valency is as follows:
      i. a valency of 6-10 where the target cell has an average number of receptors per cell on the order of $3 \times 10^6$ receptors per cell;
      ii. a valency of 10-16 where the target cell has an average number of receptors per cell on the order of $1 \times 10^6$ receptors per cell;

iii. a valency of 10-20 where the target cell has an average number of receptors per cell on the order of $9 \times 10^5$ receptors per cell;
iv. a valency of 11-21 where the target cell has an average number of receptors per cell on the order of $8 \times 10^5$ receptors per cell;
v. a valency of 12-23 where the target cell has an average number of receptors per cell on the order of $7 \times 10^5$ receptors per cell;
vi. a valency of 13-25 where the target cell has an average number of receptors per cell on the order of $6 \times 10^5$ receptors per cell;
vii. a valency of 15-29 where the target cell has an average number of receptors per cell on the order of $5 \times 10^5$ receptors per cell;
viii. a valency of 18-36 where the target cell has an average number of receptors per cell on the order of $4 \times 10^5$ receptors per cell;
ix. a valency of 15-36 where the target cell has an average number of receptors per cell on the order of $4 \times 10^5$ to $5 \times 10^5$ receptors per cell;
x. a valency of 13-29 where the target cell has an average number of receptors per cell on the order of $5 \times 10^5$ to $6 \times 10^5$ receptors per cell;
xi. a valency of 12-25 where the target cell has an average number of receptors per cell on the order of $6 \times 10^5$ to $7 \times 10^5$ receptors per cell;
xii. a valency of 11-23 where the target cell has an average number of receptors per cell on the order of $7 \times 10^5$ to $8 \times 10^5$ receptors per cell;
xiii. a valency of 10-21 where the target cell has an average number of receptors per cell on the order of $8 \times 10^5$ to $9 \times 10^5$ receptors per cell;
xiv. a valency of 10-16 or 18-20 where the target cell has an average number of receptors per cell on the order of $9 \times 10^5$ to $1 \times 10^6$ receptors per cell; or
xv. a valency of 6-10, 12-16, or 19 where the target cell has an average number of receptors per cell on the order of $1 \times 10^6$ to $3 \times 10^6$ receptors per cell.

2. The ligand-drug particle according to claim 1, wherein the ligand-receptor in vitro binding affinity is 0.1 to 10 nM and the particle has a ligand valency as follows:
   a. a valency of 8-10 where the target cell has an average number of receptors per cell on the order of $3 \times 10^6$ receptors per cell;
   b. a valency of 13-16 where the target cell has an average number of receptors per cell on the order of $9 \times 10^5$ to $1 \times 10^6$ receptors per cell;
   c. a valency of 14-18 where the target cell has an average number of receptors per cell on the order of $8 \times 10^5$ receptors per cell;
   d. a valency of 15-19 where the target cell has an average number of receptors per cell on the order of $7 \times 10^5$ receptors per cell;
   e. a valency of 17-21 where the target cell has an average number of receptors per cell on the order of $6 \times 10^5$ receptors per cell;
   f. a valency of 19-24 where the target cell has an average number of receptors per cell on the order of $5 \times 10^5$ receptors per cell; or
   g. a valency of 24-30 where the target cell has an average number of receptors per cell on the order of $4 \times 10^5$ receptors per cell.

3. The ligand-drug particle according to claim 1, wherein the ligand-receptor in vitro binding affinity is 0.001 to 0.1 nM and the particle has a ligand valency as follows:
   a. a valency of 15-24 where the target cell has an average number of receptors per cell on the order of $4 \times 10^5$ to $5 \times 10^5$ receptors per cell;
   b. a valency of 13-19 where the target cell has an average number of receptors per cell on the order of $5 \times 10^5$ to $6 \times 10^5$ receptors per cell;
   c. a valency of 12-17 where the target cell has an average number of receptors per cell on the order of $6 \times 10^5$ to $7 \times 10^5$ receptors per cell;
   d. a valency of 11-15 where the target cell has an average number of receptors per cell on the order of $7 \times 10^5$ to $8 \times 10^5$ receptors per cell;
   e. a valency of 10-14 where the target cell has an average number of receptors per cell on the order of $8 \times 10^5$ to $9 \times 10^5$ receptors per cell;
   f. a valency of 10-13 where the target cell has an average number of receptors per cell on the order of $9 \times 10^5$ to $1 \times 10^6$ receptors per cell; or
   g. a valency of 6-13 where the target cell has an average number of receptors per cell on the order of $1 \times 10^6$ to $3 \times 10^6$ receptors per cell.

4. The ligand-drug particle according to claim 1, wherein the ligand-receptor in vitro binding affinity is 0.1 to 10 nM and the particle has a ligand valency as follows:
   a. a valency of 19-30 where the target cell has an average number of receptors per cell on the order of $4 \times 10^5$ to $5 \times 10^5$ receptors per cell;
   b. a valency of 17-24 where the target cell has an average number of receptors per cell on the order of $5 \times 10^5$ to $6 \times 10^5$ receptors per cell;
   c. a valency of 15-21 where the target cell has an average number of receptors per cell on the order of $6 \times 10^5$ to $7 \times 10^5$ receptors per cell;
   d. a valency of 14-19 where the target cell has an average number of receptors per cell on the order of $7 \times 10^5$ to $8 \times 10^5$ receptors per cell;
   e. a valency of 13-18 where the target cell has an average number of receptors per cell on the order of $8 \times 10^5$ to $9 \times 10^5$ receptors per cell;
   f. a valency of 13-16 where the target cell has an average number of receptors per cell on the order of $9 \times 10^5$ to $1 \times 10^6$ receptors per cell; or
   g. a valency of 8-16 where the target cell has an average number of receptors per cell on the order of $1 \times 10^6$ to $3 \times 10^6$ receptors per cell.

5. The ligand-drug particle according to claim 1, wherein the ligand-receptor in vitro binding affinity is 10 to 1000 nM and the particle has a ligand valency as follows:
   a. a valency of 24-36 where the target cell has an average number of receptors per cell on the order of $4 \times 10^5$ to $5 \times 10^5$ receptors per cell;
   b. a valency of 21-29 where the target cell has an average number of receptors per cell on the order of $5 \times 10^5$ to $6 \times 10^5$ receptors per cell;
   c. a valency of 19-25 where the target cell has an average number of receptors per cell on the order of $6 \times 10^5$ to $7 \times 10^5$ receptors per cell;
   d. a valency of 18-23 where the target cell has an average number of receptors per cell on the order of $7 \times 10^5$ to $8 \times 10^5$ receptors per cell;
   e. a valency of 16-21 where the target cell has an average number of receptors per cell on the order of $8 \times 10^5$ to $9 \times 10^5$ receptors per cell;
   f. a valency of 16 or 18-20 where the target cell has an average number of receptors per cell on the order of $9 \times 10^5$ to $1 \times 10^6$ receptors per cell; or g. a valency of 10, 12-16, or 18-19 where the target cell has an average on the order of $1 \times 10^6$ to $3 \times 10^6$ receptors per cell.

6. The ligand-drug particle according to claim 1, wherein the ligand is an antibody, an antigen binding fragment of an antibody, or an Fv, scFv, Fab', or F(ab')$_2$ fragment.

7. The ligand-drug particle according to claim 1, wherein the lipid surface layer is a lipid bilayer or a lipid monolayer.

8. The ligand-drug particle according to claim 1, wherein the at least one drug comprises a polar, small molecule compound located in an aqueous space at the interior of the particle, or a hydrophobic, small molecule compound embedded in the lipid surface layer.

9. The ligand-drug particle according to claim 1, wherein the particle further comprises a coating comprising polyethylene glycol (PEG).

10. A ligand-drug particle comprising a lipid surface layer, at least one drug in the interior of the particle or embedded in the lipid surface layer, a first ligand specific for a first cell surface receptor on a target cell, and a second ligand specific for a second cell surface receptor on the target cell, wherein:
   a. the first and second ligands are exposed on the lipid surface layer;
   b. the first and second ligands bind to their respective first and second receptors with in vitro binding affinity of 0.1 to 100 nM;
   c. the target cell that the particle targets comprises (i) an average number of the first receptor per target cell ranging from $10^3$ to $10^7$ and (ii) an average number of the second receptor per target cell ranging from $10^3$ to $10^7$; and
   d. the particle has a ligand valency that depends on the in vitro binding affinity for each of the first receptor and the second receptor and their respective ligands, the average number of the first receptor per target cell, the average number of the second receptor per target cell, and whether ligand-receptor binding is additive or synergistic; wherein the ligand valency for each of the first and second ligands is as follows:
      i. a valency of 13-17 where each of the first and the second receptors is highly expressed by the target cell, and where binding of the first and the second receptors by the first and the second ligands, respectively, is additive;
      ii. a valency of 9-13 where each of the first and the second receptors is highly expressed by the target cell, and where binding of the first and the second receptors by the first and the second ligands, respectively, is synergistic;
      iii. a valency of 13-17 where one receptor of the first and the second receptors is highly expressed by the target cell and the other receptor of the first and the second receptors is moderately expressed by the target cell, and where binding of the first and the second receptors by the first and the second ligands, respectively, is additive;
      iv. a valency of 7-10 where one receptor of the first and the second receptors is highly expressed by the target cell and the other receptor of the first and the second receptors is moderately expressed by the target cell, and where binding of the first and the second receptors by the first and the second ligands, respectively, is synergistic;
      v. a valency of 15-21 where each receptor of the first and the second receptors is moderately expressed by the target cell, and where binding of the first and the second receptors by the first and the second ligands, respectively, is additive; or
      vi. a valency of 11-15 where each receptor of the first and the second receptors is moderately expressed by the target cell, and where binding of the first and the second receptors by the first and the second ligands, respectively, is synergistic.

11. The ligand-drug particle according to claim 10, wherein the particle has a ligand valency for each of the first and second ligands as follows:
   a. a valency of 17-21 where the in vitro binding affinity for each of the first and the second receptors and their respective ligands is on the order of 100 nM, and binding is additive;
   b. a valency of 16-20 where the in vitro binding affinity for one of the first and the second receptors and their respective ligands is on the order of 100 nM, the in vitro binding affinity for another of the first and the second receptors and their respective ligands is on the order of 10 nM, and binding is additive;
   c. a valency of 16-19 where the in vitro binding affinity for one of the first and the second receptors and their respective ligands is on the order of 100 nM, the in vitro binding affinity for another of the first and the second receptors and their respective ligands is on the order of 1 nM, and binding is additive;
   d. a valency of 15-19 where the in vitro binding affinity for one of the first and the second receptors and their respective ligands is on the order of 100 nM, the in vitro binding affinity for another of the first and the second receptors and their respective ligands is on the order of 0.1 nM, and binding is additive;
   e. a valency of 16-19 where the in vitro binding affinity for each of the first and the second receptors and their respective ligands is on the order of 10 nM, and binding is additive;
   f. a valency of 15-18 where the in vitro binding affinity for one of the first and the second receptors and their respective ligands is on the order of 10 nM, the in vitro binding affinity for another of the first and the second receptors and their respective ligands is on the order of 1 nM, and binding is additive;
   g. a valency of 14-17 where the in vitro binding affinity for one of the first and the second receptors and their respective ligands is on the order of 10 nM, the in vitro binding affinity for another of the first and the second receptors and their respective ligands is on the order of 0.1 nM, and binding is additive;
   h. a valency of 14-17 where the in vitro binding affinity for each of the first and the second receptors and their respective ligands is on the order of 1 nM, and binding is additive;
   i. a valency of 13-16 where the in vitro binding affinity for one of the first and the second receptors and their respective ligands is on the order of 1 nM, the in vitro binding affinity for another of the first and the second receptors and their respective ligands is on the order of 0.1 nM, and binding is additive;
   j. a valency of 13-15 where the in vitro binding affinity for each of the first and the second receptors and their respective ligands is on the order of 0.1 nM, and binding is additive;
   k. a valency of 10-15 where the in vitro binding affinity for each of the first and the second receptors and their respective ligands is on the order of 100 nM, and binding is synergistic;

l. a valency of 10-15 where the in vitro binding affinity for one of the first and the second receptors and their respective ligands is on the order of 100 nM, the in vitro binding affinity for another of the first and the second receptors and their respective ligands is on the order of 10 nM, and binding is synergistic;

m. a valency of 10-15 where the in vitro binding affinity for one of the first and the second receptors and their respective ligands is on the order of 100 nM, the in vitro binding affinity for another of the first and the second receptors and their respective ligands is on the order of 1 nM, and binding is synergistic;

n. a valency of 10-15 where the in vitro binding affinity for one of the first and the second receptors and their respective ligands is on the order of 100 nM, the in vitro binding affinity for another of the first and the second receptors and their respective ligands is on the order of 0.1 nM, and binding is synergistic;

o. a valency of 9-13 where the in vitro binding affinity for each of the first and the second receptors and their respective ligands is on the order of 10 nM, and binding is synergistic;

p. a valency of 9-13 where the in vitro binding affinity for one of the first and the second receptors and their respective ligands is on the order of 10 nM, the in vitro binding affinity for another of the first and the second receptors and their respective ligands is on the order of 1 nM, and binding is synergistic;

q. a valency of 9-13 where the in vitro binding affinity for one of the first and the second receptors and their respective ligands is on the order of 10 nM, the in vitro binding affinity for another of the first and the second receptors and their respective ligands is on the order of 0.1 nM, and binding is synergistic;

r. a valency of 8-12 where the in vitro binding affinity for each of the first and the second receptors and their respective ligands is on the order of 1 nM, and binding is synergistic;

s. a valency of 8-12 where the in vitro binding affinity for one of the first and the second receptors and their respective ligands is on the order of 1 nM, the in vitro binding affinity for another of the first and the second receptors and their respective ligands is on the order of 0.1 nM, and binding is synergistic; or t. a valency of 7-11 where the in vitro binding affinity for each of the first and the second receptors and their respective ligands is on the order of 0.1 nM, and binding is synergistic.

12. The ligand-drug particle according to claim 10, wherein at least one of the first and second ligands is an antibody, an antigen binding fragment of an antibody, an Fv fragment, a scFv fragment, an Fab' fragment, or F(ab')$_2$ fragment, or wherein both ligands are antibodies, antigen binding fragments of antibodies, Fv fragments, scFv fragments, Fab' fragments, or F(ab')$_2$ fragments.

13. The ligand-drug particle according to claim 10, wherein the lipid surface layer is a lipid bilayer or a lipid monolayer.

14. The ligand-drug particle according to claim 10, wherein the at least one drug comprises a polar, small molecule compound located in an aqueous space at the interior of the particle, or a hydrophobic, small molecule compound embedded in the lipid surface layer.

15. The ligand-drug particle according to claim 10, wherein the particle further comprises a coating comprising polyethylene glycol (PEG).

16. The ligand-drug particle of claim 1, wherein the particle is 70-120 nm, 80-110 nm, 90-110 nm, 70 nm, 75 nm, 80 nm, 85 nm, 90 nm, 95 nm, 100 nm, 105 nm, 110 nm, 115 nm, or 120 nm in diameter.

* * * * *